US009556166B2

(12) United States Patent
Foley et al.

(10) Patent No.: US 9,556,166 B2
(45) Date of Patent: Jan. 31, 2017

(54) PROTEOSTASIS REGULATORS

(75) Inventors: Megan Foley, Cambridge, MA (US);
Bradley Tait, Malden, MA (US);
Matthew Cullen, Braintree, MA (US)

(73) Assignee: Proteostasis Therapeutics, Inc., Cambridge, MA (US)

( * ) Notice: Subject to any disclaimer, the term of this patent is extended or adjusted under 35 U.S.C. 154(b) by 494 days.

(21) Appl. No.: 13/468,757

(22) Filed: May 10, 2012

(65) Prior Publication Data
US 2012/0316193 A1 Dec. 13, 2012

Related U.S. Application Data

(60) Provisional application No. 61/485,421, filed on May 12, 2011.

(51) Int. Cl.
| | |
|---|---|
| C07D 401/06 | (2006.01) |
| C07D 403/06 | (2006.01) |
| C07D 405/06 | (2006.01) |
| C07D 471/04 | (2006.01) |
| C07D 207/333 | (2006.01) |
| C07D 207/337 | (2006.01) |
| C07D 231/12 | (2006.01) |
| C07D 249/06 | (2006.01) |
| C07D 263/32 | (2006.01) |
| C07D 275/02 | (2006.01) |
| C07D 295/185 | (2006.01) |
| C07D 333/20 | (2006.01) |

(52) U.S. Cl.
CPC ......... *C07D 471/04* (2013.01); *C07D 207/333* (2013.01); *C07D 207/337* (2013.01); *C07D 231/12* (2013.01); *C07D 249/06* (2013.01); *C07D 263/32* (2013.01); *C07D 275/02* (2013.01); *C07D 295/185* (2013.01); *C07D 333/20* (2013.01); *C07D 401/06* (2013.01); *C07D 403/06* (2013.01); *C07D 405/06* (2013.01)

(58) Field of Classification Search
None
See application file for complete search history.

(56) References Cited

U.S. PATENT DOCUMENTS

| | | | |
|---|---|---|---|
| 4,148,895 A | 4/1979 | Lattrell et al. |
| 4,290,940 A | 9/1981 | Wirth et al. |
| 4,814,344 A | 3/1989 | Humber et al. |
| 5,561,149 A | 10/1996 | Azria et al. |
| 5,852,046 A | 12/1998 | Lang et al. |
| 5,859,035 A | 1/1999 | Anthony et al. |
| 6,063,782 A | 5/2000 | Kimura et al. |
| 6,201,129 B1 | 3/2001 | Chuncharprasert et al. |
| 6,310,217 B1 | 10/2001 | Lehr |
| 6,469,171 B1 | 10/2002 | Banwell et al. |
| 6,500,853 B1 | 12/2002 | Seehra et al. |
| 6,589,954 B1 | 7/2003 | Mavunkel et al. |
| 6,627,645 B2 | 9/2003 | Andersson et al. |
| 6,828,344 B1 | 12/2004 | Seehra et al. |
| 6,867,209 B1 | 3/2005 | Mavunkel et al. |
| 7,238,713 B2 | 7/2007 | Anderson et al. |
| 7,417,063 B2 | 8/2008 | Smallheer et al. |
| 7,425,642 B2 | 9/2008 | Watanabe et al. |
| 7,482,354 B2 | 1/2009 | Traquandi et al. |
| 7,528,165 B2 | 5/2009 | Hsieh et al. |
| 7,576,206 B2 | 8/2009 | Bernardini et al. |
| 7,632,955 B2 | 12/2009 | Hsieh et al. |
| 7,767,817 B2 | 8/2010 | Wang et al. |
| 7,781,479 B2 | 8/2010 | Takahashi et al. |
| 8,097,644 B2 | 1/2012 | Beard et al. |
| 8,197,819 B2 | 6/2012 | Srivastava et al. |
| 8,293,781 B2 | 10/2012 | Tomoo et al. |
| 2002/0037887 A1 | 3/2002 | Pintor et al. |
| 2004/0122096 A1 | 6/2004 | Lang et al. |
| 2005/0075348 A1 | 4/2005 | Harriman et al. |
| 2005/0113357 A1 | 5/2005 | Anderson et al. |
| 2006/0116379 A1 | 6/2006 | Ogawa et al. |
| 2006/0135540 A1 | 6/2006 | Lin et al. |
| 2007/0185184 A1 | 8/2007 | Hanson et al. |
| 2007/0203121 A1 | 8/2007 | Merce Vidal et al. |
| 2008/0171772 A1 | 7/2008 | Beard et al. |
| 2008/0188453 A1 | 8/2008 | Adams et al. |
| 2009/0047246 A1 | 2/2009 | Beigelman et al. |
| 2009/0118503 A1 | 5/2009 | Sprott et al. |

(Continued)

FOREIGN PATENT DOCUMENTS

| | | |
|---|---|---|
| CN | 101016294 A | 8/2007 |
| DE | 4325204 A1 | 2/1995 |

(Continued)

OTHER PUBLICATIONS

De Freitas, G., B.L., et al., "Development of Co MFA and CoMSIA models of affinity and selectivity for indole ligands of cannabinoid CB1 and CB2 receptors," European Journal of Medicinal Chemistry, 44: 2482-2496 (2009).
Lee, B. H. et al., "Enhancement of proteasome activity by a small-molecule inhibitor of USP14", Nature, 2010, 467, 179-184.
CAS RN 784194-52-1, STN Entry Date Nov. 19, 2004.
CAS RN 133674-62-1, STN Entry Date May 10, 1991.
CAS RN 57248-18-7, STN Entry Date Nov. 16, 1984.
CAS RN 169501-21-7, STN Entry Date Nov. 1, 1995.
Gadaginamath, G. S., et al., "Synthesis and antimicrobial activity of 4-isogramines, 4-arylthiomethyl and 3-aminoacetyl derivatives of 2-methylindoles," Revue Roumaine de Chimie, 40(3): 265-273 (1995).

(Continued)

*Primary Examiner* — Bong-Sook Baek
(74) *Attorney, Agent, or Firm* — Elmore Patent Law Group, P.C.; Mahreen Chaudhry Hoda; Carolyn S. Elmore, Esq.

(57) ABSTRACT

The present invention is directed to compounds having the Formulae (Ia-Ie), (II), (IIIa-IIId), (IVa-IVc), (Va-Vb), (VIa-VIe), (VII), (VIIIa-VIIIc), and (IX), pharmaceutically acceptable salts, prodrugs and solvates thereof, compositions of any of thereof and methods for the treatment of a condition associated with a dysfunction in proteostasis comprising an effective amount of these compounds.

5 Claims, No Drawings

(56) References Cited

U.S. PATENT DOCUMENTS

| | | | |
|---|---|---|---|
| 2009/0143371 A1 | 6/2009 | Buettelmann et al. | |
| 2009/0163545 A1 | 6/2009 | Goldfarb | |
| 2009/0215750 A1 | 8/2009 | Bamberg et al. | |
| 2009/0227538 A1 | 9/2009 | Fruchtel et al. | |
| 2009/0264384 A1 | 10/2009 | Didsbury et al. | |
| 2009/0264457 A1 | 10/2009 | Codony-Soler et al. | |
| 2009/0318446 A1 | 12/2009 | Fischer et al. | |
| 2010/0074955 A1 | 3/2010 | Buschmann et al. | |
| 2010/0087415 A1 | 4/2010 | Whitten et al. | |
| 2010/0087446 A1 | 4/2010 | Chakravarty et al. | |
| 2010/0099726 A1 | 4/2010 | Cantley et al. | |
| 2010/0113777 A1* | 5/2010 | Tomoo | C07D 209/08 544/143 |
| 2010/0197708 A1 | 8/2010 | Talley et al. | |
| 2010/0204282 A1 | 8/2010 | Hutchinson et al. | |
| 2010/0249069 A1 | 9/2010 | Donello et al. | |
| 2010/0331297 A1 | 12/2010 | Bulawa et al. | |
| 2011/0009453 A1 | 1/2011 | Donello et al. | |
| 2011/0098483 A1 | 4/2011 | Petasis et al. | |
| 2011/0144090 A1 | 6/2011 | Elder et al. | |
| 2011/0319403 A1 | 12/2011 | Aslanian et al. | |
| 2012/0006417 A1 | 1/2012 | Folk | |
| 2012/0022057 A1 | 1/2012 | Aslanian et al. | |
| 2012/0064175 A1 | 3/2012 | Vukovic et al. | |
| 2012/0071448 A1 | 3/2012 | Donello et al. | |
| 2012/0245186 A1 | 9/2012 | Blackman et al. | |
| 2012/0316193 A1 | 12/2012 | Foley et al. | |
| 2013/0029948 A1 | 1/2013 | Roppe et al. | |
| 2013/0045992 A1 | 2/2013 | Finley et al. | |
| 2013/0150385 A1 | 6/2013 | Blackman et al. | |
| 2013/0156755 A1 | 6/2013 | Blackman et al. | |
| 2013/0171105 A1 | 7/2013 | Blackman et al. | |

FOREIGN PATENT DOCUMENTS

| | | |
|---|---|---|
| EP | 562832 | 9/1993 |
| EP | 562832 A1 | 9/1993 |
| EP | 639573 | 2/1995 |
| EP | 639573 A1 | 2/1995 |
| EP | 1837329 A1 | 9/2007 |
| EP | 2020230 A1 | 2/2009 |
| EP | 2141148 A1 | 1/2010 |
| EP | 2141163 A1 | 1/2010 |
| GB | 1073521 | 6/1967 |
| GB | 1410783 | 10/1975 |
| JP | 07-133274 A | 5/1995 |
| JP | 08-225535 A | 9/1996 |
| JP | 10-508321 A | 8/1998 |
| JP | 11-503445 A | 3/1999 |
| JP | 11-503758 A | 3/1999 |
| JP | 2000063354 | 2/2000 |
| JP | 2000063354 A | 2/2000 |
| JP | 2001151771 A | 6/2001 |
| JP | 2002-510622 A | 4/2002 |
| JP | 2003-501476 A | 1/2003 |
| JP | 2007-519631 A | 7/2007 |
| JP | 2009179589 A | 8/2009 |
| WO | 9513266 A1 | 5/1995 |
| WO | 96/32379 A1 | 10/1996 |
| WO | 9736881 A1 | 10/1997 |
| WO | 9746226 A2 | 12/1997 |
| WO | 98/27089 A1 | 6/1998 |
| WO | 9943672 A1 | 9/1999 |
| WO | 0144182 A1 | 6/2001 |
| WO | 03041644 A2 | 5/2003 |
| WO | 2004/020409 A1 | 3/2004 |
| WO | 2004/104007 | 12/2004 |
| WO | 2005/021558 | 3/2005 |
| WO | 2005/025515 | 3/2005 |
| WO | 2005/066126 A1 | 7/2005 |
| WO | 2005/121175 A2 | 12/2005 |
| WO | 2006/087355 | 8/2006 |
| WO | 2006/125324 A1 | 11/2006 |
| WO | 2007095561 A2 | 8/2007 |
| WO | 2008/024978 A2 | 2/2008 |
| WO | 2008/100867 A2 | 8/2008 |
| WO | 2008/109702 A1 | 9/2008 |
| WO | 2008/147536 | 12/2008 |
| WO | 2009013010 A2 | 1/2009 |
| WO | 2009/023623 A1 | 2/2009 |
| WO | 2009/062118 | 5/2009 |
| WO | 2009/071577 | 6/2009 |
| WO | 2009/073620 | 6/2009 |
| WO | 2009/097141 | 8/2009 |
| WO | 2009/108551 | 9/2009 |
| WO | 2009/117676 | 9/2009 |
| WO | 2009/127686 A1 | 10/2009 |
| WO | 2009/130481 A1 | 10/2009 |
| WO | 2009118292 A1 | 10/2009 |
| WO | 2009/136175 | 11/2009 |
| WO | 2009/158011 | 12/2009 |
| WO | 2009/158371 | 12/2009 |
| WO | 2010/006234 A2 | 1/2010 |
| WO | 2010/019391 A1 | 2/2010 |
| WO | 2010/067123 A1 | 6/2010 |
| WO | 2010/139982 A1 | 12/2010 |
| WO | 2010015816 A2 | 2/2011 |
| WO | 2011038579 A1 | 4/2011 |
| WO | 2011/094545 A2 | 8/2011 |
| WO | 2011094545 A2 | 8/2011 |
| WO | 2011/127333 A2 | 10/2011 |
| WO | 2011/133653 A1 | 10/2011 |
| WO | 2012/012712 | 1/2012 |
| WO | 2012078757 A2 | 6/2012 |
| WO | 2012096919 A1 | 7/2012 |
| WO | 2012106343 A2 | 8/2012 |
| WO | 2012116061 A1 | 8/2012 |
| WO | 2012116247 A1 | 8/2012 |
| WO | 2012141796 A2 | 10/2012 |
| WO | 2012162293 A1 | 11/2012 |
| WO | 2012162372 A1 | 11/2012 |
| WO | 2012162584 A1 | 11/2012 |
| WO | 2013006864 A2 | 1/2013 |
| WO | 2013014104 A1 | 1/2013 |
| WO | 2013/074594 A1 | 5/2013 |
| WO | 2013067162 A1 | 5/2013 |
| WO | 2013067165 A1 | 5/2013 |

OTHER PUBLICATIONS

Iwaki, T., et al., "Water-Soluble Melatonins: Syntheses of Melatonins Carrying a Glycosyl Group at the 1-Position," Heterocyles, 60(6): 1411-1418 (2003).

Aparoy, P., et al., "Pharmacophore modeling and virtual screening for designing potential 5-Lipoxygenase inhibitors," Bioorganic & Medicinal Chemistry Letters, 20(3):1013-1018 (2010).

Van Zandt, M. C., et al., "Discovery of 3-[(4,5,7-Trifluorobenzothiazol-2-yl)methyl]indole-N-acetic Acid (Lidorestat) and Congeners as Highly Potent and Selective Inhibitors of Aldose Reductase for Treatment of Chronic Diabetic Complications," J. Med. Chem., 48: 3141-3152 (2005).

Liu, W., et al., "Discovery of a Peroxisome Proliferator Activated Receptor γ (PPARγ) Modulator with Balanced PPARα Activity for the Treatment of Type 2 Diabetes and Dyslipidemia," J. Med. Chem., 52(14): 4443-4453 (2009).

Stearns, B. A., et al., "Synthesis and biological evaluation of 6-aryl-6H-pyrrolo[3,4-d]pyridazine derivatives: high-affinity ligands to the α2δ subunit of voltage gated calcium channels," Bioorganic & Medicinal Chemistry Letters, 14(5): 1295-1298 (2004).

Vidovic, D., et al., "A Combined Ligand- and Structure-Based Virtual Screening Protocol Identifies Submicromolar PPAR[γ] Partial Agonists," Chem Med Chem, 6(1): 94-103 (2011).

Marchand, P., et al., "Synthesis and structure-activity relationships of N-aryl(indol-3-yl)glyoxamides as antitumor agents", Bioorganic & Medicinal Chemistry, 17(18): 6715-6727 (2009).

Preobrazhenskaya, M. N., et al., "Synthesis and Study of the Pharmacological Activity of 1-(Indolyl-3')-2-Alkylaminoethanols", Pharmaceutical Chemistry Journal, pp. 532-536 (1970). Retrieved from the Internet: URL:http://rd.springer.com/content/pdf/10.1007/BF00763238.pdf [retrieved on Oct. 7, 2014].

(56) References Cited

OTHER PUBLICATIONS

Abdel-Motaleb, R., M., et al., "Studies with azoles and benzoazoles: A novel simple approach for synthesis of 3-functionally substituted 3-acylindoles", Journal of Heterocyclic Chemistry, 44 (1): 109-114 (2007).
Rao, R. K., et al., "An efficient, mild, and selective Ullmann-type N-arylation of indoles catalyzed by copper(I) complex", Tetrahedron, 65(23): 4619-4624 (2009).
Gitto, R. et al., "Development of 3-substituted-1H-indole derivatives as NR2B/NMDA receptor antagonists", Bioorganic & Medicinal Chemistry, 17(4): 1640-1647 (2009).
Gadaginamath et al., "Synthesis and Antimicrobial Activity of Novel 3-Thiazolyl/Imidazo (2, 1-b)-1 ,3,4-Thiadiazolyi/Anilinoacetyi/PhenoxyacetylIndole Derivatives," Indian Journal of Heterocyclic Chemistry, 9(1 ):33-38 (1999).
Kang et al., "Cell Cycle Arrest and Cytochrome c-mediated Apoptotic Induction in A549 Human Lung Cancer Cells by MCS-C2, an Analog of Sangivamycin," Journal of Microbiology and Biotechnology, 20(2):428-432 (2010).
Registry (STN) CAS Registration No. 380907-35-7.
Registry (STN) CAS Registration No. 314261-13-7.
Registry (STN) CAS Registration No. 3257 42-01-6.
Registry (STN) CAS Registration No. 670268-20-9.
Supplementary European Search Report from EP 11 73 7731 dated Jul. 3, 2014.
International Search Report dated Oct. 24, 2011, from PCT/US2011/022929.
Office Action dated Aug. 18, 2014 from U.S. Appl. No. 13/575,812.
Office Action dated Feb. 5, 2015 from U.S. Appl. No. 13/575,812.
U.S. Appl. No. 14/933,671, filed Nov. 5, 2015.
Cavalli, A., et al., "Toward a Pharmacophore for Drugs Inducing the Long QT Syndrome: Insights from a CoMFA Study of HERG K + Channel Blockers", Journal of Medicinal Chemistry, vol. 45, No. 18, Aug. 1, 2002 (Aug. 1, 2002), pp. 3844-3853, XP055281643.
Brana, M. F., et al., "Synthesis and biological activity of N,N-dialkylaminoalkyl-substituted bisindolyl and diphenyl pyrazolone derivatives", Bioorganic & Medicinal Chemistry, Pergamon, GB, vol. 14, No. 1, Jan. 1, 2006 (Jan. 1, 2006), pp. 9-16, XP027992247.
CAS Registry No. 500774-96-9, STN Entry Date Mar. 27, 2003.
CAS Registry No. 1027660-19-0, STN Entry Date Jun. 12, 2008.
CAS Registry No. 1026840-66-3, STN Entry Date Jun. 9, 2008.
CAplus Accession No. 1929:33387.
CAS Registry No. 857810-06-1, STN Entry Date Aug. 1, 2005.
Kumar, D., et al., "A facile and regioselective synthesis of 1,4-disubstituted 1,2,3-triazoles using click chemistry," Tetrahedron Letters, 50(18): 2065-2068 (2009).
(STN International, File Registry [online] RN 1266216-33-4, RN 1266208-38-1, RN 1266193-66-1, RN 1266184-43-3, RN 1266168-16-4, RN 1266155-14-9, RN 1266153-33-6, RN 1266150-22-4, RN 1266137-42-1, RN 1266131-49-0, (Mar. 3, 2011).
Machine Translation of JP2001151771A, p. 1-40, retrieved from https://www4.j-platpat.inpit.go.jp/cgi-bin/trao _web_cgi_ ejje?u=http://www4.j-platpat.inpit . . . , (2001).

* cited by examiner

PROTEOSTASIS REGULATORS

RELATED APPLICATION

This Application claims the benefit of U.S. Provisional Application No. 61/485,421 filed May 12, 2011. The entire teachings of the above application are incorporated herein by reference.

BACKGROUND OF THE INVENTION

Cells normally maintain a balance between protein synthesis, folding, trafficking, aggregation, and degradation, referred to as protein homeostasis, utilizing sensors and networks of pathways [Sitia et al., *Nature* 426: 891-894, 2003; Ron et al., *Nat Rev Mol Cell Biol* 8: 519-529, 2007]. The cellular maintenance of protein homeostasis, or proteostasis, refers to controlling the conformation, binding interactions, location and concentration of individual proteins making up the proteome. Protein folding in vivo is accomplished through interactions between the folding polypeptide chain and macromolecular cellular components, including multiple classes of chaperones and folding enzymes, which minimize aggregation [Wiseman et al., *Cell* 131: 809-821, 2007]. Whether a given protein folds in a certain cell type depends on the distribution, concentration, and subcellular localization of chaperones, folding enzymes, metabolites and the like [Wiseman et al.]. Human loss of function diseases are often the result of a disruption of normal protein homeostasis, typically caused by a mutation in a given protein that compromises its cellular folding, leading to efficient degradation [Cohen et al., *Nature* 426: 905-909, 2003]. Human gain of function diseases are similarly frequently the result of a disruption in protein homeostasis leading to protein aggregation [Balch et al. (2008), *Science* 319: 916-919].

Dysfunction in proteostasis has been implicated in a diverse range of diseases including for example, neurodegenerative disease, metabolic diseases, inflammatory diseases and cancer. There remains a need in the art for compounds and pharmaceutical compositions to treat conditions associated with proteostasis dysfunction.

SUMMARY OF THE INVENTION

The present invention is directed to compounds having the Formulae (Ia-Ie), (II), (IIIa-IIId), (IVa-IVc), (Va-Vb), (VIa-VIe), (VII), (VIIIa-VIIIc), and (IX), pharmaceutically acceptable salts, prodrugs and solvates thereof, compositions of any of thereof, methods for the treatment of a patient suffering from a condition associated with a dysfunction in proteostasis comprising administering to said an effective amount of a compound of the invention, and methods for treating cancer or tumor comprising administering to said an effective amount of a compound of the invention.

In one embodiment, the invention is directed to a compound having the Formula (Ia):

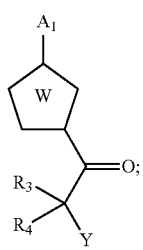

(Ia)

or a pharmaceutically acceptable salt, prodrug or solvate thereof, wherein:

Ring W is a 5-membered heteroaryl or a 5-membered heterocyclic, wherein each ring carbon atom of said 5-membered heteroaryl is substituted with one $R_d$ and wherein each ring nitrogen atom of said 5-membered heteroaryl is substituted with zero or one $R_d$ when said nitrogen atom is present, and wherein each ring carbon atom of said 5-membered heterocyclic is substituted with one or two $R_d$ and each ring nitrogen atom of said 5-membered heterocyclic is substituted with zero or one $R_d$, when said nitrogen atom or atoms are present;

$A_1$ is $S(O)_2R_a$, $S(O)_2NR_aR_a$, $C(O)NR_aR_a$, $C(O)R_a$, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, or optionally substituted $C_3$-$C_{12}$ cycloalkenyl, or is a monocyclic or polycyclic group selected from the group consisting of optionally substituted $C_3$-$C_{12}$ cycloalkyl, optionally substituted $C_4$-$C_{12}$ cycloalkenyl, optionally substituted 3- to 12-membered heterocyclic, optionally substituted aryl, optionally substituted heteroaryl;

Each $R_a$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

Each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, $CN$, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$; alternatively, two vicinal $R_d$ groups can be taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or yet alternatively, a vicinal $R_d$ and A can be taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted 3- to 12-membered heterocyclic, optionally substituted aryl, optionally substituted heteroaryl;

$R_3$ and $R_4$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $C(O)OR_c$, $NO_2$, $CN$, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$; alternatively, $R_3$ and $R_4$ can be taken together with the carbon atom to which they are attached to form a $C(O)$, $C_3$-$C_8$ cycloalkyl, $C_3$-$C_8$ cycloalkenyl or a 3- to 8-membered heterocyclic; or yet alternatively, $R_3$ and an $R_d$ group can be taken together to form a fused monocyclic group selected from the group consisting of $C_5$-$C_{12}$ cycloalkyl, $C_5$-$C_{12}$ cycloalkenyl, 5- to 12-membered heterocyclic, $C_5$-$C_{12}$ aryl, and 5-12 membered heteroaryl, each substituted with $R_4$ and Y, and optionally further substituted;

Y is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $OR_c$, $SR_c$, $C(O)OR_c$, $NO_2$, CN, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$, $(C=NR_c)R_c$, optionally substituted heterocyclic and optionally substituted heteroaryl, wherein said heterocyclic is C-attached to the carbon atom bonded to $R_3$ and $R_4$; or alternatively, $R_3$ or $R_4$ can be taken together with Y to form a $C_3$-$C_{12}$ cycloalkyl, $C_3$-$C_{12}$ cycloalkenyl, 3- to 12-membered heterocyclic, aryl, or heteroaryl, each optionally substituted;

Each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or alternatively, two $R_c$ groups are taken together with the atom which they are attached to form a $C_3$-$C_8$ cycloalkyl, $C_3$-$C_8$ cycloalkenyl, 3- to 8-membered heterocyclic, aryl or heteroaryl, each optionally substituted; and n is 0, 1 or 2.

In another embodiment, the invention is directed to a compound having the Formula

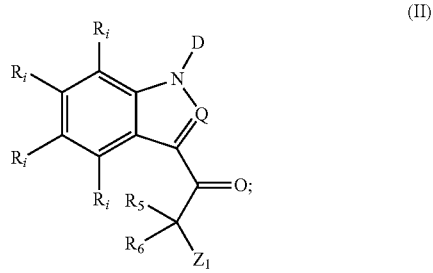

(II)

or a pharmaceutically acceptable salt, prodrug or solvate thereof, wherein:

D is hydrogen, $S(O)_2R_a$, $S(O)_2NR_aR_a$, $C(O)NR_aR_a$, $C(O)R_a$, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, or optionally substituted $C_3$-$C_{12}$ cycloalkenyl, or is a monocyclic or polycyclic group selected from the group consisting of optionally substituted $C_3$-$C_{12}$ cycloalkyl, optionally substituted $C_4$-$C_{12}$ cycloalkenyl, optionally substituted 4- to 12-membered heterocyclic, optionally substituted aryl or optionally substituted heteroaryl, each optionally substituted;

Each $R_a$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

Q is $C(R_d)$ or N;

Each $R_i$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$, and $(C=NR_c)R_c$;

$R_5$ and $R_6$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$; alternatively, $R_5$ and $R_6$ can be taken together with the carbon to which they are attached to form a C(O), $C_3$-$C_8$ cycloalkyl, $C_3$-$C_8$ cycloalkenyl or a 3- to 8-membered heterocyclic;

$Z_1$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cS(O)_nR_c$, $N(R_c)(COOR_c)$, $NR_cC(O)C(O)R_c$, $NR_cC(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$; or alternatively, $R_5$ or $R_6$ can be taken together with $Z_1$ to form a $C_3$-$C_{12}$ cycloalkyl, $C_3$-$C_{12}$ cycloalkenyl, 3- to 12-membered heterocyclic, aryl, or heteroaryl, each optionally substituted;

Each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or alternatively, two $R_c$ groups are taken together with the atom which they are attached to form a $C_3$-$C_8$ cycloalkyl, $C_3$-$C_8$ cycloalkenyl, 3- to 8-membered heterocyclic, aryl or heteroaryl, each optionally substituted;

$R_d$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cS(O)_nR_c$, $N(R_c)(COOR_c)$, $NR_cC(O)C(O)R_c$, $NR_cC(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$; alternatively, $R_d$ and D can be taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted 3- to 12-membered heterocyclic, optionally substituted aryl, optionally substituted heteroaryl and n is 0, 1 or 2.

In yet another embodiment, the invention is directed to a compound having the Formula (IIIa):

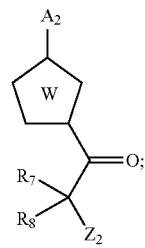

(IIIa)

or a pharmaceutically acceptable salt thereof, prodrug or solvate thereof, wherein:

Ring W is a 5-membered heteroaryl or a 5-membered heterocyclic, wherein each ring carbon atom of said 5-membered heteroaryl is substituted with one $R_d$ and wherein each ring nitrogen atom of said 5-membered heteroaryl is substituted with zero or one $R_d$ when said nitrogen atom is present, and wherein each ring carbon atom of said 5-membered heterocyclic is substituted with one or two $R_d$ and each ring nitrogen atom of said 5-membered heterocyclic is substituted with zero or one $R_d$, when said nitrogen atom or atoms are present;

$A_2$ is $S(O)_2R_a$, $S(O)_2NR_aR_a$, $C(O)NR_aR_a$, $C(O)R_a$, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, or optionally substituted $C_3$-$C_{12}$ cycloalkenyl, or is a monocyclic or polycyclic group selected from the group consisting of optionally substituted $C_3$-$C_{12}$ cycloalkyl, optionally substituted $C_4$-$C_{12}$ cycloalkenyl, optionally substituted 3- to 12-membered heterocyclic, optionally substituted aryl, or optionally substituted heteroaryl;

Each $R_a$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

Each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cS(O)_nR_c$, $N(R_c)(COOR_c)$, $NR_cC(O)C(O)R_c$, $NR_cC(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$; alternatively, two vicinal $R_d$ groups can be taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or yet alternatively, a vicinal $R_d$ and $A_2$ can be taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted 3- to 12-membered heterocyclic, optionally substituted aryl, optionally substituted heteroaryl;

$R_7$ and $R_8$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$, wherein at least one of $R_7$ and $R_8$ is not hydrogen, and further wherein when one of $R_7$ and $R_8$ is hydrogen, the other of $R_7$ and $R_8$ is not methyl; alternatively, $R_7$ and $R_8$ can be taken together with the carbon atom to which they are attached to form C(O), $C_3$-$C_8$ cycloalkyl, $C_3$-$C_8$ cycloalkenyl or a 3- to 8-membered heterocyclic; or yet alternatively, $R_7$ and $R_d$ can be taken together to form a fused monocyclic group selected from the group consisting of $C_5$-$C_{12}$ cycloalkyl, $C_5$-$C_{12}$ cycloalkenyl, 5- to 12-membered heterocyclic, $C_5$-$C_{12}$ aryl, and 5- to 12-membered heteroaryl, each substituted with $R_8$ and $Z_2$, and optionally further substituted;

$Z_2$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$; or further alternatively, $R_7$ or $R_8$ can be taken together with $Z_2$ form a $C_3$-$C_{12}$ cycloalkyl, $C_3$-$C_{12}$ cycloalkenyl, 3- to 12-membered heterocyclic, aryl, and heteroaryl, each optionally substituted;

Each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; alternatively, two $R_c$ groups are taken together with the atom which they are attached to form a $C_3$-$C_8$ cycloalkyl, $C_3$-$C_8$ cycloalkenyl, 3- to 8-membered heterocyclic, aryl or heteroaryl, each optionally substituted; and n is 0, 1 or 2.

In yet another embodiment, the invention is directed to a compound having the Formula (IVa):

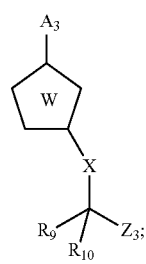

(IVa)

or a pharmaceutically acceptable salt, prodrug or solvate thereof, wherein:

Ring W is a 5-membered heteroaryl or a 5-membered heterocyclic, wherein each ring carbon atom of said 5-membered heteroaryl is substituted with one $R_d$ and wherein each ring nitrogen atom of said 5-membered heteroaryl is substituted with zero or one $R_d$ when said nitrogen atom is present, and wherein each ring carbon atom of said 5-membered heterocyclic is substituted with one or two $R_d$ and each ring nitrogen atom of said 5-membered heterocyclic is substituted with zero or one $R_d$, when said nitrogen atom or atoms are present;

X is selected from the group consisting of $C(R_f)_2$, $C(R_g)=C(R_g)$, S, S(O), $S(O)_2$, and $B(OR_g)$;

$R_f$ is halo;

Each $R_g$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

$A_3$ is $S(O)_2R_a$, $S(O)_2NR_aR_a$, $C(O)NR_aR_a$, $C(O)R_a$, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, or optionally substituted $C_3$-$C_{12}$ cycloalkenyl, or is a monocyclic or polycyclic group selected from the group consisting of optionally substituted $C_3$-$C_{12}$ cycloalkyl, optionally substituted $C_4$-$C_{12}$ cycloalkenyl, optionally substituted 3- to 12-membered heterocyclic, optionally substituted aryl, or optionally substituted heteroaryl;

Each $R_a$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

Each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$; alternatively, two vicinal $R_d$ groups can be taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or yet alternatively, a vicinal $R_d$ and $A_3$ can be taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted 3- to 12-membered heterocyclic, optionally substituted aryl, optionally substituted heteroaryl;

$R_9$ and $R_{10}$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$; alternatively, $R_9$ and $R_{10}$ can be taken together with the carbon atom to which they are attached to form a $C(O)$, $C_3$-$C_8$ cycloalkyl, $C_3$-$C_8$ cycloalkenyl or a 3- to 8-membered heterocyclic; or yet alternatively, $R_9$ and $R_d$ can be taken together to form a fused monocyclic group selected from the group consisting of $C_5$-$C_{12}$ cycloalkyl, $C_5$-$C_{12}$ cycloalkenyl, 5- to 12-membered heterocyclic, $C_5$-$C_{12}$ aryl, and 5- to 12-membered heteroaryl, each substituted with $R_{10}$ and $Z_3$, and optionally further substituted;

$Z_3$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cS(O)_nR_c$, $N(R_c)(COOR_c)$, $NR_cC(O)C(O)R_c$, $NR_cC(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$; or alternatively, $R_9$ or $R_{10}$ can be taken together with $Z_3$ form a $C_3$-$C_{12}$ cycloalkyl, $C_3$-$C_{12}$ cycloalkenyl, 3- to 12-membered heterocyclic, aryl, and heteroaryl, each optionally substituted;

Each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; alternatively, two $R_c$ groups are taken together with the atom which they are attached to form a $C_3$-$C_8$ cycloalkyl, $C_3$-$C_8$ cycloalkenyl, 3- to 8-membered heterocyclic, aryl or heteroaryl, each optionally substituted; and n is 0, 1 or 2.

In a further embodiment, the invention is directed to a compound having the Formula (Va):

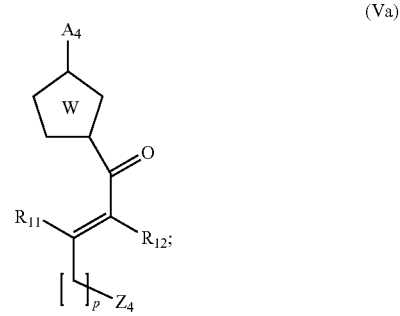

(Va)

or a pharmaceutically acceptable salt, prodrug or solvate thereof, wherein:

Ring W is a 5-membered heteroaryl or a 5-membered heterocyclic, wherein each ring carbon atom of said 5-membered heteroaryl is substituted with one $R_d$ and wherein each ring nitrogen atom of said 5-membered heteroaryl is substituted with zero or one $R_d$ when said nitrogen atom is present, and wherein each ring carbon atom of said 5-membered heterocyclic is substituted with one or two $R_d$ and each ring nitrogen atom of said 5-membered heterocyclic is substituted with zero or one $R_d$, when said nitrogen atom or atoms are present;

$A_4$ is $S(O)_2R_a$, $S(O)_2NR_aR_a$, $C(O)NR_aR_a$, $C(O)R_a$, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, or optionally substituted $C_3$-$C_{12}$ cycloalkenyl, or is a monocyclic or polycyclic group selected from the group consisting of optionally substituted $C_3$-$C_{12}$ cycloalkyl, optionally substituted $C_4$-$C_{12}$ cycloalkenyl, optionally substituted 3- to 12-membered heterocyclic, optionally substituted aryl, or optionally substituted heteroaryl;

Each $R_a$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

Each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, $CN$, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$; alternatively, two vicinal $R_d$ groups can be taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or yet alternatively, a vicinal $R_d$ and $A_4$ can be taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted 3- to 12-membered heterocyclic, optionally substituted aryl, optionally substituted heteroaryl;

$R_{11}$ and $R_{12}$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, $CN$, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$; or alternatively, $R_{11}$ and $R_{12}$ are taken together with the atoms to which they are attached to form an optionally substituted $C_3$-$C_{12}$ cycloalkenyl, optionally substituted heterocyclic, optionally substituted aryl, optionally substituted heteroaryl; or alternatively $R_{12}$ and $R_d$ can be taken together to form a fused monocyclic group selected from the group consisting of $C_5$-$C_{12}$ cycloalkyl, $C_5$-$C_{12}$ cycloalkenyl, 5- to 12-membered heterocyclic, $C_5$-$C_{12}$ aryl, and 5- to 12-membered heteroaryl, each optionally substituted;

$Z_4$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, $CN$, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$; or alternatively, $Z_4$ and $R_{11}$ are taken together to form $C_3$-$C_{12}$ cycloalkyl, $C_3$-$C_{12}$ cycloalkenyl, 3- to 12-membered heterocyclic, aryl, and heteroaryl, each optionally substituted; or yet alternatively, $Z_4$ and $R_{12}$ are taken together to form an optionally substituted $C_3$-$C_{12}$ cycloalkenyl, optionally substituted heterocyclic, optionally substituted aryl, optionally substituted heteroaryl;

Each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; alternatively, two $R_c$ groups are taken together with the atom which they are attached to form a $C_3$-$C_8$ cycloalkyl, $C_3$-$C_8$ cycloalkenyl, 3- to 8-membered heterocyclic, aryl or heteroaryl, each optionally substituted;

n is 0, 1 or 2; and p is 0, 1 or 2.

In yet a further embodiment, the invention encompasses a compound having the Formula (VIa):

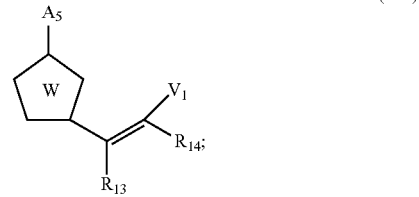

(VIa)

or a pharmaceutically acceptable salt, prodrug or solvate thereof, wherein:

Ring W is a 5-membered heteroaryl or a 5-membered heterocyclic, wherein each ring carbon atom of said 5-membered heteroaryl is substituted with one $R_d$ and wherein each ring nitrogen atom of said 5-membered heteroaryl is substituted with zero or one $R_d$ when said nitrogen atom or atoms are present, and wherein each ring carbon atom of said 5-membered heterocyclic is substituted with one or two $R_d$ and each ring nitrogen atom of said 5-membered heterocyclic is substituted with zero or one $R_d$, when said nitrogen atom or atoms are present;

$A_5$ is $S(O)_2R_a$, $S(O)_2NR_aR_a$, $C(O)NR_aR_a$, $C(O)R_a$, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, or optionally substituted $C_3$-$C_{12}$ cycloalkenyl, or is a monocyclic or polycyclic group selected from the group consisting of optionally substituted $C_3$-$C_{12}$ cycloalkyl, optionally substituted $C_4$-$C_{12}$ cycloalkenyl, optionally substituted 3- to 12-membered heterocyclic, optionally substituted aryl, or optionally substituted heteroaryl;

Each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_aR_c$, $S(O)_nR_c$, $S(O)_aNR_cR_c$, $OC(O)OR_c$ and $(C{=}NR_c)R_c$; alternatively, two vicinal $R_d$ groups can be taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or yet alternatively, a vicinal $R_d$ and $A_5$ can be taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted 3- to 12-membered heterocyclic, optionally substituted aryl, optionally substituted heteroaryl;

Each $R_a$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

$R_{13}$ and $R_{14}$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C{=}NR_c)R_c$; or alternatively, $R_{13}$ and an $R_d$ group can be taken together to form a fused monocyclic group selected from the group consisting of $C_5$-$C_{12}$ cycloalkyl, $C_5$-$C_{12}$ cycloalkenyl, 5- to 12-membered heterocyclic, $C_5$-$C_{12}$ aryl, and 5-12 membered heteroaryl;

$V_1$ is selected from the group consisting of CN, $NO_2$, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C{=}NR_c)R_c$;

Each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; alternatively, two $R_c$ groups are taken together with the atom which they are attached to form a $C_3$-$C_8$ cycloalkyl, $C_3$-$C_8$ cycloalkenyl, 3- to 8-membered heterocyclic, aryl or heteroaryl, each optionally substituted; and n is 0, 1 or 2.

In yet an additional embodiment, the compound has the Formula (VId):

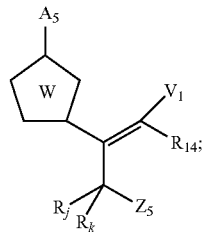

(VId)

or a pharmaceutically acceptable salt, prodrug or solvate thereof, wherein:

Ring W is a 5-membered heteroaryl or a 5-membered heterocyclic, wherein each ring carbon atom of said 5-membered heteroaryl is substituted with one $R_d$ and wherein each ring nitrogen atom of said 5-membered heteroaryl is substituted with zero or one $R_d$ when said nitrogen atom or atoms are present, and wherein each ring carbon atom of said 5-membered heterocyclic is substituted with one or two $R_d$ and each ring nitrogen atom of said 5-membered heterocyclic is substituted with zero or one $R_d$, when said nitrogen atom or atoms are present;

$A_5$ is $S(O)_2R_a$, $S(O)_2NR_aR_a$, $C(O)NR_aR_a$, $C(O)R_a$, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, or optionally substituted $C_3$-$C_{12}$ cycloalkenyl, or is a monocyclic or polycyclic group selected from the group consisting of optionally substituted $C_3$-$C_{12}$ cycloalkyl, optionally substituted $C_4$-$C_{12}$ cycloalkenyl, optionally substituted 3- to 12-membered heterocyclic, optionally substituted aryl, or optionally substituted heteroaryl;

Each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_aR_c$, $S(O)_nR_c$, $S(O)_nNR_cR_c$, $OC(O)OR_c$ and $(C{=}NR_c)R_c$; alternatively, two vicinal $R_d$ groups can be taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or yet alternatively, a vicinal $R_d$ and $A_5$ can be taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted 3- to 12-membered heterocyclic, optionally substituted aryl, optionally substituted heteroaryl;

Each $R_a$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

$R_{14}$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)_nNR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$;

$R_j$ and $R_k$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)_nNR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$; alternatively, $R_j$ and $R_k$ can be taken together with the carbon atom to which they are attached to form a $C(O)$, $C_3$-$C_8$ cycloalkyl, $C_3$-$C_8$ cycloalkenyl or a 3- to 8-membered heterocyclic, each optionally substituted; or alternatively, N and $R_d$ can be taken together to form a fused monocyclic group selected from the group consisting of $C_5$-$C_{12}$ cycloalkyl, $C_5$-$C_{12}$ cycloalkenyl, 5- to 12-membered heterocyclic, $C_5$-$C_{12}$ aryl, and 5- to 12-membered heteroaryl, each optionally substituted; and $Z_5$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$; or alternatively, $V_1$ and $Z_5$ are taken together with the atoms to which they are attached to form optionally substituted $C_4$-$C_{12}$ cycloalkenyl, optionally substituted heterocyclic, optionally substituted aryl, optionally substituted heteroaryl; or yet alternatively, $R_j$ or $R_k$ can be taken together with $Z_5$ form a $C_3$-$C_{12}$ cycloalkyl, $C_3$-$C_{12}$ cycloalkenyl, 3- to 12-membered heterocyclic, aryl, and heteroaryl, each optionally substituted; or yet alternatively, $R_k$ can be taken together with $Z_5$ to form a $C_4$-$C_{12}$ cycloalkenyl, 4- to 12-membered heterocyclic, aryl and heteroaryl, each optionally substituted;

$V_1$ is selected from the group consisting of CN, $NO_2$, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$;

Each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; alternatively, two $R_c$ groups are taken together with the atom which they are attached to form a $C_3$-$C_8$ cycloalkyl, $C_3$-$C_8$ cycloalkenyl, 3- to 8-membered heterocyclic, aryl or heteroaryl, each optionally substituted; and n is 0, 1 or 2.

In an additional embodiment, the invention is directed to a compound having the Formula (VII):

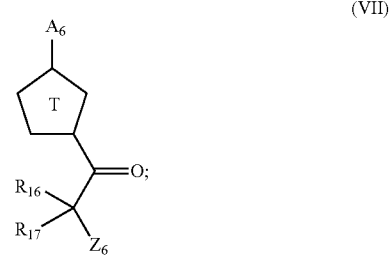

(VII)

or a pharmaceutically acceptable, salt or prodrug thereof;

Ring T is a ring selected from the group consisting of:

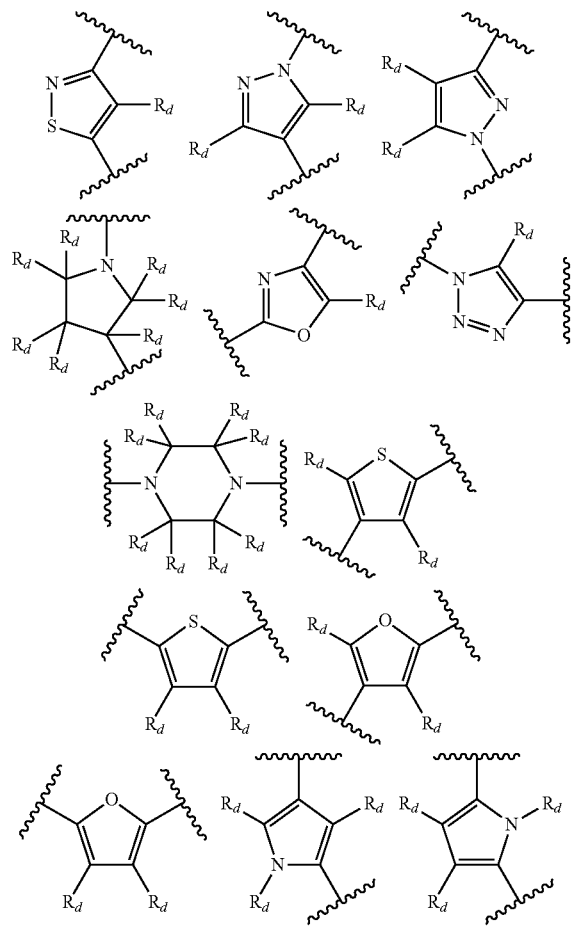

$A_6$ is $S(O)_2R_a$, $S(O)_2NR_aR_a$, $C(O)NR_aR_a$, $C(O)R_a$, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, or optionally substituted $C_3$-$C_{12}$ cycloalkenyl, or is a monocyclic or polycyclic group selected from the group consisting of optionally substituted $C_4$-$C_{12}$ cycloalkyl, optionally substituted $C_4$-$C_{12}$ cycloalkenyl, optionally substituted 4- to 12-membered heterocyclic, optionally substituted aryl, optionally substituted heteroaryl;

Each $R_a$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

Each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_aR_c$, $S(O)_nR_c$, $S(O)_aNR_cR_c$, $OC(O)OR_c$ and $(C=NR_c)R_c$; alternatively, two vicinal $R_d$ groups can be taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or yet alternatively, a vicinal $R_d$ and $A_6$ can be taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted 3- to 12-membered heterocyclic, optionally substituted aryl, optionally substituted heteroaryl;

$R_{16}$ and $R_{17}$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$; alternatively, $R_{16}$ and $R_{17}$ can be taken together with the carbon atom to which they are attached to form a C(O), $C_3$-$C_8$ cycloalkyl, $C_3$-$C_8$ cycloalkenyl or a 3- to 8-membered heterocyclic; or yet alternatively, $R_{16}$ or $R_{17}$ can be taken together with $R_d$ to form a fused monocyclic group selected from the group consisting of $C_5$-$C_{12}$ cycloalkyl, $C_5$-$C_{12}$ cycloalkenyl, 5- to 12-membered heterocyclic, $C_5$-$C_{12}$ aryl, and 5- to 12-membered heteroaryl, each substituted with $R_{17}$ and $Z_6$, and optionally further substituted;

$Z_6$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$; or further alternatively, $R_{16}$ or $R_{17}$ can be taken together with $Z_6$ form a $C_3$-$C_{12}$ cycloalkyl, $C_3$-$C_{12}$ cycloalkenyl, 3- to 12-membered heterocyclic, aryl, and heteroaryl, each optionally substituted;

Each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; alternatively, two $R_c$ groups are taken together with the atom which they are attached to form a $C_3$-$C_8$ cycloalkyl, $C_3$-$C_8$ cycloalkenyl, 3- to 8-membered heterocyclic, aryl or heteroaryl, each optionally substituted; and n is 0, 1 or 2.

In an additional embodiment, the invention is directed to a compound having the Formula (VIIIa):

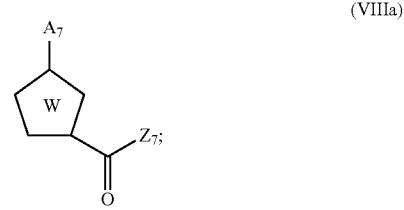

(VIIIa)

or a pharmaceutically acceptable salt, prodrug or solvate thereof, wherein:

Ring W is a 5-membered heteroaryl or a 5-membered heterocyclic, wherein each ring carbon atom of said 5-membered heteroaryl is substituted with one $R_d$ and wherein each ring nitrogen atom of said 5-membered heteroaryl is substituted with zero or one $R_d$ when said nitrogen atom is present, and wherein each ring carbon atom of said 5-membered heterocyclic is substituted with one or two $R_d$ and each ring nitrogen atom of said 5-membered heterocyclic is substituted with zero or one $R_d$, when said nitrogen atom or atoms are present;

$A_7$ is $S(O)_2R_a$, $S(O)_2NR_aR_a$, $C(O)NR_aR_a$, $C(O)R_a$, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, or optionally substituted $C_3$-$C_{12}$ cycloalkenyl, or is a monocyclic or polycyclic group selected from the group consisting of optionally substituted $C_3$-$C_{12}$ cycloalkyl, optionally substituted $C_4$-$C_{12}$ cycloalkenyl, optionally substituted 3- to 12-membered heterocyclic, optionally substituted aryl, or optionally substituted heteroaryl;

Each $R_a$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

Each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cS(O)_nR_c$, $N(R_c)(COOR_c)$, $NR_cC(O)C(O)R_c$, $NR_cC(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$; alternatively, two vicinal $R_d$ groups can be taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or yet alternatively, a vicinal $R_d$ and $A_7$ can be taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted 3- to 12-membered heterocyclic, optionally substituted aryl, optionally substituted heteroaryl;

$Z_7$ is selected from the group consisting of optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;

Each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; alternatively, two $R_c$ groups are taken together with the atom which they are attached to form a $C_3$-$C_8$ cycloalkyl, $C_3$-$C_8$ cycloalkenyl, 3- to 8-membered heterocyclic, aryl or heteroaryl, each optionally substituted; and n is 0, 1 or 2.

In another embodiment, the invention is directed to a compound of Formula (IX):

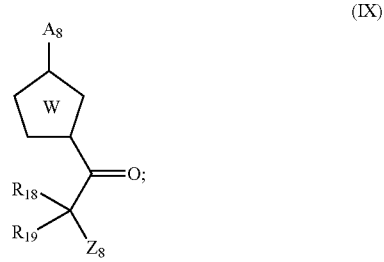

(IX)

or a pharmaceutically acceptable salt thereof, prodrug or solvate thereof, wherein:

Ring W is a 5-membered heteroaryl or a 5-membered heterocyclic, wherein each ring carbon atom of said 5-membered heteroaryl is substituted with one $R_d$ and wherein each ring nitrogen atom of said 5-membered heteroaryl is substituted with zero or one $R_d$ when said nitrogen atom is present, and wherein each ring carbon atom of said 5-membered heterocyclic is substituted with one or two $R_d$ and each ring nitrogen atom of said 5-membered heterocyclic is substituted with zero or one $R_d$, when said nitrogen atom or atoms are present;

$A_8$ is $S(O)_2R_a$, $S(O)_2NR_aR_a$, $C(O)NR_aR_a$, $C(O)R_a$, optionally substituted $C_1$-$C_{10}$ alkyl, optionally substituted $C_2$-$C_{10}$ alkenyl, and optionally substituted $C_2$-$C_{10}$ alkynyl;

Each $R_a$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

Each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, $CN$, $C(O)R_c$, $C(O)C(O)R_c$, $C(O)NR_cR_c$, $NR_cS(O)_nR_c$, $N(R_c)(COOR_c)$, $NR_cC(O)C(O)R_c$, $NR_cC(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$; alternatively, two vicinal $R_d$ groups can be taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or yet alternatively, a vicinal $R_d$ and $A_2$ can be taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted 3- to 12-membered heterocyclic, optionally substituted aryl, optionally substituted heteroaryl;

$R_{18}$ and $R_{19}$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, $CN$, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$; alternatively, $R_7$ and $R_8$ can be taken together with the carbon atom to which they are attached to form $C(O)$, $C_3$-$C_8$ cycloalkyl, $C_3$-$C_8$ cycloalkenyl or a 3- to 8-membered heterocyclic; or yet alternatively, $R_7$ and $R_d$ can be taken together to form a fused monocyclic group selected from the group consisting of $C_5$-$C_{12}$ cycloalkyl, $C_5$-$C_{12}$ cycloalkenyl, 5- to 12-membered heterocyclic, $C_5$-$C_{12}$ aryl, and 5- to 12-membered heteroaryl, each substituted with $R_8$ and $Z_2$, and optionally further substituted;

$Z_8$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, $CN$, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$; or further alternatively, $R_7$ or $R_8$ can be taken together with $Z_2$ form a $C_3$-$C_{12}$ cycloalkyl, $C_3$-$C_{12}$ cycloalkenyl, 3- to 12-membered heterocyclic, aryl, and heteroaryl, each optionally substituted;

Each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; alternatively, two $R_c$ groups are taken together with the atom which they are attached to form a $C_3$-$C_8$ cycloalkyl, $C_3$-$C_8$ cycloalkenyl, 3- to 8-membered heterocyclic, aryl or heteroaryl, each optionally substituted; and n is 0, 1 or 2.

In one aspect, the pharmaceutical composition comprises a pharmaceutically acceptable carrier or excipient and a compound of Formula (Ia), (II), (IIIa), (IVa), (Va), (VIa), (VId), (VII), (VIIIa), or (IX), or a pharmaceutically acceptable salt, prodrug or solvate thereof.

The invention also includes a method of treating a patient suffering from a condition associated with a dysfunction in proteostasis comprising administering to said patient an effective amount of a compound of Formula (Ia), (II), (IIIa), (IVa), (Va), (VIa), (VId), (VII), (VIIIa), or (IX), or a pharmaceutically acceptable salt, prodrug or solvate thereof.

The invention further includes a method of treating a patient suffering from a condition associated with a dysfunction in proteostasis comprising administering to said patient a pharmaceutical composition comprising a pharmaceutically acceptable carrier or excipient and an effective amount of a compound having the Formula (Ia), (II), (IIIa), (IVa), (Va), (VIa), (VId), (VII), (VIIIa), or (IX), or a pharmaceutically acceptable salt, prodrug or solvate thereof.

The invention additionally includes a method of treating a patient suffering from a condition associated with a dysfunction in proteostasis comprising administering to said patient an effective amount of a compound of Formula (IIId):

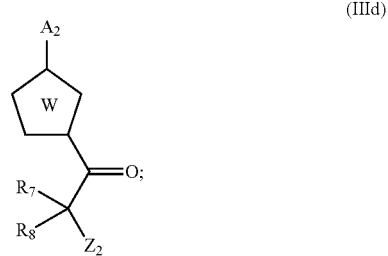

(IIId)

or a pharmaceutically acceptable salt thereof, prodrug or solvate thereof, wherein:

Ring W is a 5-membered heteroaryl or a 5-membered heterocyclic, wherein each ring carbon atom of said 5-membered heteroaryl is substituted with one $R_d$ and wherein each ring nitrogen atom of said 5-membered heteroaryl is substituted with zero or one $R_d$ when said nitrogen atom is present, and wherein each ring carbon atom of said 5-membered heterocyclic is substituted with one or two $R_d$ and each ring nitrogen atom of said 5-membered heterocyclic is substituted with zero or one $R_d$, when said nitrogen atom or atoms are present;

$A_2$ is $S(O)_2R_a$, $S(O)_2NR_aR_a$, $C(O)NR_aR_a$, $C(O)R_a$, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, or optionally substituted $C_3$-$C_{12}$ cycloalkenyl, or is a monocyclic or polycyclic group selected from the group consisting of optionally substituted $C_3$-$C_{12}$ cycloalkyl, optionally substituted $C_4$-$C_{12}$ cycloalkenyl, optionally substituted 3- to 12-membered heterocyclic, optionally substituted aryl, or optionally substituted heteroaryl;

Each $R_a$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

Each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cS(O)_nR_c$, $N(R_c)(COOR_c)$, $NR_cC(O)C(O)R_c$, $NR_cC(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$; alternatively, two vicinal $R_d$ groups can be taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or yet alternatively, a vicinal $R_d$ and $A_2$ can be taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted 3- to 12-membered heterocyclic, optionally substituted aryl, optionally substituted heteroaryl;

$R_7$ and $R_8$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$, wherein at least one of $R_7$ and $R_8$ is not hydrogen; alternatively, $R_7$ and $R_8$ can be taken together with the carbon atom to which they are attached to form $C(O)$, $C_3$-$C_8$ cycloalkyl, $C_3$-$C_8$ cycloalkenyl or a 3- to 8-membered heterocyclic; or yet alternatively, $R_7$ and $R_d$ can be taken together to form a fused monocyclic group selected from the group consisting of $C_5$-$C_{12}$ cycloalkyl, $C_5$-$C_{12}$ cycloalkenyl, 5- to 12-membered heterocyclic, $C_5$-$C_{12}$ aryl, and 5- to 12-membered heteroaryl, each substituted with $R_8$ and $Z_2$, and optionally further substituted;

$Z_2$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$; or further alternatively, $R_7$ or $R_8$ can be taken together with $Z_2$ form a $C_3$-$C_{12}$ cycloalkyl, $C_3$-$C_{12}$ cycloalkenyl, 3- to 12-membered heterocyclic, aryl, and heteroaryl, each optionally substituted;

Each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; alternatively, two $R_c$ groups are taken together with the atom which they are attached to form a $C_3$-$C_8$ cycloalkyl, $C_3$-$C_8$ cycloalkenyl, 3- to 8-membered heterocyclic, aryl or heteroaryl, each optionally substituted; and n is 0, 1 or 2.

In an additional aspect, the pharmaceutical composition comprises a pharmaceutically acceptable carrier or excipient and a compound of Formula (IIId), or a pharmaceutically acceptable salt, prodrug or solvate thereof.

In yet another embodiment, the invention encompasses a method of treating cancer or a tumor in a subject in need thereof comprising administering to said subject an effective amount of a compound of Formulae Formula (Ia), (II), (IIIa), (IIId), (IVa), (Va), (VIa), (VId), (VII), (VIIIa), or (IX) or a pharmaceutically acceptable salt, solvate, clathrate or prodrug thereof.

In an additional aspect, the invention is directed to a pharmaceutical composition comprising:

a pharmaceutically acceptable carrier or excipient;

an effective amount of a compound having the Formula (Ia), (II), (IIIa), (IIId), (IVa), (Va), (VIa), (VId), (VII), (VIIIa), or (IX), or a pharmaceutically acceptable salt, solvate, or prodrug of any of thereof; and an effective amount of a second agent selected from the group consisting of a proteostasis regulator and a pharmacologic chaperone.

DETAILED DESCRIPTION OF THE INVENTION

A description of preferred embodiments of the invention follows.

As used herein, the words "a" and "an" are meant to include one or more unless otherwise specified. For example, the term "an atom" encompasses both a single atom and more than one atom.

As discussed above, the present invention is directed to compounds of Formulae (Ia-Ie), (II), (IIIc-IIIc), (IVa-IVc), (Va-Vb), (VIa-Vie), (VII), (VIIIa-VIIIc), and (IX), pharmaceutical compositions thereof and methods of use thereof in the treatment of conditions associated with a dysfunction in proteostasis and in the treatment of cancer or tumor. The invention also encompasses pharmaceutical compositions comprising compounds of Formula (IIId) and methods of use thereof in the treatment of conditions associated with a dysfunction in proteostasis and methods of treating cancer or tumor comprising administering a compound of Formula (IIId).

In some embodiments, the compound has the Formula (Ia). In additional embodiments, the compound has the Formula (Ia), wherein Ring W is a heteroaryl. In yet additional embodiments, the compound has the Formula (Ia), wherein Ring W is a heteroaryl containing one or more ring nitrogen atoms. In yet another aspect, the compound has the Formula (Ia), wherein Ring W is a thienyl or a furanyl.

In certain aspects, the compound has the Formula (Ia), wherein Y is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $OR_c$, $SR_c$, $C(O)OR_c$, $NO_2$, $CN$, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$, $(C=NR_c)R_c$, optionally substituted heterocyclic and optionally substituted heteroaryl, wherein said heterocyclic is and heteroaryl are C-attached to the carbon atom bonded to $R_3$ and $R_4$; or alternatively, $R_3$ or $R_4$ can be taken together with Y to form a $C_3$-$C_{12}$ cycloalkyl, $C_3$-$C_{12}$ cycloalkenyl, 3- to 12-membered heterocyclic, aryl, or heteroaryl, each optionally substituted.

In certain embodiments, the compound has the Formula (Ia), wherein Y is selected from the group consisting of optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, $OR_c$, $SR_c$ and $C(O)NR_cR_c$, wherein said heterocyclic is C-attached to the carbon atom which is bonded to $R_3$ and $R_4$.

In some embodiments, the compound has the Formula (Ia), wherein Y is selected from the group consisting of optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, $OR_c$, $SR_c$ and $C(O)NR_cR_c$, wherein said heterocyclic and heteroaryl are C-attached to the carbon atom which is bonded to $R_3$ and $R_4$.

In yet another aspect, the compound has the Formula (Ia), wherein Ring W is substituted by at least two $R_d$ groups at adjacent ring carbon atoms and wherein the two $R_d$ groups are taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl.

In certain additional aspects, the compound has the Formula (Ia) but is not selected from the group consisting of:

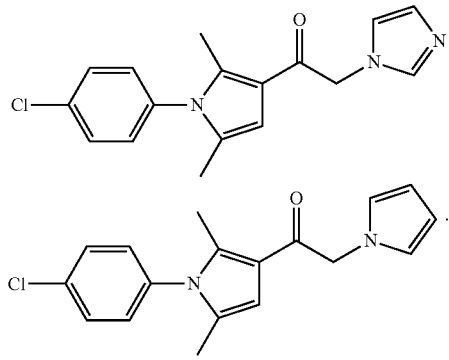

In a further embodiment, the compound has the Formula (Ia), wherein $R_3$ and an $R_d$ group are taken together to form a fused monocyclic group selected from the group consisting of $C_5$-$C_{12}$ cycloalkyl, $C_5$-$C_{12}$ cycloalkenyl, 3- to 12-membered heterocyclic, aryl, and heteroaryl, each substituted with $R_4$ and Y and optionally further substituted. In yet an additional embodiment, $R_3$ and $R_d$ are taken together to form a fused monocyclic group as described above, wherein the compound has the Formula (Ib):

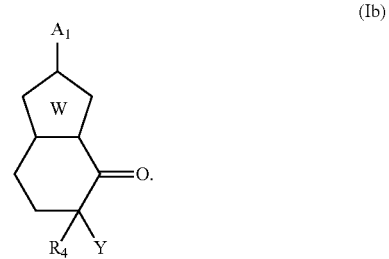

In a further embodiment, $R_3$ and $R_d$ are taken together to form a fused monocyclic group as described above, wherein the compound has the Formula (Ic):

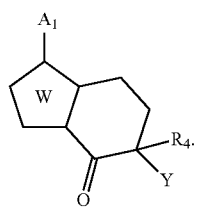

(Ic)

In yet an additional embodiment, the compound has the Formula (Ia), wherein $A_1$ and a vicinal $R_d$ group are taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted 3- to 12-membered heterocyclic, optionally substituted aryl, optionally substituted heteroaryl. In a further aspect, the compound has the Formula (Ia), wherein a vicinal $R_d$ and $A_1$ groups are taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted 3- to 12-membered heterocyclic, optionally substituted aryl, optionally substituted heteroaryl and Ring W is a pyrrolyl. In yet another aspect, $A_1$ and a vicinal $R_d$ group are taken together to form a fused polycyclic group. Non-limiting examples of such compounds wherein Ring W is pyrollyl and wherein $A_1$ and a vicinal $R_d$ group are taken together to form a fused polycyclic group are shown below:

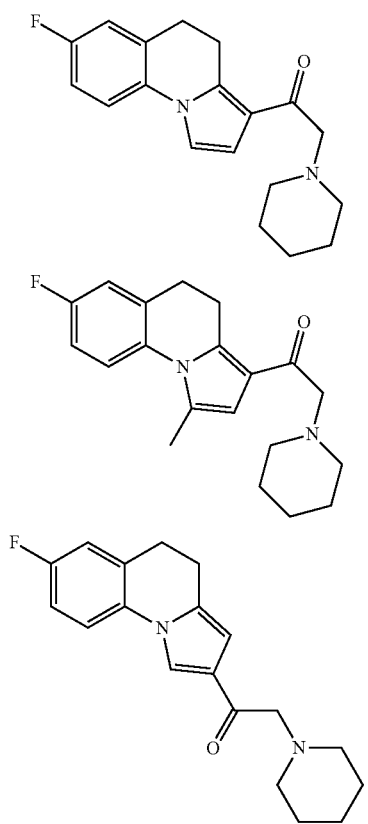

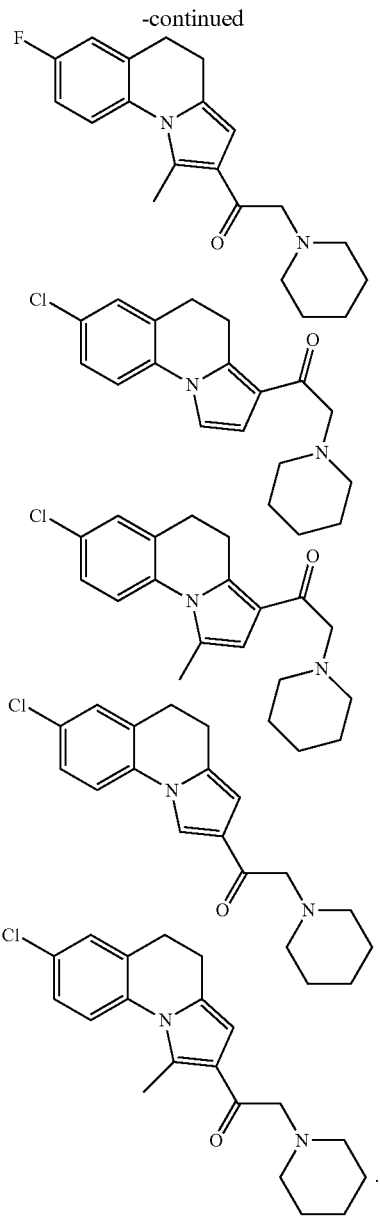

In one aspect, the compound has the Formula (Ia), wherein Ring W is a 5-membered heteroaryl containing one or two nitrogen ring atoms.

In yet an additional embodiment, the compound has the Formula (Ia), wherein Ring W is substituted with two vicinal $R_d$ groups, and wherein the vicinal $R_d$ groups are taken together to form an optionally substituted fused phenyl.

In a further embodiment, the compound of Formula (Ia) has the Formula (Id):

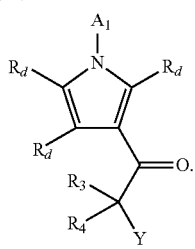

(Id)

In some embodiments, each $R_d$ is independently selected from the group consisting of hydrogen, optionally substituted $C_1$-$C_{10}$ alkyl and optionally substituted $C_3$-$C_{12}$ cycloalkyl. In yet an additional embodiment, the compound has the Formula (Ie):

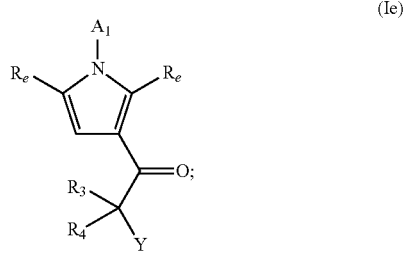

wherein each $R_e$ is independently an optionally substituted $C_1$-$C_4$ alkyl or an optionally substituted $C_3$-$C_{12}$ cycloalkyl. In yet an additional embodiment, each $R_e$ is independently an optionally substituted $C_1$-$C_4$ alkyl or an optionally substituted $C_3$-$C_6$ cycloalkyl. In yet a further embodiment, each $R_e$ is independently an optionally substituted $C_1$-$C_4$ alkyl. In certain additional embodiments, the compound has the Formula (Ie), wherein Y is selected from the group consisting of optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, $OR_c$ and $SR_c$. In yet an additional embodiment, the compound has the Formula (Ie) wherein $A_1$ is optionally substituted phenyl.

Non-limiting examples of compounds of Formula (Ia), (Id) and/or (Ie) are shown in Table 1 below.

TABLE 1

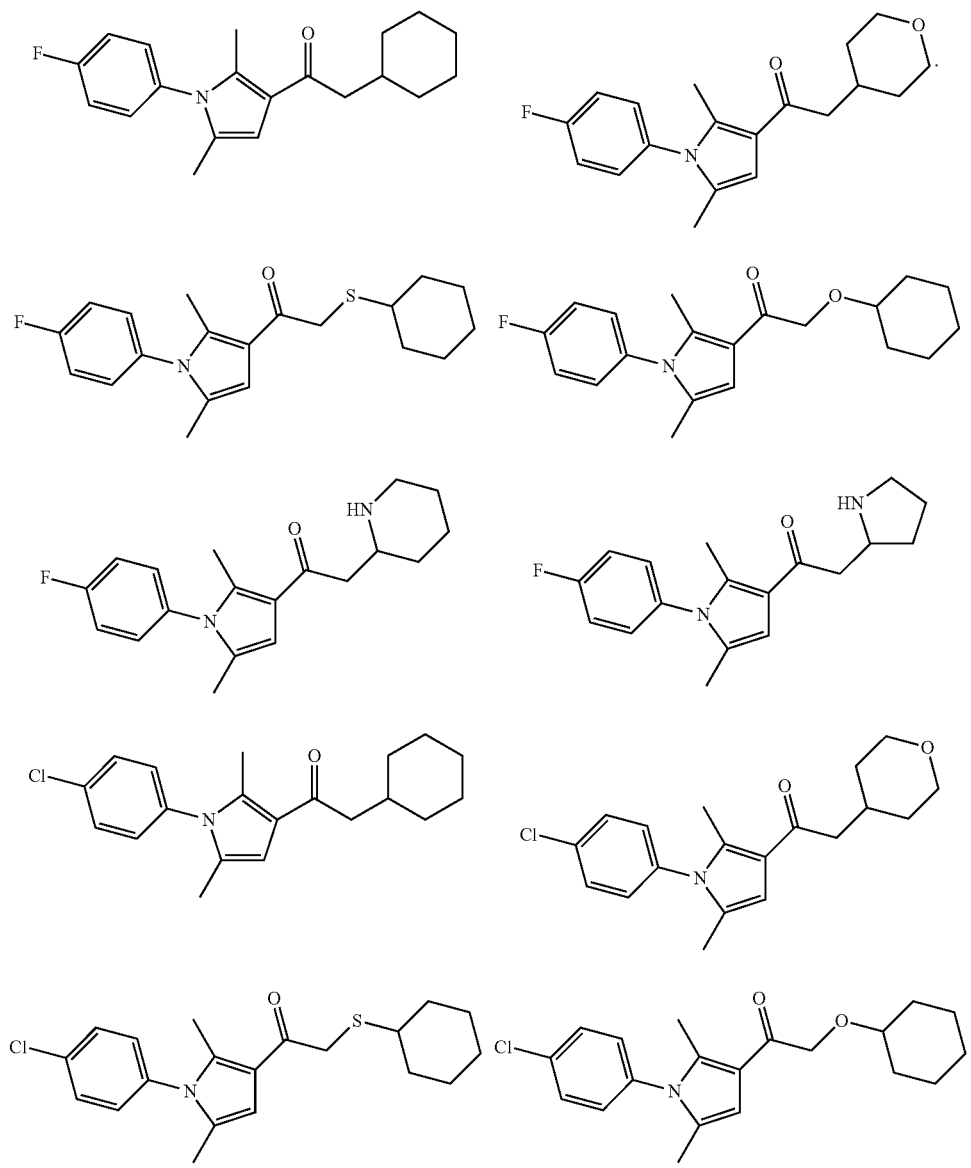

TABLE 1-continued

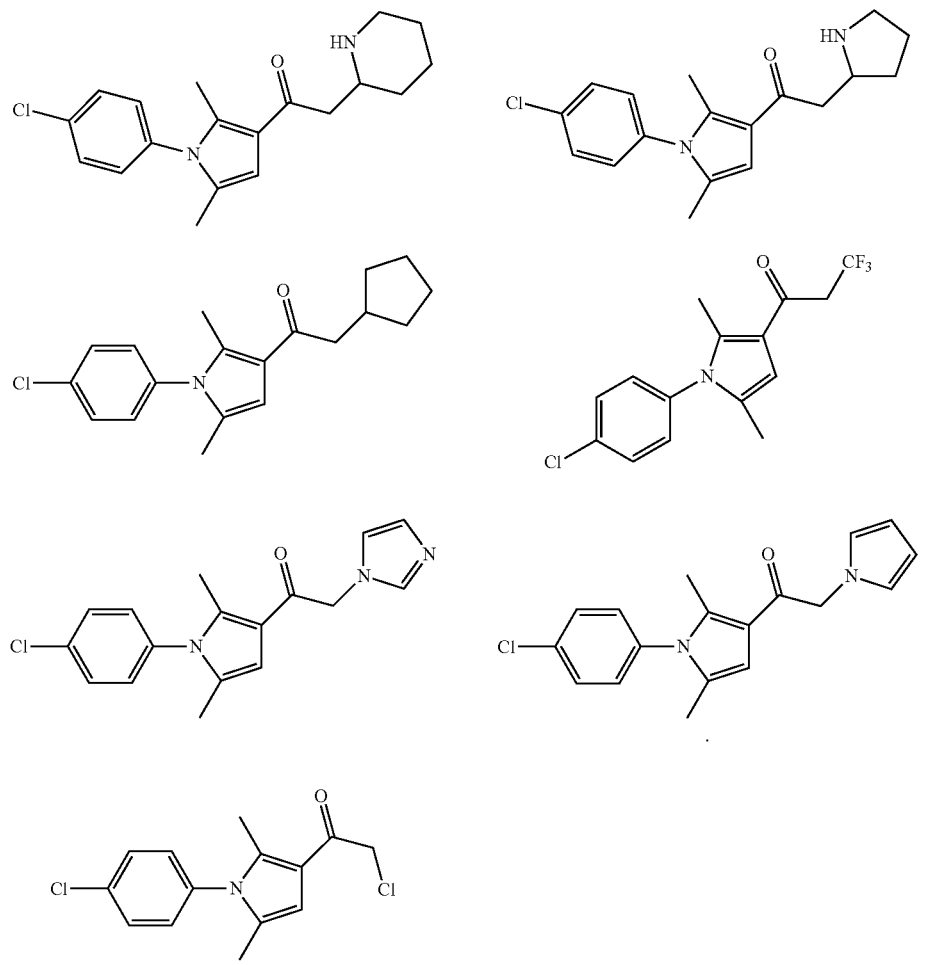

In certain aspects, the compound has the Formula (II), wherein D is selected from the group consisting of $S(O)_2R_a$, $S(O)_2NR_aR_a$, $C(O)NR_aR_a$, $C(O)R_a$, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, or optionally substituted $C_3$-$C_{12}$ cycloalkenyl, or is a monocyclic or polycyclic group selected from the group consisting of optionally substituted $C_3$-$C_{12}$ cycloalkyl, optionally substituted $C_4$-$C_{12}$ cycloalkenyl, optionally substituted 4- to 12-membered heterocyclic, optionally substituted aryl or optionally substituted heteroaryl, each optionally substituted.

In some embodiments, the compound has the Formula (IIIa). In an additional embodiment, the compound has the Formula (IIIa), wherein $R_7$ and $R_8$ are each independently selected from the group consisting of optionally substituted $C_1$-$C_4$ alkyl and halo; or $R_7$ and $R_8$ are taken together with the atom to which they are attached to form an optionally substituted $C_5$-$C_6$ cycloalkyl. In another embodiment, $R_7$ and $R_8$ are each independently selected from the group consisting of optionally substituted methyl and fluoro; or $R_7$ and $R_8$ are taken together with the atom to which they are attached to form an optionally substituted cyclopentyl or an optionally substituted cyclohexyl.

In an additional embodiment, the compound has the Formula (IIIa), wherein $R_7$ and $R_8$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$, wherein at least one of $R_7$ and $R_8$ is not hydrogen, and further wherein when one of $R_7$ and $R_8$ is hydrogen, the other of $R_7$ and $R_8$ is not a $C_1$-$C_4$ alkyl. In an additional embodiment, the compound has the Formula (IIIa), wherein $R_7$ and $R_8$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, CN, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$, wherein at least one of $R_7$ and $R_8$ is not hydrogen, and further wherein when one of $R_7$ and $R_8$ is hydrogen, the other of $R_7$ and $R_8$ is not an optionally substituted $C_1$-$C_4$ alkyl.

In additional embodiments, the compound has the Formula (IIIa), wherein one of $R_7$ and $R_8$ is hydrogen and the other is selected from the group consisting of substituted $C_1$ alkyl, optionally substituted $C_2$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, $CN$, $C(O)R_c$, $C(O)C(O)R_c$, $C(O)NR_cR_c$, $NR_cC(O)R_c$, $NR_cS(O)_nR_c$, $N(R_c)(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$. In certain embodiments, the compound has the Formula (IIIa), wherein one or $R_7$ and $R_8$ is hydrogen and the other is optionally substituted $C_1$-$C_4$ alkyl or halo.

In certain embodiments, $R_7$ and an $R_d$ can be taken together to form a fused monocyclic group selected from the group consisting of $C_5$-$C_{12}$ cycloalkyl, $C_5$-$C_{12}$ cycloalkenyl, 5- to 12-membered heterocyclic, $C_5$-$C_{12}$ aryl, and 5- to 12-membered heteroaryl, each substituted with $R_8$ and $Z_2$, and optionally further substituted. When $R_7$ and an $R_d$ are taken together to form the fused monocyclic group, it is to be understood that $R_8$ can be hydrogen; or in other words, is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_cR_c$, $C(O)OR_c$, $NO_2$, $CN$, $C(O)R_c$, $C(O)C(O)R_c$, $C(O)NR_cR_c$, $NR_cC(O)R_c$, $NR_cS(O)_nR_c$, $N(RO(COOR_c)$, $NR_cC(O)C(O)R_c$, $NR_cC(O)NR_cR_c$, $NR_cS(O)_nNR_cR_c$, $NR_cS(O)_nR_c$, $S(O)_nR_c$, $S(O)_nNR_cR_c$, $OC(O)OR_c$ and $(C=NR_c)R_c$. In some embodiments, $R_7$ and an $R_d$ can be taken together to form a fused monocyclic group selected from the group consisting of $C_5$-$C_{12}$ cycloalkyl, $C_5$-$C_{12}$ cycloalkenyl, 5- to 12-membered heterocyclic, $C_5$-$C_{12}$ aryl, and 5- to 12-membered heteroaryl, each substituted with $R_8$ and $Z_2$, wherein $R_8$ is hydrogen. In additional aspects, $R_7$ and an $R_d$ can be taken together to form a fused monocyclic group selected from the group consisting of $C_5$-$C_{12}$ cycloalkyl, $C_5$-$C_{12}$ cycloalkenyl, 5- to 12-membered heterocyclic, $C_5$-$C_{12}$ aryl, and 5- to 12-membered heteroaryl, each substituted with $R_8$ and $Z_2$, wherein $Z_2$ is $NR_cR_c$.

In an additional embodiment, the compound has the Formula (IIIa), wherein Ring W is a 5-membered nitrogen-containing heteroaryl or a 5-membered nitrogen-containing heterocyclic. In yet an additional embodiment, the compound has the Formula (IIIa), wherein Ring W is a thienyl or a furanyl. In yet an additional embodiment, the compound has the Formula (IIIa), wherein Ring W is a pyrrolyl.

In another embodiment, the compound has the Formula (IIIa) wherein $R_7$ and $R_8$ are taken together with the carbon atom to which they are attached to form $C(O)$.

In certain aspects, the compound of the invention has the Formula (IIIb):

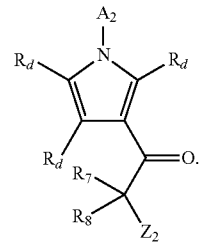

(IIIb)

In yet an additional embodiment, the compound of the invention has the Formula (IIIc):

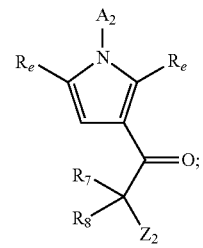

(IIIc)

wherein each $R_e$ is independently an optionally substituted $C_1$-$C_4$ alkyl or an optionally substituted $C_3$-$C_{12}$ cycloalkyl. In one embodiment, the compound has the Formula (Inc), wherein $R_7$ and $R_8$ are taken together with the carbon atom to which they are attached to form $C(O)$. In a further embodiment, the compound has the Formula (IIIc), wherein each $R_e$ is independently an optionally substituted $C_1$-$C_4$ alkyl.

Non-limiting examples of compounds of Formula (IIIa), (IIIb), (IIIc) or (IIId) are selected from the group consisting of the compounds shown in Table 2 below.

TABLE 2

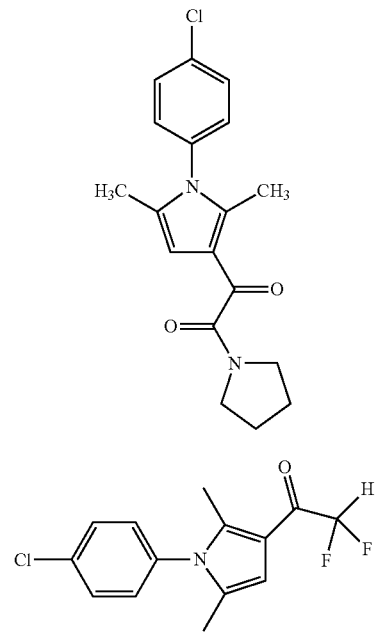

TABLE 2-continued

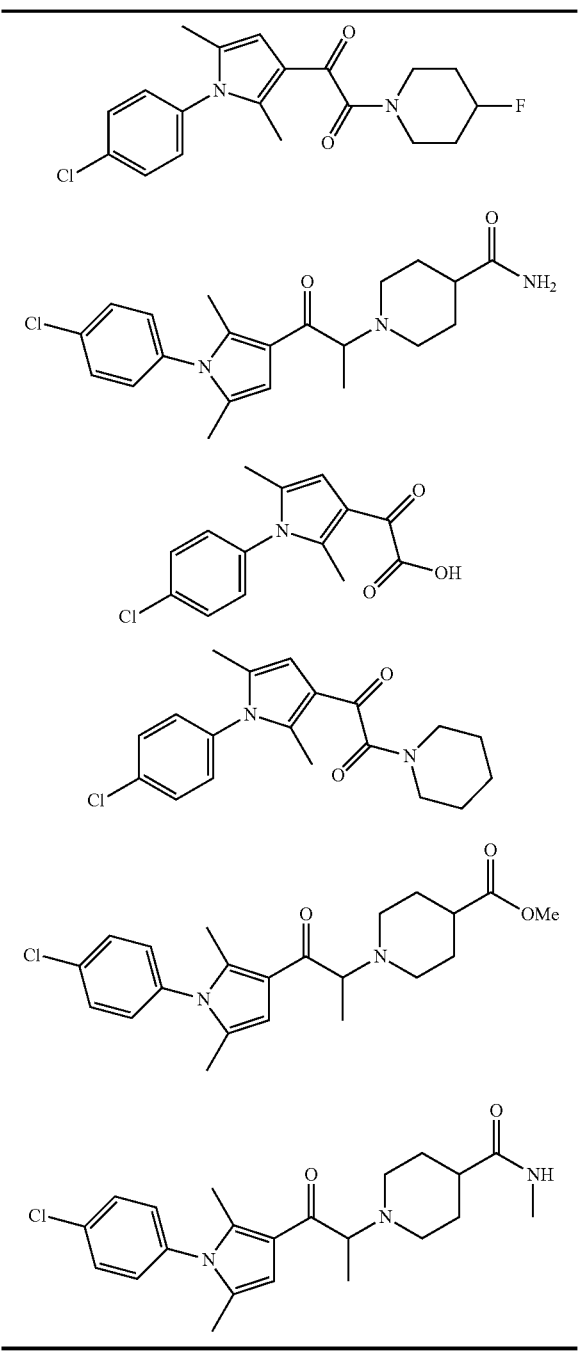

In some embodiments, the compound of the invention has the Formula (IVa). In one embodiment, the compound has the Formula (IVa), wherein Ring W is 5-membered nitrogen-containing heteroaryl or a 5-membered nitrogen-containing heterocyclic. In yet another embodiment, the compound has the Formula (IVa), wherein Ring W is a thienyl or a furanyl. In yet an additional embodiment, the compound has the Formula (IVa), wherein Ring W is a pyrrolyl.

In one embodiment, the compound has the Formula (IVa), wherein X is $C(R_g)=C(R_g)$, S(O) or S(O)$_2$. In certain additional embodiments, the compound has the Formula (VIa), wherein X is S(O) or S(O)$_2$. In yet an additional embodiment, X is CH=CH or $C(CH_3)=C(CH_3)$.

In yet an additional embodiment, the compound of the invention has the Formula (IVb):

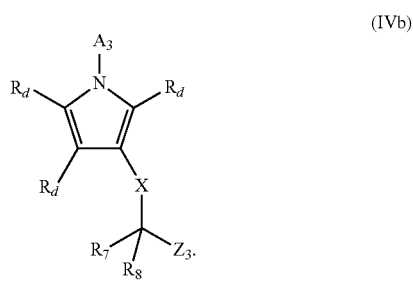

(IVb)

In a further embodiment, the compound has the Formula (IVc):

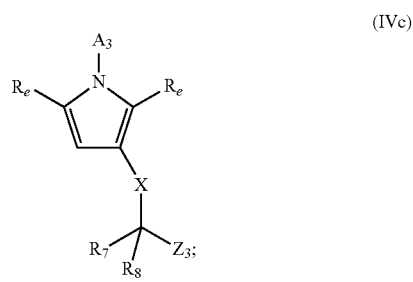

(IVc)

wherein each $R_e$ is independently an optionally substituted $C_1$-$C_4$ alkyl or an optionally substituted $C_3$-$C_{12}$ cycloalkyl. In one embodiment, the compound has the Formula (Va), wherein Ring W is 5-membered nitrogen-containing heteroaryl or a 5-membered nitrogen-containing heterocyclic. In yet another embodiment, the compound has the Formula (Va), wherein Ring W is a thienyl or a furanyl. In yet an additional embodiment, the compound has the Formula (Va), wherein Ring W is a pyrrolyl.

In another embodiment, the compound has the Formula (Vb):

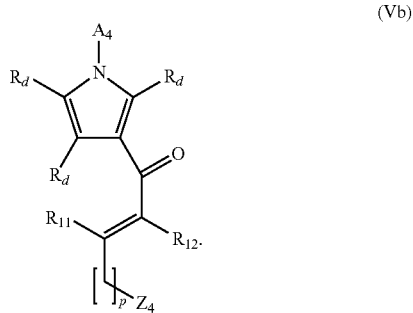

(Vb)

In certain aspects, the compound has the Formula (Vb), wherein $A_4$ is optionally substituted aryl, for example, optionally substituted phenyl.

In yet another embodiment, the compound has the Formula (Vb) wherein $Z_4$ is selected from the group consisting of optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, $OR_c$, $SR_c$, and $NR_cR_c$.

Non-limiting examples of compounds of Formula (Vb) are:

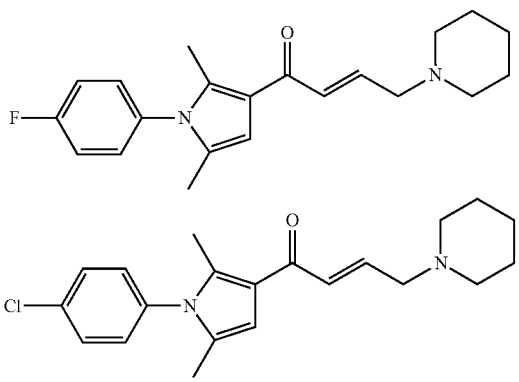

In one embodiment, compounds of the invention have the Formula (VIa). In some embodiments, the compound has the Formula (VIa), wherein Ring W is 5-membered nitrogen-containing heteroaryl or a 5-membered nitrogen-containing heterocyclic. In yet another embodiment, the compound has the Formula (VIa), wherein Ring W is a thienyl or a furanyl. In yet an additional embodiment, the compound has the Formula (VIa), wherein Ring W is a pyrrolyl. In additional aspects, the compound has the Formula (VIa), wherein $V_1$ is CN, C(O)$R_c$ or C(O)O$R_c$.

In an additional embodiment, the compound has the Formula (VIb):

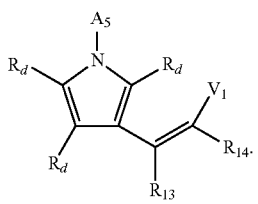

(VIb)

In some aspects, the compound has the Formula (VIb), wherein $V_1$ is C(O)$R_c$. In an additional embodiment, the compound has the Formula (VIb), wherein $A_5$ is optionally substituted phenyl. In certain additional aspects the compound has the Formula (VIc):

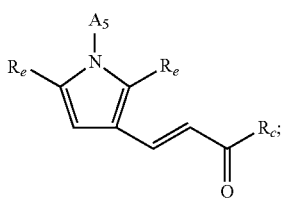

(VIc)

wherein each $R_e$ is independently an optionally substituted $C_1$-$C_4$ alkyl or an optionally substituted $C_3$-$C_{12}$ cycloalkyl.

As described above, in certain additional embodiments, the compound has the Formula (VId). In some embodiments, the compound has the Formula (VId), wherein Ring W is 5-membered nitrogen-containing heteroaryl or a 5-membered nitrogen-containing heterocyclic. In yet another embodiment, the compound has the Formula (VId), wherein Ring W is a thienyl or a furanyl. In yet an additional embodiment, the compound has the Formula (VId), wherein Ring W is a pyrrolyl.

In an additional embodiment, the compound has the Formula (VIe):

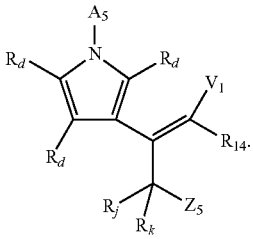

In some aspects, the compound has the Formula (VIe), wherein $A_5$ is optionally substituted aryl, such as optionally substituted phenyl. In yet additional aspects, the compound has the Formula (Ie), wherein $Z_5$ is selected from the group consisting of optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, O$R_c$, S$R_c$, and N$R_cR_c$. In additional aspects, the compound has the Formula (VIe), wherein $V_1$ is CN, C(O)$R_c$ or C(O)O$R_c$.

Non-limiting examples of compounds Formula (VIe) and/or Formula (VId) are shown in Table 3 below.

TABLE 3

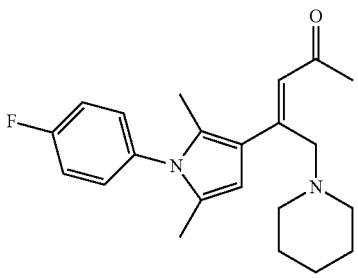 [SMILES: CC(=O)/C=C(\CN1CCCCC1)c1cc(C)n(-c2ccc(F)cc2)c1C]

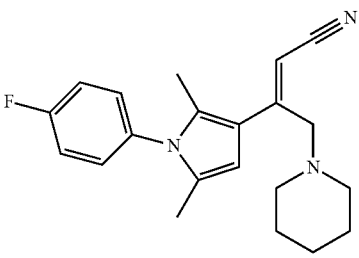 [SMILES: Cc1cc(/C(=C/C#N)CN2CCCCC2)c(C)n1-c1ccc(F)cc1]

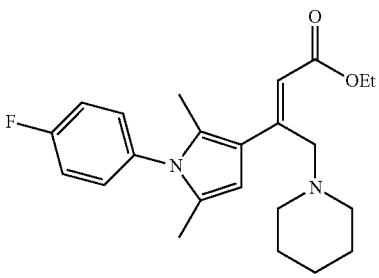 [SMILES: CCOC(=O)/C=C(\CN1CCCCC1)c1cc(C)n(-c2ccc(F)cc2)c1C]

TABLE 3-continued

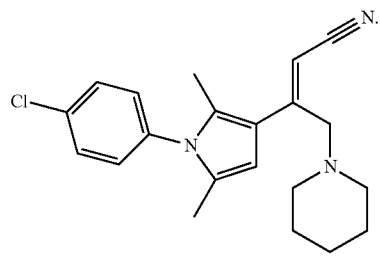 [SMILES: Cc1cc(/C(=C/C#N)CN2CCCCC2)c(C)n1-c1ccc(Cl)cc1]

In some embodiments, the compound has the Formula (VII). In one embodiment, the compound has the Formula (VII), wherein Ring T is a 5-membered nitrogen-containing heteroaryl or a 5-membered nitrogen-containing heterocyclic selected from the group consisting of:

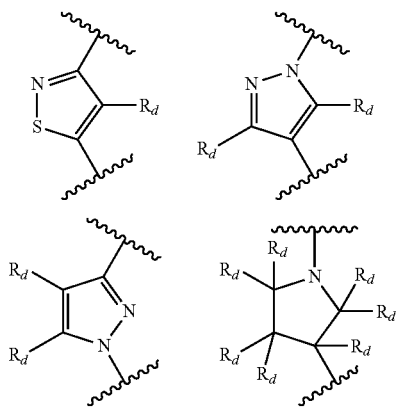

In yet additional embodiments, the compound has the Formula (VII), wherein Ring T is:

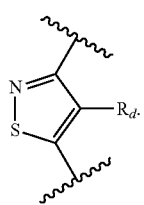

In some embodiments, the compound has the Formula (VII), wherein Ring T is:

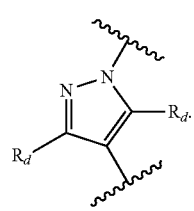

In another aspect, the compound has the Formula (VII), wherein Ring T is:

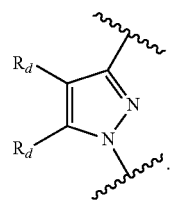

In yet another embodiment, the compound has the Formula (VII), wherein Ring T is:

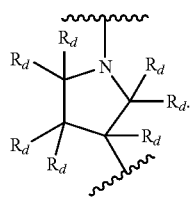

In a further embodiment, the compound has the Formula (VII), wherein Ring T is:

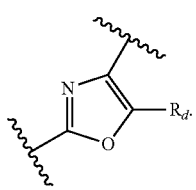

In yet another embodiment, the compound has the Formula (VII), wherein Ring T is:

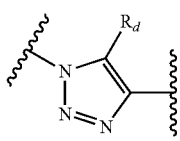

In a further embodiment, the compound has the Formula (VII), wherein Ring T is:

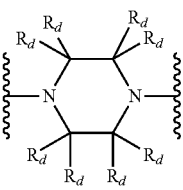

In yet another aspect, the compound has the Formula (VII), wherein Ring T is selected from the group consisting of:

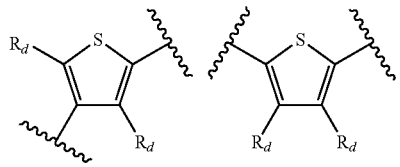

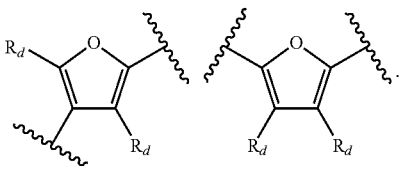

In a further aspect, the compound has the Formula (VII), wherein Ring T is selected from the group consisting of:

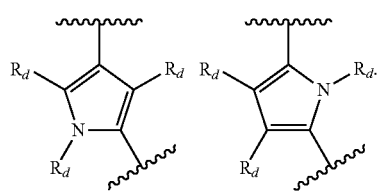

In some embodiments, the compound has the Formula (VII), wherein $A_6$ is optionally substituted aryl, for example, optionally substituted phenyl.

In certain aspects, the compound has the Formula (VII), wherein $Z_6$ is selected from the group consisting of optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, $OR_c$, $SR_c$, and $NR_cR_c$.

Non-limiting examples of compounds of Formula (VII) are shown in Table 4 below:

TABLE 4

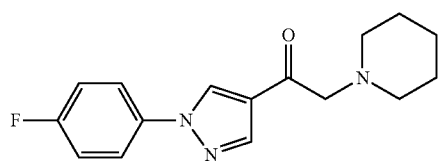 [SMILES: O=C(CN1CCCCC1)c1cnn(-c2ccc(F)cc2)c1]

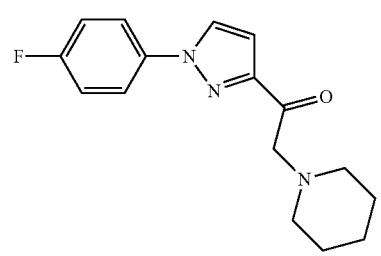 [SMILES: O=C(CN1CCCCC1)c1ccn(-c2ccc(F)cc2)n1]

TABLE 4-continued

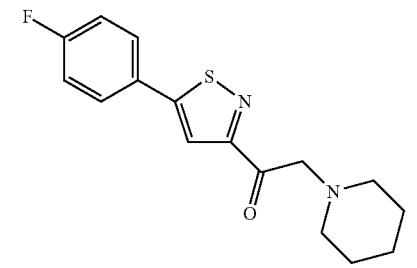 [SMILES: O=C(CN1CCCCC1)c1cc(-c2ccc(F)cc2)sn1]

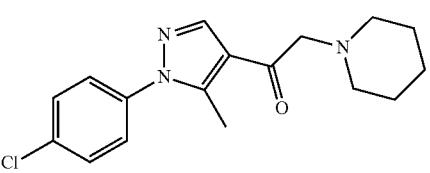 [SMILES: Cc1c(C(=O)CN2CCCCC2)cnn1-c1ccc(Cl)cc1]

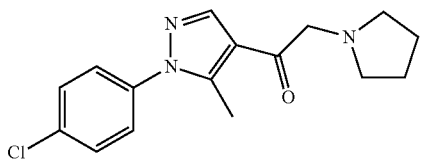 [SMILES: Cc1c(C(=O)CN2CCCC2)cnn1-c1ccc(Cl)cc1]

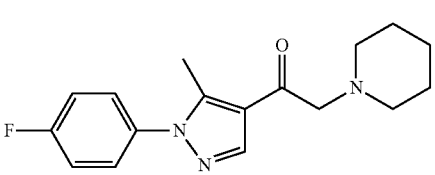 [SMILES: Cc1c(C(=O)CN2CCCCC2)cnn1-c1ccc(F)cc1]

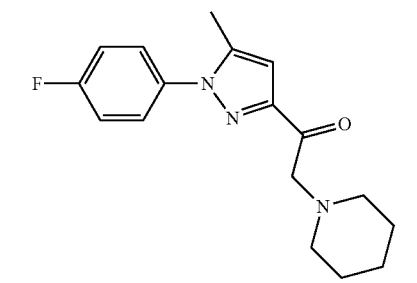 [SMILES: Cc1cc(C(=O)CN2CCCCC2)nn1-c1ccc(F)cc1]

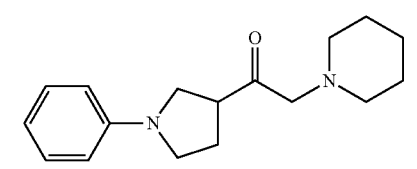 [SMILES: O=C(CN1CCCCC1)C1CCN(c2ccccc2)C1]

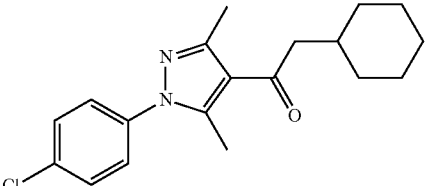

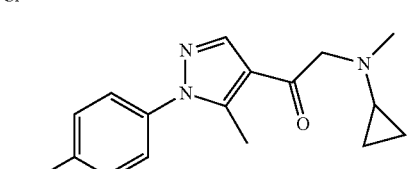

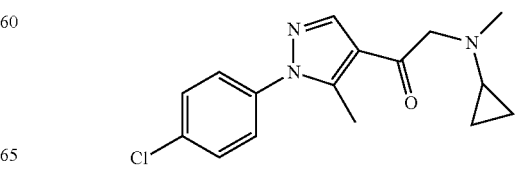

TABLE 4-continued
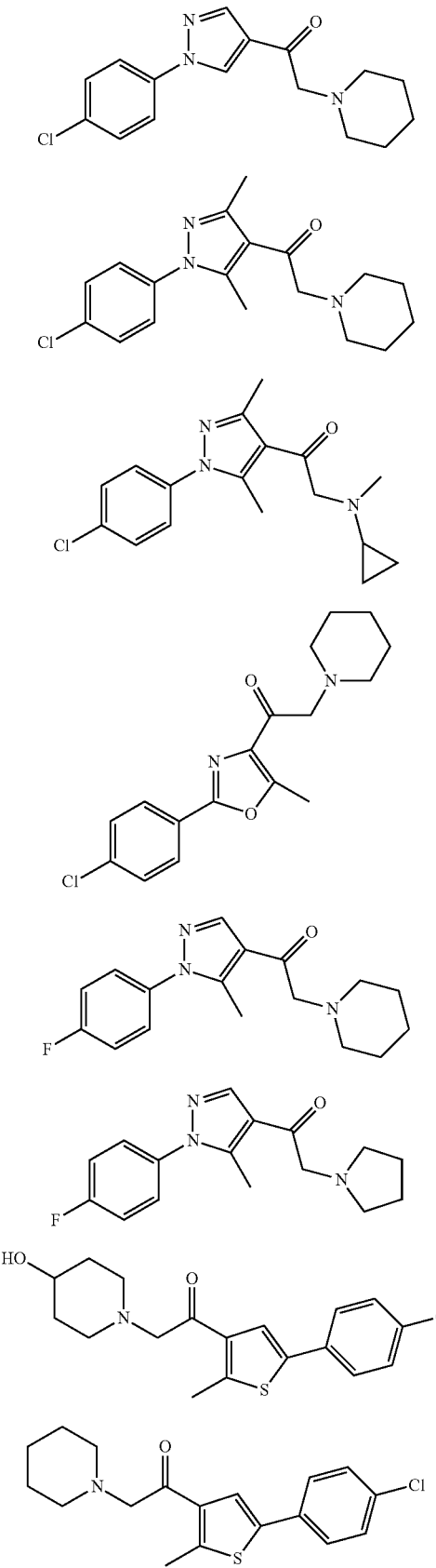
TABLE 4-continued
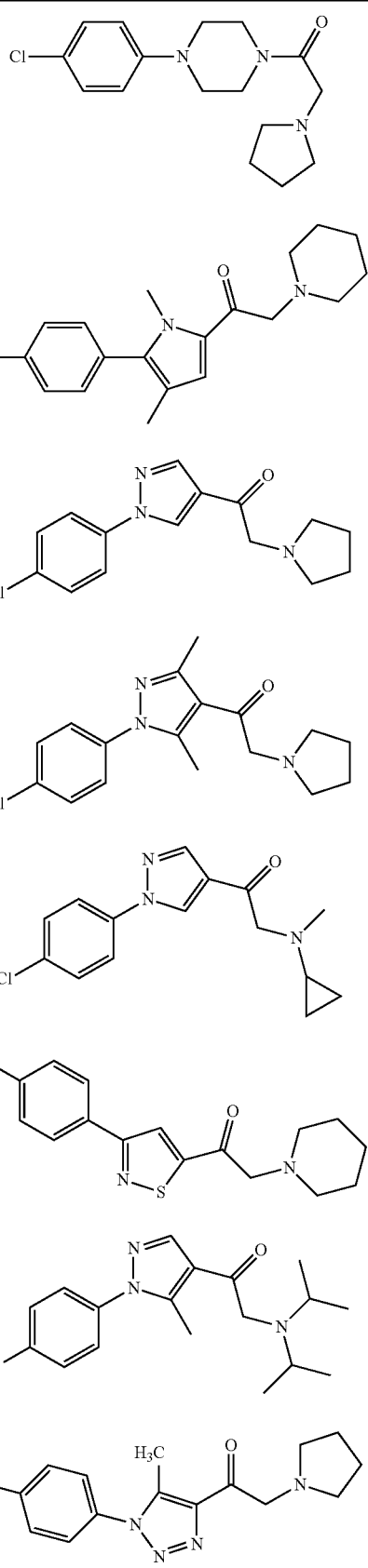

TABLE 4-continued

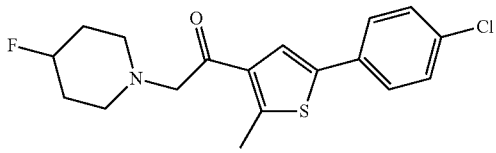 [SMILES: Cc1sc(-c2ccc(Cl)cc2)cc1C(=O)CN1CCC(F)CC1]

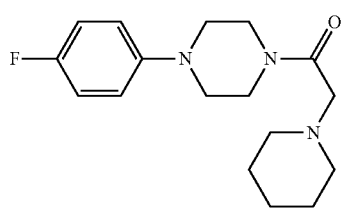

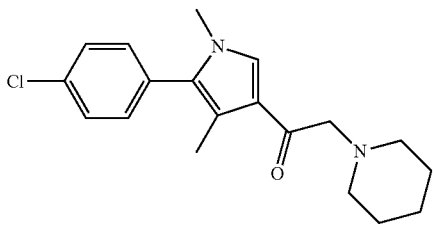 [SMILES: Cc1c(C(=O)CN2CCCCC2)cn(C)c1-c1ccc(Cl)cc1]

In an additional embodiment, the compound has the Formula (VIIIa). In one embodiment, the compound has the Formula (VIIIa), wherein Ring W is 5-membered nitrogen-containing heteroaryl or a 5-membered nitrogen-containing heterocyclic. In yet an additional embodiment, the compound has the Formula (VIIIa), wherein Ring W is a thienyl or a furanyl.

In an additional aspect, the compound of the invention has the Formula (VIIIb):

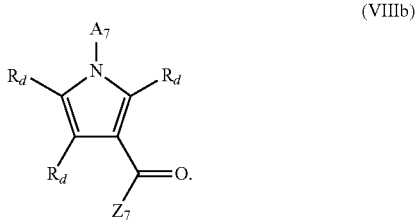

(VIIIb)

In yet an additional aspect, the compound has the Formula (VIIIe):

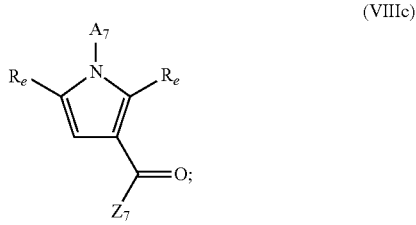

(VIIIc)

wherein each $R_e$ is independently an optionally substituted $C_1$-$C_4$ alkyl or an optionally substituted $C_3$-$C_{12}$ cycloalkyl.

In some embodiments, the compound has the Formula (VIIIa-VIIIc), wherein $Z_7$ is optionally substituted aryl or optionally substituted heteroaryl. In some embodiments, $Z_7$ is optionally substituted heteroaryl.

In additional aspects, the compound has the Formula (VIIIa-VIIIc), wherein $A_7$ is optionally substituted phenyl.

A non-limiting example of a compound having the Formula (VIIIe) is:

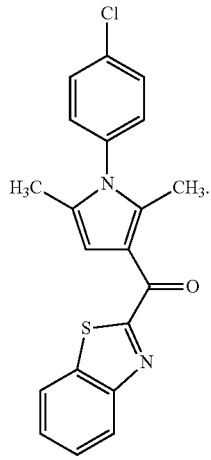 [SMILES: Cc1cc(C(=O)c2nc3ccccc3s2)c(C)n1-c1ccc(Cl)cc1]

In some embodiments, the compound has the Formula (IX), wherein $A_8$ is selected from the group consisting of optionally substituted $C_1$-$C_{10}$ alkyl and optionally substituted $C_2$-$C_{10}$ alkenyl.

Non-limiting examples of a compound having the Formula (IX) are shown below in Table 5.

TABLE 5

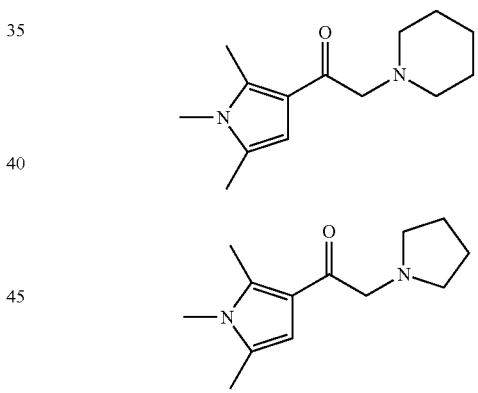

In certain embodiments, the compound has the Formula (Ia), (Ib), (Ic), (Id), (Ie) (II), (IIIa), (IIIb), (IIIc), (IIId), (IVa), (IVb), (IVc), (Va), (Vb), (VIa), (VIb), (VIc), (VId), (VIe), (VII), (VIIIa), (VIIIb), or (VIIIe), wherein $A_1$, $A_2$, $A_3$, $A_4$, $A_5$, $A_6$, or $A_7$ is a monocyclic or polycyclic group selected from the group consisting of optionally substituted $C_3$-$C_{12}$ cycloalkyl, optionally substituted $C_4$-$C_{12}$ cycloalkenyl, optionally substituted 3- to 12-membered heterocyclic, optionally substituted aryl, or optionally substituted heteroaryl.

In Formulae (Ia), (Ib), (Ic), (IIIa), (IIId), (IVa), (Va), (VIa), (VId) (VIIIa), and (IX), Ring W is defined as a 5-membered heteroaryl or a 5-membered heterocyclic, wherein each ring carbon atom of said 5-membered heteroaryl is substituted with one $R_d$ and wherein each ring nitrogen atom of said 5-membered heteroaryl is substituted with zero or one $R_d$ when said nitrogen atom or atoms are present, and wherein each ring carbon atom of said 5-membered heterocyclic is substituted with one or two $R_d$ and each ring nitrogen atom of said 5-membered heterocyclic is substituted with zero or one $R_d$, when said nitrogen atom or atoms are present. As will be understood by the person of skill in the art, $A_1$ to $A_5$ and $A_7$ to $A_8$ (referred to collectively in certain instances herein, as "A") and the Ring W substituent containing Y or $Z_2$-$Z_5$ and $Z_7$-$Z_8$ (referred to collectively in certain instances herein as the substituent containing Y or Z) can be bonded to a ring carbon atom or a ring nitrogen atom of Ring W. The remaining ring atoms of Ring W can be carbon, nitrogen, oxygen or sulfur. When one or more of the remaining ring atoms are carbon or nitrogen, these ring atoms can be bonded to zero to two $R_d$ depending on their valency. As explained above, when Ring W is a 5-membered heteroaryl, each ring carbon atom of Ring W (said atom not being attached to A or the substituent containing Y or Z) is substituted with one $R_d$. When Ring W is a 5-membered heteroaryl containing a ring nitrogen atom and the nitrogen atom is not attached to A or the Ring W substituent containing Y or Z, the nitrogen atom can be substituted with zero or one $R_d$ depending on its valence. For example, the ring nitrogen atom is not substituted with $R_d$ (in other words, is substituted with zero $R_d$) when said nitrogen there is a double bond between the nitrogen and an adjacent ring atom. In another example, the 5-membered heterocyclic, each ring carbon atom (said atom not being attached to A or the substituent containing Y or Z) is attached to one $R_d$ when said carbon atom is double-bonded to an adjacent ring atom and is attached to two $R_d$ when there is a single bond between carbon and its adjacent atoms.

The number of $R_d$ groups as well as their positions on Ring W will depend on the specific heteroaryl or heterocyclic ring. For example, if in Formula (Ia), Ring W is a thienyl, the ring has two $R_d$ groups, but their positions can vary depending on the positions of $A_1$ and the Ring W substituent containing Y (the —C(O)—C($R_3$)($R_4$)—Y group) as is shown by way of example below:

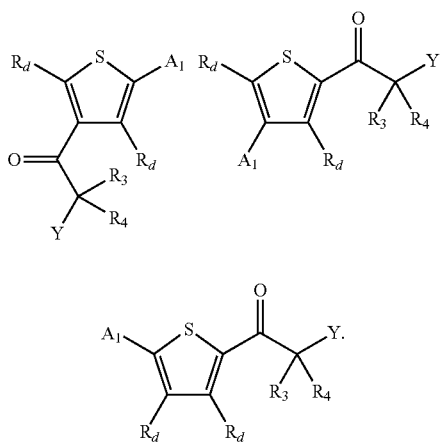

In another example, if in Formula (Ia), Ring W is a pyrrolyl, the ring has three $R_d$ groups and their positions vary depending on the positions of $A_1$ and the Ring W substituent containing Y as shown by way of example below:

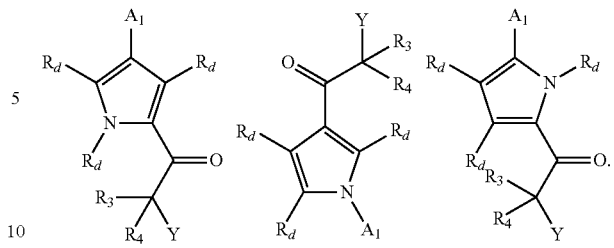

In certain embodiments, in Formulae (Ia), (Ib), (Ic), (IIIa), (IIId), (IVa), (Va), (VIa), (VId), (VIIIa), and (IX), Ring W is selected from the group consisting of:

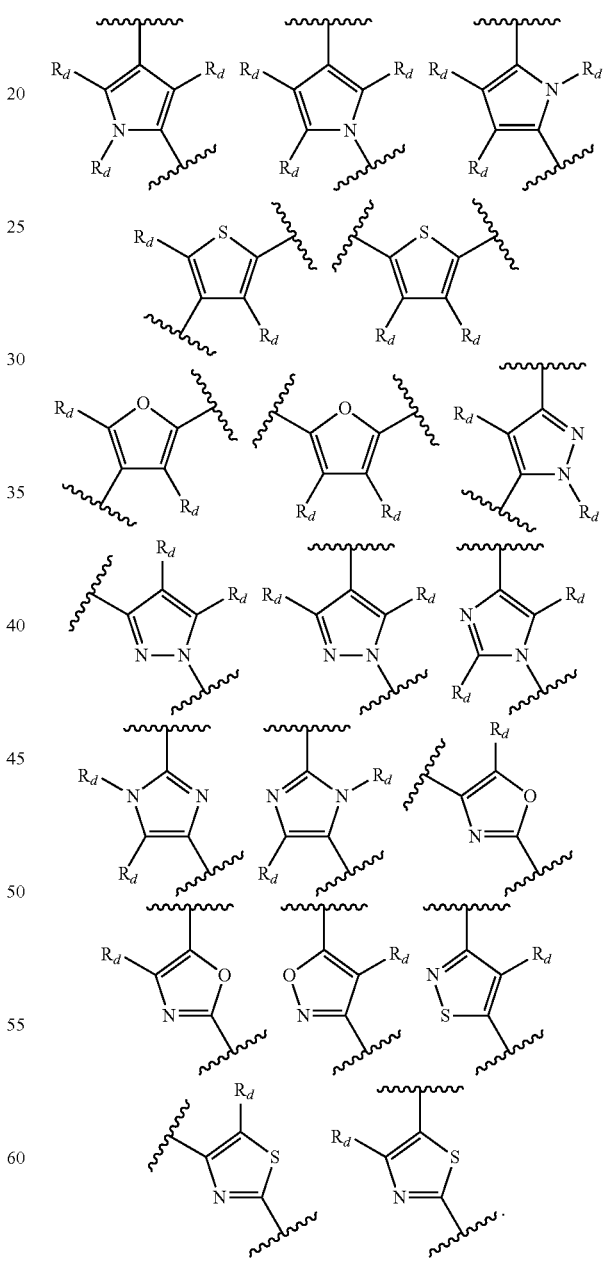

In the specific examples of Ring W depicted above, the positions of the $R_d$ groups are as shown. The groups at the positions designated by ⁓ can be $A_1$-$A_5$ and $A_7$ (collectively shown as "A") or the Ring W substituent containing Y (for Formula (Ia-Ic)) or the Ring W substituent containing $Z_2$-$Z_5$ and $Z_7$ (for Formula (IIIa), (IIId), (IVa), (Va), (VIa), (VId) and (VIIIa)).

For some of the some of the specific examples of Ring W depicted above, there are two possible positions of group A and the Ring W substituent containing Y or Z. The depiction above is intended to encompass all such compounds. For example, in certain embodiments, Ring W in Formulae (Ia), (Ib), (Ic), (IIIa), (IIId), (IVa), (Va), (VIa), (VId), (VIIIa) or (IX) is as shown below (wherein $A_1$-$A_5$ and $A_7$-$A_8$ and $R_d$ are as shown), and positions designated by ⁓ is the Ring W substituent containing Y or $Z_2$-$Z_5$ and $Z_7$-$Z_8$):

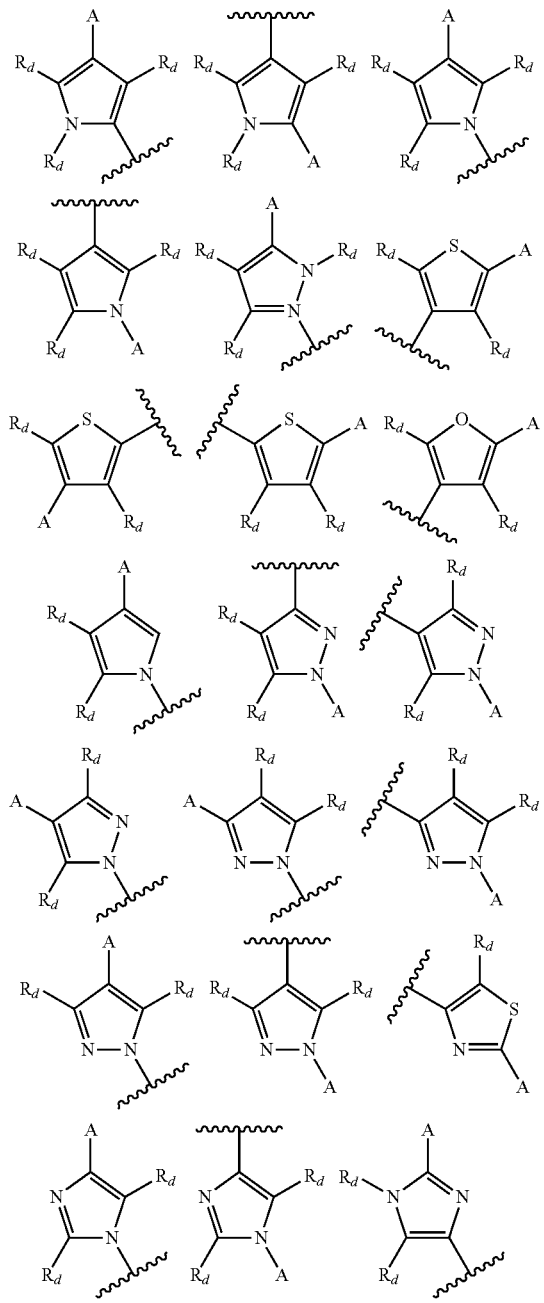
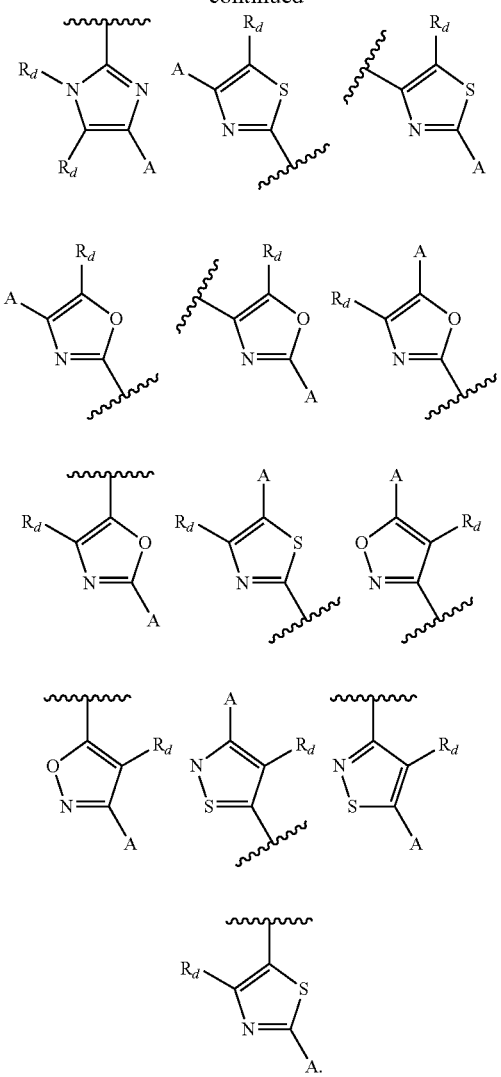

Similarly, in Formula (VII), there are two possible positions of group $A_6$ and the Ring W substituent containing $Z_6$. For example, the invention encompasses Ring T as shown below (wherein $A_6$ and $R_d$ are as shown), and positions designated by ⁓ is the Ring W substituent containing $Z_6$):

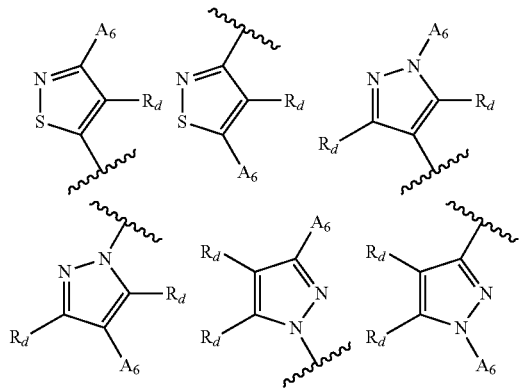

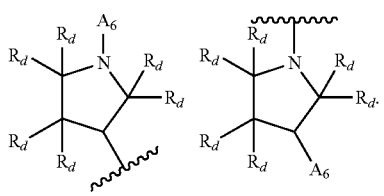

As described above, in some embodiments two vicinal $R_d$ groups, when present, are taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl. For example, two vicinal $R_d$ group can be taken together to form said cyclic group when Ring W is one of the following:

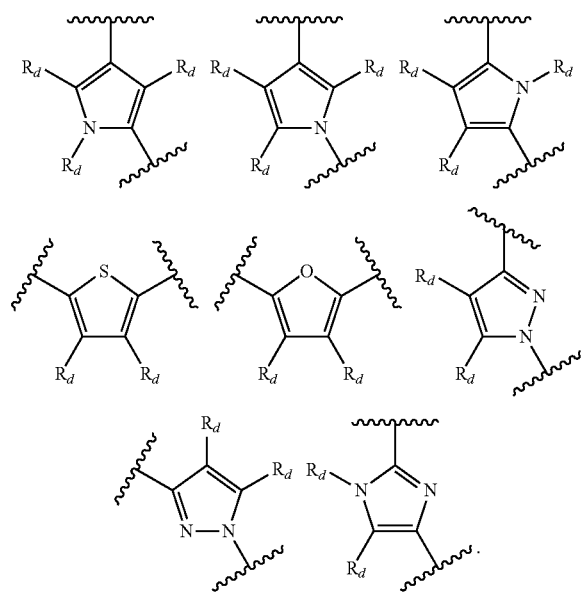

Also as described above, $R_d$ and an A group, when attached to adjacent atoms, can be taken together to form a fused monocyclic or polycyclic group selected from the group consisting of optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl. For example, $R_d$ and A can be taken to form a fused cyclic group as previously described when Ring W is one of the following:

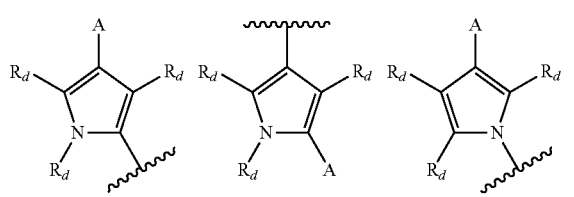

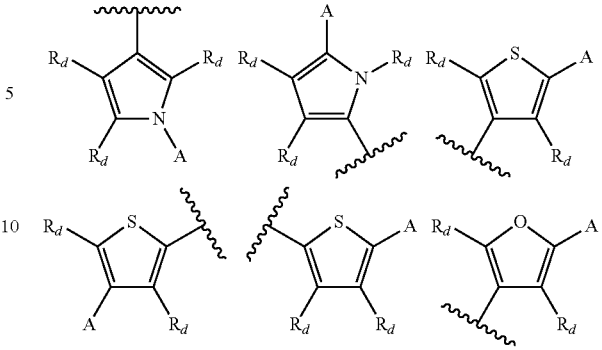

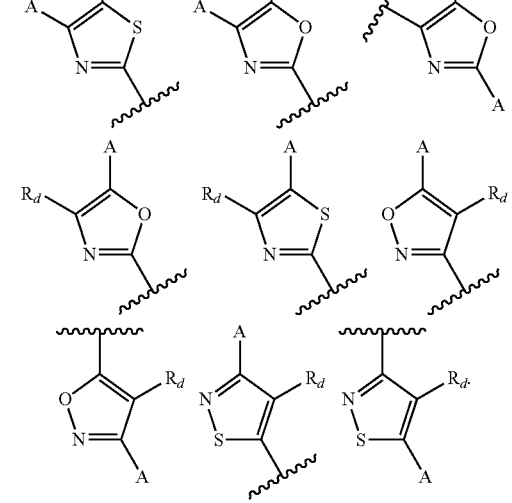

In addition, as described above for Formula (Ia), $R_3$ and an $R_d$ group (when $R_d$ and the $C(O)C(R_3)(R_4)Y$ substituent are attached to adjacent atoms) can be taken together to form a fused monocyclic group selected from the group consisting of $C_5$-$C_{12}$ cycloalkyl, $C_5$-$C_{12}$ cycloalkenyl, 5- to 12-membered heterocyclic, $C_6$-$C_{12}$ aryl and 5- to 12-membered heteroaryl, each optionally substituted with $R_4$ and Y, and wherein the fused ring can optionally be further substituted. Similarly, in Formula (IIIa), $R_7$ and $R_d$ can be taken together to form a fused monocyclic group selected from the group consisting of $C_5$-$C_{12}$ cycloalkyl, $C_5$-$C_{12}$ cycloalkenyl, 5- to 12-membered heterocyclic, $C_5$-$C_{12}$ aryl, and 5- to 12-membered heteroaryl, each substituted with $R_8$ and $Z_2$, (and optionally further substituted) when the $R_d$ and the Ring W substituent containing $Z_2$ are attached to adjacent carbon atoms.

As discussed above, the invention additionally encompasses pharmaceutical compositions. For example, pharmaceutical compositions comprising a pharmaceutically acceptable carrier and a compound of Formula (Ia-Ie), (II), (IIIa-IIId), (IVa-IVc), (Va-Vb), (VIa-VIe), (VII), (VIIIa-VIIIc), and (IX) and pharmaceutically acceptable salts, prodrugs or solvates thereof, are encompassed by the invention.

It is to be understood that the specific embodiments described herein can be taken in combination with other specific embodiments delineated herein. For example, for compounds of Formula (Ia), Ring W is described a heteroaryl in one embodiment described above and Y was described as selected from the group consisting of optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, $OR_c$, $SR_c$ and $C(O)NR_cR_c$ in an additional embodiment above. It is to be understood that the invention thus encompasses compounds of Formula (Ia), wherein Ring W is a heteroaryl and Y is selected from the group consisting of optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, $OR_c$, $SR_c$ and $C(O)NR_cR_c$.

The term "alkyl", as used herein, unless otherwise indicated, refers to both branched and straight-chain saturated aliphatic hydrocarbon groups having the specified number of carbon atoms; for example, "$C_1$-$C_{10}$ alkyl" denotes alkyl having 1 to 10 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

The term, "alkenyl", as used herein, refers to both straight and branched-chain moieties having the specified number of carbon atoms and having at least one carbon-carbon double bond.

The term, "alkynyl", as used herein, refers to both straight and branched-chain moieties having the specified number or carbon atoms and having at least one carbon-carbon triple bond.

The term "cycloalkyl," as used herein, refers to cyclic alkyl moieties having 3 or more carbon atoms. Examples of cycloalkyl include, but are not limited to, cyclopropyl, cyclobutyl, cyclopentyl, cyclohexyl, cycloheptyl and adamantyl.

The term "cycloalkenyl," as used herein, refers to cyclic alkenyl moieties having 3 or more carbon atoms.

The term "cycloalkynyl," as used herein, refers to cyclic alkynyl moieties having 5 or more carbon atoms.

The term "heterocyclic" encompasses heterocycloalkyl, heterocycloalkenyl, heterobicycloalkyl, heterobicycloalkenyl, heteropolycycloalkyl, heteropolycycloalkenyl and the like. Heterocycloalkyl refers to cycloalkyl groups containing one or more heteroatoms (O, S, or N) within the ring. Heterocycloalkenyl as used herein refers to cycloalkenyl groups containing one or more heteroatoms (O, S or N) within the ring. Heterobicycloalkyl refers to bicycloalkyl groups containing one or more heteroatoms (O, S or N) within a ring. Heterobicycloalkenyl as used herein refers to bicycloalkenyl groups containing one or more heteroatoms (O, S or N) within a ring.

Cycloalkyl, cycloalkenyl, heterocyclic, groups also include groups similar to those described above for each of these respective categories, but which are substituted with one or more oxo moieties.

The term "aryl", as used herein, refers to mono- or polycyclic aromatic carbocyclic ring systems. A polycyclic aryl is a polycyclic ring system that comprises at least one aromatic ring. Polycyclic aryls can comprise fused rings, covalently attached rings or a combination thereof. The term "aryl" embraces aromatic radicals, such as, phenyl, naphthyl, indenyl, tetrahydronaphthyl, and indanyl. An aryl group may be substituted or unsubstituted.

The term "heteroaryl", as used herein, refers to aromatic carbocyclic groups containing one or more heteroatoms (O, S, or N) within a ring. A heteroaryl group can be monocyclic or polycyclic. A heteroaryl group may additionally be substituted or unsubstituted. The heteroaryl groups of this invention can also include ring systems substituted with one or more oxo moieties. A polycyclic heteroaryl can comprise fused rings, covalently attached rings or a combination thereof. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, thiazolopyridinyl, oxazolopyridinyl and azaindolyl. The foregoing heteroaryl groups may be C-attached or heteroatom-attached (where such is possible). For instance, a group derived from pyrrole may be pyrrol-1-yl (N-attached) or pyrrol-3-yl (C-attached).

The term "substituted" refers to substitution by independent replacement of one, two, or three or more of the hydrogen atoms with substituents including, but not limited to, —$C_1$-$C_{12}$ alkyl, —$C_2$-$C_{12}$ alkenyl, —$C_2$-$C_{12}$ alkynyl, —$C_3$-$C_{12}$ cycloalkyl, —$C_3$-$C_{12}$ cycloalkenyl, $C_3$-$C_{12}$ cycloalkynyl, -heterocyclic, —F, —Cl, —Br, —I, —OH, —$NO_2$, —$N_3$, —CN, —$NH_2$, oxo, thioxo, —$NHR_x$, —$NR_xR_x$, dialkylamino, -diarylamino, -diheteroarylamino, —$OR_x$, —$C(O)R_y$, —$C(O)C(O)R_y$, —$OCO_2R_y$, —$OC(O)R_y$, $OC(O)C(O)R_y$, —$NHC(O)R_y$, —$NHCO_2R_y$, —$NHC(O)C(O)R_y$, $NHC(S)NH_2$, —$NHC(S)NHR_x$, —$NHC(NH)NH_2$, —$NHC(NH)NHR_x$, —$NHC(NH)R_x$, —$C(NH)NHR_x$, (C=$NR_x$)$R_x$; —$NR_xC(O)R_x$, —$NR_xCO_2R_y$, —$NR_xC(O)C(O)R_y$, —$NR_xC(S)NH_2$, —$NR_xC(O)NR_xR_x$, $NR_xS(O)_2NR_xR_x$, $NR_xC(S)NHR_x$, —$NR_xC(NH)NH_2$, —$NR_xC(NH)NHR_x$, —$NR_xC(NH)R_x$, —$C(NR_x)NHR_x$—S(O)$_b R_x$, —$NHSO_2R_x$, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, -polyalkoxyalkyl, -polyalkoxy, -methoxymethoxy, -methoxyethoxy, —SH, —S—$R_x$, or -methylthiomethyl, wherein $R_x$ is selected from the group consisting of —$C_1$-$C_{12}$ alkyl, —$C_2$-$C_{12}$ alkenyl, —$C_2$-$C_{12}$ alkynyl, —$C_3$-$C_{12}$ cycloalkyl, -aryl, -heteroaryl and -heterocyclic, each optionally substituted, —$R_y$ is selected from the group consisting of —$C_1$-$C_{12}$ alkyl, —$C_2$-$C_{12}$ alkenyl, —$C_2$-$C_{12}$ alkynyl, —$C_3$-$C_{12}$ cycloalkyl, -aryl, -heteroaryl, -heterocyclic, —$NH_2$, —NH—$C_1$-$C_{12}$ alkyl, —NH—$C_2$-$C_{12}$ alkenyl, —NH—$C_2$-$C_{12}$-alkynyl, —NH—$C_3$-$C_{12}$ cycloalkyl, —NH-aryl, —NH-heteroaryl and —NH-heterocyclic, each optionally substituted, and b is 0, 1 or 2. It is understood that the aryls, heteroaryls, alkyls, and the like can be further substituted.

The term "haloalkyl" as used herein refers to an alkyl group having 1 to (2 d+1) substituent(s) independently selected from F, Cl, Br or I, where n is the maximum number of carbon atoms in the alkyl group.

"H" is an abbreviation for hydrogen.

"Me" is an abbreviation for methyl.

Non-limiting examples of optionally substituted aryl are phenyl, substituted phenyl, naphthyl and substituted naphthyl.

Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. "Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. When the compounds described herein contain olefinic double bonds or other centers of geometric asymmetry, and unless specified otherwise, it is intended that the compounds include both E and Z geometric isomers. Likewise, all tautomeric forms are also intended to be included.

Where a particular stereochemistry is described or depicted it is intended to mean that a particular enantiomer is present in excess relative to the other enantiomer. A compound has an R-configuration at a specific position when it is present in excess compared to the compound having an S-configuration at that position. A compound has an S-configuration at a specific position when it is present in excess compared to the compound having an R-configuration at that position.

It is to be understood that atoms making up the compounds of the present invention are intended to include isotopic forms of such atoms. Isotopes, as used herein, include those atoms having the same atomic number but different mass numbers. Isotopes of hydrogen include, for example, tritium and deuterium, and isotopes of carbon include, for example, $^{13}C$ and $^{14}C$. The invention therefore encompasses embodiments in which one or more of the hydrogen atoms in Formulae (Ia-Ie), (II), (IIIa-IIId), (IVa-IVc), (Va-Vb), (VIa-VIe), (VII), (VIIIa-VIIIc), and (IX) are replaced with deuterium. The invention also encompasses embodiments wherein one or more of the carbon atoms in Formulae (Ia-Ie), (II), (IIIa-IIId), (IVa-IVc), (Va-Vb), (VIa-VIe), (VII), (VIIIa-VIIIc), and (IX) is replaced with silicon atoms.

The invention additionally encompasses embodiment wherein one or more of the nitrogen atoms in Formulae (Ia-Ie), (II), (IIIa-IIId), (IVa-IVc), (Va-Vb), (VIa-VIe), (VII), (VIIIa-VIIIc), and (IX) are oxidized to N-oxide.

Methods for the synthesis of the compounds described herein have been described in the literature, for example in: 1) Banik, B. et al. "Simple Synthesis of Substituted Pyrroles" *J. Org. Chem*, 2004, 69, 213; 2) Sawada, Y. et al. "Eight-Membered Oxygen Heterocycles by Brook Rearrangement-mediated [3+4] Annulation" *Org. Lett.* 2004, 6, 2277; 3) Aubé, J. et al. "Synthetic Aspects of an Asymmetric Nitrogen-Insertion Process: Preparation of Chiral, Non-Racemic Caprolactams and Valerolactams. Total Synthesis of (−)-Alloyohimbane" *J. Am. Chem. Soc.* 1990, 112, 4879; 4) Ookawa, A. et al. "Asymmetric Synthesis of Optically Active threo- and erythro-Pyrrolidinylbenzyl Alcohol by the Highly Stereospecific Arylation of (S)-Proline and the Subsequent Highly Diastereoselective Reduction of the α-Amineo Ketone" *J. Chem. Soc. Perkin Trans. I,* 1987, 7, 1465; 5) Baasov, T. et al. "Model Compounds for the Study of Spectroscopic Properties of the Visial Pigments of Bacteriorhodopsin" *J. Am. Chem. Soc.* 1985, 107, 7524; 6) Finar, I. et al. "Preparation and properties of some pyrazolyl ketones" *J. Chem. Soc. C: Organic,* 1967, 16, 1494; 7a) Schenon, P. et al. "Reaction of 2-Dimethylaminomethylene-1,3-diones with Dinucleopholes. I. Synthesis of 1,5-Disubstituted 4-Acylpyrazoles" *J. Heterocyclic Chem.* 1982, November-December, 1355; b) Menishi, G. et al. "Ring Contraction of a 5-Acetylpyrimidine into Pyrazoles but the Action of Substituted Hydrazines in Acidic Medium" *J. Heterocyclic Chem.* 1986, January-February, 275; c) Goddard C. J. "Anti-inflammatory 1-Phenylpyrazole-4-Heteroarylalkanoic Acids" *J. Heterocyclic Chem.* 1991, October 1607; 8) Moriyama, K. et al. "Effects of Introduction of Hydrophobic Group on Ribavirin Base on Mutation Induction and Anti-RNA Viral Activity" *J. Med. Chem.* 2008, 51, 159; 9) Poon, S. F. "Discovery and Optimization of Substituted 1-(1-Phenyl-1H-pyrazol-3-yl)methanamines as Potent and Efficacious Type II Calcimimetics, *J. Med. Chem.* 2009, 52, 6535; 10) Wynberg, H. et al. "A Convenient Route to Polythiophenes" *Syn. Comm.* 1984, 14, 1; and 11) Badland, M. "Thiophene and bioisostere derivatives as new MMP12 inhibitors" *Bioorganic Med. Chem Lett.* 2011, 21, 528, the contents of each of which are incorporated by reference herein.

Exemplary synthetic routes for the preparation of compounds of the invention are shown below as Schemes 1-8 below. As will be understood by the skilled artisan, diastereomers can be separated from the reaction mixture using column chromatography.

Scheme 1

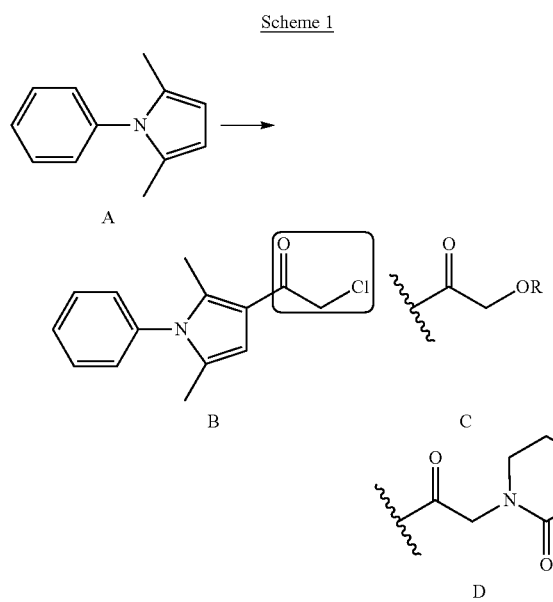

A Paal-Knorr pyrrole synthesis using aniline and an appropriate diketone affords pyrrole A[1]. A Friedel-Crafts acylation with chloroacetyl chloride and AlCl$_3$ provides intermediate B. The chloride can be easily displaced with a variety of O[2], N[3], S and C based nucleophiles to provide the desired compounds.

Scheme 2

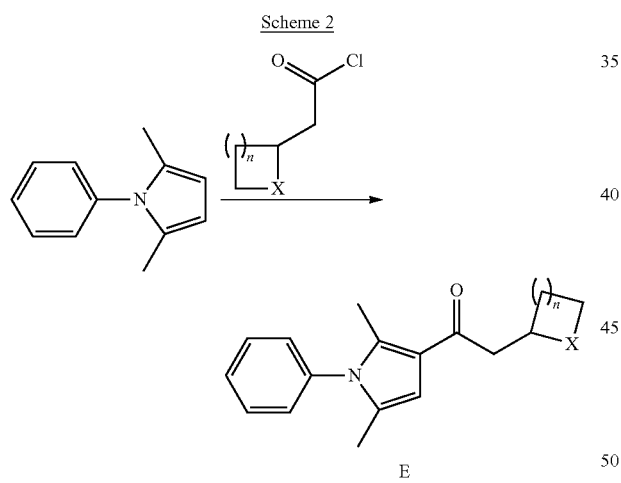

A Friedel-Crafts acylation using an appropriately substituted acetylchloride and pyrrole A will afford the desired acyl pyrroles E where X can be optionally substituted N, S, C, O.[4]

Scheme 3

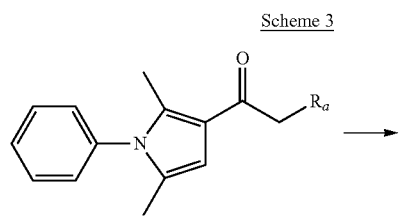

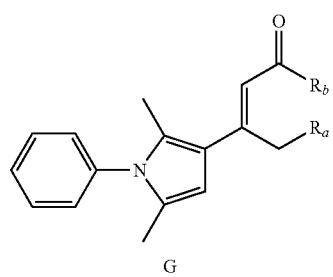

Beginning with compounds prepared in the previous schemes a Wittig or Horner-Wadsworth-Emmons reaction will afford α,β-unsaturated carbonyl compounds of type G.[5]

Scheme 4

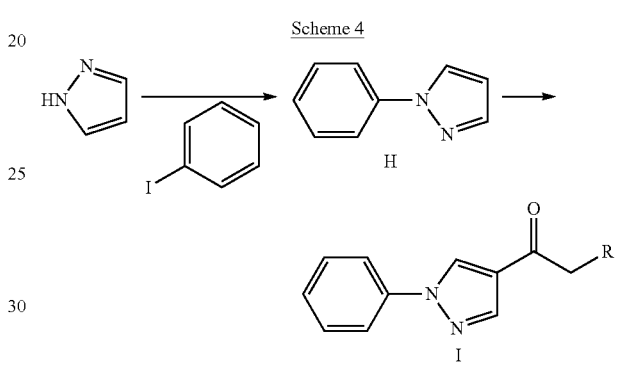

A cross-coupling reaction with a pyrazole and an appropriate iodide affords compound H.[9] Acylation[6] of H with an appropriate acid chloride followed in some instances by further modifications (see Scheme 1) provides compounds of type I.

Scheme 5

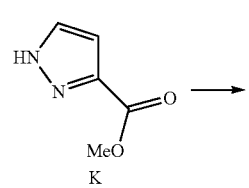

Compounds of this type where R is a halogen are known in the literature. Conversion of the known compounds to the desired compounds J is described in Scheme 1.

Scheme 6

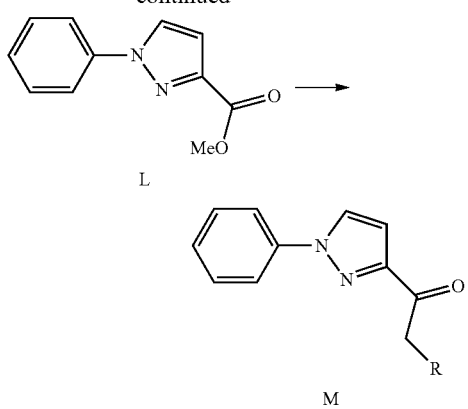

Compound K is known in the literature[8]. A cross coupling with an appropriate iodide would afford L[9]. The methyl ester can be elaborated further to give M where R is a halogen further elaboration is described in Scheme 1.

Known bromothiophene can undergo a palladium catalyzed cross-coupling reaction with an appropriate aryl-metal species to afford substituted thiophene N. The oxidation of methyl thiophenes is described in reference 10. A similar oxidation of pyrazoles is described in 7c. Conversion of the acid the α-halo ketone[7] followed by appropriate substituted affords desired compounds P.

Preparation of compounds such as compound S are described in the literature.[11] Conversion of a carboxylic acid to an -halo ketone[7] is also described. Conversion to the desired compounds T is described in Scheme 1.

The invention encompasses pharmaceutically acceptable salts of the compounds described herein. Thus, in certain aspects, the invention is directed to pharmaceutically acceptable salts of compounds of Formulae (Ia-Ie), (II), (IIIa-IIId), (IVa-IVc), (Va-Vb), (VIa-VIe), (VII), and (VIIIa-VIIIc). As used herein, a "pharmaceutically acceptable salt" includes an ionic bond-containing product of the reaction between the disclosed compound with either an acid or a base, suitable for administering to a subject. Pharmaceutically acceptable salts are well known in the art and are described, for example, in Berge et al. (1977), Pharmaceutical Salts, Journal of Pharmaceutical Sciences, 69(1): 1-19, the contents of which are herein incorporated by reference. A non-limiting example of a pharmaceutically acceptable salt is an acid salt of a compound containing an amine or other basic group which can be obtained by reacting the compound with a suitable organic or inorganic acid. Examples of pharmaceutically acceptable salts also can be metallic salts including, but not limited to, sodium, magnesium, calcium, lithium and aluminum salts. Further examples of pharmaceutically acceptable salts include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, benzoates and salts with amino acids such as glutamic acid. Salts can also be formed with suitable organic bases when the compound comprises an acid functional group such as —COOH or —SO$_3$H. Such bases suitable for the formation of a pharmaceutically acceptable base addition salts with compounds of the present invention include organic bases that are nontoxic and strong enough to react with the acid functional group. Such organic bases are well known in the art and include amino acids such as arginine and lysine, mono-, di-, and triethanolamine, choline, mono-, di-, and trialkylamine, such as methylamine, dimethylamine, and trimethylamine, guanidine, N-benzylphenethylamine, N-methylglucosamine, N-methylpiperazine, morpholine, ethylendiamine, tris(hydroxymethyl)aminomethane and the like.

The invention also includes hydrates of the compounds described herein, including, for example, solvates of the compounds described herein. In some embodiments, the invention is a solvate of a compound of Formula (Ia), (Ib), (Ic), (Id), (Ie), (II), (IIIa), (IIIb), (IIIc), (IIId), (IVa), (IVb), (IVc), (Va), (Vb), (VIa), (VIb), (VIc), (VId), (Vie), (VII), (VIIIa), (VIIIb) (VIIIe), or (IX).

Also included in the present invention are prodrugs of the compounds described herein, for example, prodrugs of a compound of Formula (Ia), (Ib), (Ic), (Id), (Ie), (II), (IIIa), (IIIb), (IIIc), (IIId), (IVa), (IVb), (IVc), (Va), (Vb), (VIa), (VIb), (VIc), (VId), (Vie), (VII), (VIIIa), (VIIIb), (VIIIe) or (IX).

The invention additionally includes clathrates of the compounds described herein. In some embodiments, the invention is directed to clathrates of a compound of Formula (Ia), (Ib), (Ic), (Id), (Ie), (II), (IIIa), (IIIb), (IIIc), (IIId), (IVa), (IVb) (IVc), (Va), (Vb), (VIa), (VIb), (VIc), (VId), (Vie), (VII), (VIIIa), (VIIIb), (VIIIe) or (IX).

As discussed above, the invention includes pharmaceutical compositions comprising a pharmaceutically acceptable carrier or excipient and a compound described herein. The compound Formula (Ia), (Ib), (Ic), (Id), (Ie), (II), (IIIa), (IIIb), (IIIc), (IIId), (IVa), (IVb) (IVc), (Va), (Vb), (VIa), (VIb), (VIc), (VId), (Vie), (VII), (VIIIa), (VIIIb), (VIIIe), or (IX), and a pharmaceutically acceptable salt, solvate, clathrate or prodrug of any of thereof, can be administered in pharmaceutical compositions comprising a pharmaceutically acceptable carrier or excipient. The excipient can be chosen based on the expected route of administration of the composition in therapeutic applications. The route of administration of the composition depends on the condition to be treated. For example, intravenous injection may be preferred for treatment of a systemic disorder and oral administration may be preferred to treat a gastrointestinal disorder. The route of administration and the dosage of the composition to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms.

Pharmaceutical compositions comprising compounds of Formulae (Ia), (Ib), (Ic), (Id), (Ie), (II), (IIIa), (IIIb), (IIIc), (IIId), (IVa), (IVb), (IVc), (Va), (Vb), (VIa), (VIb), (VIc), (VId), (Vie), (VII), (VIIIa), (VIIIb), (VIIIe), or (IX), and pharmaceutically acceptable salts, solvates, clathrates and prodrugs thereof, can be administered by a variety of routes including, but not limited to, parenteral, oral, pulmonary, ophthalmic, nasal, rectal, vaginal, aural, topical, buccal, transdermal, intravenous, intramuscular, subcutaneous, intradermal, intraocular, intracerebral, intralymphatic, intraarticular, intrathecal and intraperitoneal.

The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the pharmacologic agent or composition. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Pharmaceutical compositions can also include large, slowly metabolized macromolecules such as proteins, polysaccharides such as chitosan, polylactic acids, polyglycolic acids and copolymers (such as latex functionalized SEPHAROSE™, agarose, cellulose, and the like), polymeric amino acids, amino acid copolymers, and lipid aggregates (such as oil droplets or liposomes).

The compositions can be administered parenterally such as, for example, by intravenous, intramuscular, intrathecal or subcutaneous injection. Parenteral administration can be accomplished by incorporating a composition into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Injectable formulations can be prepared either as liquid solutions or suspensions; solid forms suitable for solution in, or suspension in, liquid vehicles prior to injection can also be prepared. The preparation also can also be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The compositions and pharmacologic agents described herein can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, transdermal applications and ocular delivery. For suppositories, binders and carriers include, for example, polyalkylene glycols or triglycerides; such suppositories can be formed from mixtures containing the active ingredient in the range of about 0.5% to about 10%, preferably about 1% to about 2%. Oral formulations include excipients, such as pharmaceutical grades of mannitol, lactose, starch, magnesium stearate, sodium saccharine, cellulose, and magnesium carbonate. Topical application can result in transdermal or intradermal delivery. Transdermal delivery can be achieved using a skin patch or using transferosomes. [Paul et al., Eur. J. Immunol. 25: 3521-24, 1995; Cevc et al., Biochem. Biophys. Acta 1368: 201-15, 1998].

For the purpose of oral therapeutic administration, the pharmaceutical compositions can be incorporated with excipients and used in the form of tablets, troches, capsules, elixirs, suspensions, syrups, wafers, chewing gums and the like. Tablets, pills, capsules, troches and the like may also contain binders, excipients, disintegrating agent, lubricants, glidants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and non-toxic in the amounts used. In another embodiment, the composition is administered as a tablet or a capsule.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor, and the like. For vaginal administration, a pharmaceutical composition may be presented as pessaries, tampons, creams, gels, pastes, foams or spray.

The pharmaceutical composition can also be administered by nasal administration. As used herein, nasally administering or nasal administration includes administering the composition to the mucus membranes of the nasal passage or nasal cavity of the patient. As used herein, pharmaceutical compositions for nasal administration of a composition include therapeutically effective amounts of the compounds prepared by well-known methods to be administered, for example, as a nasal spray, nasal drop, suspension, gel, ointment, cream or powder. Administration of the composition may also take place using a nasal tampon or nasal sponge.

For topical administration, suitable formulations may include biocompatible oil, wax, gel, powder, polymer, or other liquid or solid carriers. Such formulations may be administered by applying directly to affected tissues, for example, a liquid formulation to treat infection of conjunctival tissue can be administered dropwise to the subject's eye, or a cream formulation can be administered to the skin.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the pharmaceutical composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

In addition to the usual meaning of administering the formulations described herein to any part, tissue or organ whose primary function is gas exchange with the external environment, for purposes of the present invention, "pulmonary" will also mean to include a tissue or cavity that is contingent to the respiratory tract, in particular, the sinuses. For pulmonary administration, an aerosol formulation containing the active agent, a manual pump spray, nebulizer or pressurized metered-dose inhaler as well as dry powder formulations are contemplated. Suitable formulations of this type can also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a head space representing greater than about 15% of the total volume of the canister. Often, the compound intended for pulmonary administration is dissolved, suspended or emulsified in a mixture of a solvent, surfactant and propellant. The mixture is maintained under pressure in a canister that has been sealed with a metering valve.

As discussed above, the present invention also encompasses methods of treating a patient suffering from a condition associated with a dysfunction in proteostasis comprising administering an effective amount of a compound having the Formula (Ia), (Ib), (Ic), (Id), (Ie), (II), (IIIa), (IIIb), (IIIc), (IIId), (IVa), (IVb), (IVc), (Va), (Vb), (VIa), (VIb), (VIc), (VId), (VIe), (VII), (VIIIa), (VIIIb), (VIIIe), or (IX), or a pharmaceutically acceptable salt, prodrug, clathrate or solvate of any of thereof.

"Treating" or "treatment" includes preventing or delaying the onset of the symptoms, complications, or biochemical indicia of a disease, alleviating or ameliorating the symptoms or arresting or inhibiting further development of the disease, condition, or disorder. A "patient" is a human subject in need of treatment.

An "effective amount" refers to that amount of the therapeutic agent that is sufficient to ameliorate of one or more symptoms of a disorder and/or prevent advancement of a disorder, cause regression of the disorder and/or to achieve a desired effect.

As used herein, the term "inhibiting" or "decreasing" encompasses causing a net decrease by either direct or indirect means. The term "increasing" means to cause a net gain by either direct or indirect means.

The invention encompasses the treatment of a condition associated with a dysfunction in proteostasis. Proteostasis refers to protein homeostasis. Dysfunction in protein homeostasis is a result of protein misfolding, protein aggregation, defective protein trafficking or protein degradation. Exemplary proteins of which there can be a dysfunction in proteostasis, for example that can exist in a misfolded state, include, but are not limited to, glucocerebrosidase, hexosamine A, cystic fibrosis transmembrane conductance regulator, aspartylglucsaminidase, α-galactosidase A, cysteine transporter, acid ceremidase, acid α-L-fucosidase, protective protein, cathepsin A, acid β-glucosidase, acid β-galactosidase, iduronate 2-sulfatase, α-L-iduronidase, galactocerebrosidase, acid α-mannosidase, acid β-mannosidase, arylsulfatase B, arylsulfatase A, N-acetylgalactosamine-6-sulfate sulfatase, acid β-galactosidase, N-acetylglucosamine-1-phosphotransferase, acid sphingmyelinase, NPC-1, acid α-glucosidase, β-hexosamine B, heparin N-sulfatase, α-N-acetylglucosaminidase, α-glucosaminide N-acetyltransferase, N-acetylglucosamine-6-sulfate sulfatase, α-N-acetylgalactosaminidase, α-neuramidase, β-glucuronidase, β-hexosamine A and acid lipase, polyglutamine, α-synuclein, Ab peptide, tau protein transthyretin and insulin.

In certain embodiments, the protein is selected from the group consisting of huntingtin, tau, alpha-synuclein, α1 anti-trypsin and superoxide dismutase.

Protein conformational diseases or conditions associated with a dysfunction in proteostasis encompass gain of function disorders and loss of function disorders. In one embodiment, the protein conformational disease is a gain of function disorder. The terms "gain of function disorder," "gain of function disease," "gain of toxic function disorder" and "gain of toxic function disease" are used interchangeably herein. A gain of function disorder is a disease characterized by increased aggregation-associated proteotoxicity. In these diseases, aggregation exceeds clearance inside and/or outside of the cell. Gain of function diseases include, but are not limited to neurodegenerative diseases associated with aggregation of polyglutamine, Lewy body diseases, amyotrophic lateral sclerosis, transthyretin-associated aggregation diseases, Alzheimer's disease and prion diseases. Neurodegenerative diseases associated with aggregation of polyglutamine include, but are not limited to, Huntington's disease, dentatorubral and pallidoluysian atrophy, several forms of spino-cerebellar ataxia, and spinal and bulbar muscular atrophy. Alzheimer's disease is characterized by the formation of two types of aggregates: extracellular aggregates of Aβ peptide and intracellular aggregates of the microtubule associated protein tau. Transthyretin-associated aggregation diseases include, for example, senile systemic amyloidoses and familial amyloidotic neuropathy. Lewy body diseases are characterized by an aggregation of α-synuclein protein and include, for example, Parkinson's disease. Prion diseases (also known as transmissible spongiform encephalopathies or TSEs) are characterized by aggregation of prion proteins. Exemplary human prion diseases are Creutzfeldt-Jakob Disease (CJD), Variant Creutzfeldt-Jakob Disease, Gerstmann-Straussler-Scheinker Syndrome, Fatal Familial Insomnia and Kuru.

In a further embodiment, the protein conformation disease or the condition associated with a dysfunction in proteostasis is a loss of function disorder. The terms "loss of function disease" and "loss of function disorder" are used interchangeably herein. Loss of function diseases are a group of diseases characterized by inefficient folding of a protein resulting in excessive degradation of the protein. Loss of function diseases include, for example, cystic fibrosis and lysosomal storage diseases. In cystic fibrosis, the mutated or defective enzyme is the cystic fibrosis transmembrane conductance regulator (CFTR). One of the most common mutations of this protein is ΔF508 which is a deletion (Δ) of three nucleotides resulting in a loss of the amino acid phenylalanine (F) at the 508th (508) position on the protein. Lysosomal storage diseases are a group of diseases characterized by a specific lysosomal enzyme deficiency which may occur in a variety of tissues, resulting in the build-up of molecules normally degraded by the deficient enzyme. The lysosomal enzyme deficiency can be in a lysosomal hydrolase or a protein involved in the lysosomal trafficking Lysosomal storage diseases include, but are not limited to, aspartylglucosaminuria, Fabry's disease, Batten disease, Cystinosis, Farber, Fucosidosis, Galactasidosialidosis, Gaucher's disease (including Types 1, 2 and 3), Gm1 gangliosidosis, Hunter's disease, Hurler-Scheie's disease, Krabbe's disease, α-Mannosidosis, β-Mannosidosis, Maroteaux-Lamy's disease, Metachromatic Leukodystrophy, Morquio A syndrome, Morquio B syndrome, Mucolipidosis II, Mucolipidosis III, Neimann-Pick Disease (including Types A, B and C), Pompe's disease, Sandhoff disease, Sanfilippo syndrome (including Types A, B, C and D), Schindler disease, Schindler-Kanzaki disease, Sialidosis, Sly syndrome, Tay-Sach's disease and Wolman disease.

In some embodiments, the condition is selected from the group consisting of Huntington's disease, Alzheimer's disease, Parkinson's disease, amyotrophic lateral sclerosis, diabetic retinopathy, diabetes, and other retinal disorders.

In yet another embodiment, the disease associated with a dysfunction in proteostasis is diabetes and/or complications of diabetes, including, but not limited to, diabetic retinopathy, cardiomyopathy, neuropathy, nephropathy, and impaired wound healing.

In a further embodiment, the disease associated with a dysfunction in proteostasis is an ocular disease including, but not limited to, age-related macular degeneration (AMD), diabetic macular edema (DME), diabetic retinopathy, glaucoma, cataracts, retinitis pigmentosa (RP), and dry macular degeneration.

In some embodiments, the condition is selected from the group consisting of Huntington's disease, Alzheimer's disease, Parkinson's disease, amyotrophic lateral sclerosis, diabetes and complications thereof, ocular diseases and cancer or tumor.

The invention also encompasses methods for the treatment of hemoglobinopathies (such as sickle cell anemia), an inflammatory disease (such as inflammatory bowel disease, colitis, ankylosing spondylitis), intermediate filament diseases (such as non alcoholic and alcoholic fatty liver disease) and drug induced lung damage (such as methotrexate-induced lung damage).

In certain embodiments, the invention includes methods for the treatment of condition associated with a dysfunction in proteostasis comprising administering to a patient in need thereof a compound described herein, and a second agent (e.g., a second therapeutic agent). Co-administered agents, compounds, or therapeutics need not be administered at exactly the same time. In certain embodiments, however, a compound described herein, is administered substantially simultaneously as the second agent. By "substantially simultaneously," it is meant that the compound of the invention, is administered before, at the same time, and/or after the administration of the second agent, and encompasses, for example, administration within the same treatment session or as part of the same treatment regimen. Exemplary second agents include pharmacologic chaperones and proteostasis regulators (such as, those described below).

In an additional embodiment, the invention is directed to a pharmaceutical composition comprising a compound of Formula (Ia), (Ib), (Ic), (Id), (Ie), (II), (IIIa), (IIIb), (IIIc), (IIId), (IVa), (IVb), (IVc), (Va), (Vb), (VIa), (VIb), (VIc), (VId), (Vie), (VII), (VIIIa), (VIIIb), (VIIIe), or (IX), and a second agent, wherein the second agent is selected from the group consisting of a pharmacologic chaperone and a proteostasis regulator. The invention also encompasses a method of treating a patient suffering from a condition associated with a dysfunction in proteostasis comprising administering a therapeutically effective amount of a compound of the invention and a second agent, wherein the second agent is a pharmacologic chaperone. Pharmacologic chaperones or kinetic stabilizers refer to compounds that bind an existing steady state level of the folded mutant protein and chemically enhance the folding equilibrium by stabilizing the fold [Bouvier, *Chem Biol* 14: 241-242, 2007; Fan et al., *Nat Med* 5: 112-115, 1999; Sawkar et al., *Proc Natl Acad Sci USA* 99:15428-15433, 2002; Johnson and Kelly, *Accounts of Chemical Research* 38: 911-921, 2005]. The pharmacologic chaperone is administered in amount that in combination with a compound described herein in an amount that is sufficient to treat a patient suffering from a condition associated with a dysfunction in proteostasis. Exemplary pharmacologic chaperones are described in U.S. Patent Application Publication No's. 20080056994, 20080009516, 20070281975, 20050130972, 20050137223, 20050203019, 20060264467 and 20060287358, the contents of which are incorporated by reference herein. The term "proteostasis regulator" refers to small molecules, siRNA and biologicals (including, for example, proteins) that enhance cellular protein homeostasis. For example, proteostasis regulators can be agents that influence protein synthesis, folding, trafficking and degradation pathways. Proteostasis regulators encompass pharmacologic agents that stimulate the HSR signaling activity. Proteostasis regulators function by manipulating signaling pathways, including, but not limited to, the heat shock response or the unfolded protein response, or both, resulting in transcription and translation of proteostasis network components. Proteostasis regulators can enhance the folding, trafficking and function of proteins (for example, mutated proteins). Proteostasis regulators can also regulate protein chaperones by upregulating transcription or translation of the protein chaperone, or inhibiting degradation of the protein chaperone. Proteostasis regulators can influence the biology of folding, often by the coordinated increase in chaperone and folding enzyme levels and macromolecules that bind to partially folded conformational ensembles, thus enabling their progression to intermediates with more native structure and ultimately increasing the concentration of folded mutant protein for export. In one aspect, the proteostasis regulator is distinct from a chaperone in that the proteostasis regulator can enhance the homeostasis of a mutated protein but does not bind the mutated protein. In addition, proteostasis regulators can upregulate an aggregation pathway or a disaggregase activity. Exemplary proteostasis regulators are the celastrols, MG-132 and L-type $Ca^{2+}$ channel blockers (e.g., dilitiazem and verapamil). The term "celastrols" refers to celastrol and derivatives or analogs thereof, including, but not limited to, those celastrol derivatives described in Westerheide et al., *J Biol Chem*, 2004. 279(53): p. 56053-60, the contents of which are expressly incorporated by reference herein. Celastrol derivatives include, for example, celastrol methyl ester, dihydrocelastrol diacetate, celastrol butyl ether, dihydrocelastrol, celastrol benzyl ester, primesterol, primesterol diacetate and triacetate of celastrol. In certain aspects, the proteostasis regulator is a heat shock response activator. A heat shock response activator is an agent that indirectly or directly activates the heat shock response, for example, by directly or indirectly activating heat shock transcription factor 1 (HSF1), inhibiting Hsp90, and/or activating chaperone expression (Westerheide et al., J Biol Chem, 2004. 279(53): p. 56053-60, the contents of which are expressly incorporated by reference herein). The terms "heat shock response activator," "heat shock activator," "heat shock response inducer," and "heat shock inducer" are used interchangeably herein. Non-limiting examples of heat shock response activators are celastrols, non-steroidal antiinflammatory drugs, ansamycin, geldenamycin, radiciol, glucuronic acid, and tributylin. Heat shock response activators have also been described, for example, in U.S. Patent Application Publication No's. 20070259820, 20070207992, 20070179087, 20060148767, the contents of each of which are expressly incorporated by reference herein. In some embodiments, the heat shock response activator is a small molecule heat shock response activator.

The invention also encompasses a method of treating cancer or a tumor in a patient in need thereof comprising administering to said patient an effective amount of a compound described herein. Cancers that can be treated according to methods of the present invention include, but are not limited to, breast cancer, colon cancer, pancreatic cancer, prostate cancer, lung cancer, ovarian cancer, cervical cancer, multiple myeloma, basal cell carcinoma, neuroblastoma, hematologic cancer, rhabdomyosarcoma, liver cancer, skin cancer, leukemia, basal cell carcinoma, bladder cancer, endometrial cancer, glioma, lymphoma, and gastrointestinal cancer.

In another embodiment, the invention is a method of treating cancer or a tumor comprising administering an effective amount of a compound described herein in combination with the administration of a chemotherapeutic agent. Chemotherapeutic agents that can be utilized include, but are not limited to, alkylating agents such as cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

In a further embodiment, the invention is a method of treating cancer or a tumor comprising administering to a patient in need thereof an effective amount of a compound described herein in combination with radiation therapy.

The invention is illustrated by the following examples which are not meant to be limiting in any way.

EXEMPLIFICATION

Example 1

Synthesis of 1-[1-(4-Chloro-phenyl)-2,5-dimethyl-1H-pyrrol-3-yl]-2-cyclopentyl-ethanone (A1) and 1-[1-(4-Chloro-phenyl)-2,5-dimethyl-1H-pyrrol-3-yl]-2cyclohexyl-ethanone (A2)

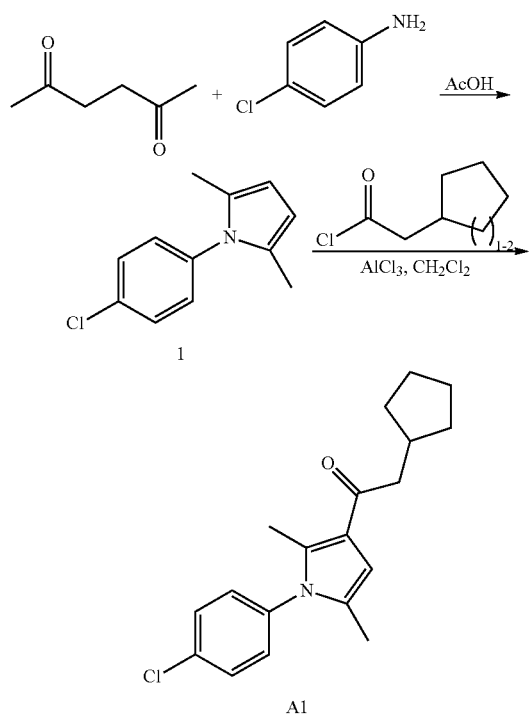

1-[1-(4-Chloro-phenyl)-2,5-dimethyl-1H-pyrrol-3-yl]-2-cyclopentyl-ethanone (A1)

Step 1: 4-Chloroaniline (10.0 g, 78 mmol) was placed in a 500 mL roundbottom flask. Methanol (200 mL), hexane-2,5-dione (9.20 mL, 78 mmol) and glacial acetic acid (4.60 mL, 78 mmol) were added to the flask and the reaction was heated to 50° C. overnight. The mixture was then cooled to room temperature and the methanol was removed under reduced pressure. The red residue was taken up in EtOAc and washed twice with saturated $NaCO_3$ and once with brine. The organic layer was dried over $MgSO_4$ and concentrated. The material was then adsorbed onto silica gel and purified using a Biotage Flashmaster (100 g silica gel column, 2% EtOAc in hexanes). 1-(4-chlorophenyl)-2,5-dimethyl-1H-pyrrole (1) was isolated as a white solid (14 g, 68 mmol, 87% yield). $^1$H NMR (400 MHz, $CDCl_3$) δ ppm=7.44-7.41 (m, 2H), 7.16-7.14 (d, 2H), 5.90 (s, 2H), 2.02 (s, 6H); low resolution mass spectrum (ES+) m/z 206 ([M+H]$^+$); calcd for $C_{12}H_{12}ClN+H$, 206]. Step 2: To a stirred suspension of anhydrous $AlCl_3$ (1 g, 7.2 mmol), in dry DCM 20 mL of cyclopentyl acetyl chloride (0.52 g, 3.89 mmol) was added and stirred for 30 min at room temperature under inert atmosphere. The reaction mass was cooled to 0° C. and pyrrole (1) (1 g, 4.86 mmol) was added in single portion and stirring was continued for 1 h Progress of the reaction was monitored by TLC. After completion of the reaction the mixture was poured onto ice water (~50 g) and extracted with EtOAc (3×30 mL). Crude material obtained after evaporating organic phase was purified by preparative HPLC method to give A1 (0.07 g, 0.22 mmol, 4% yield). $^1$H NMR (400 MHz, $CDCl_3$) δ ppm=7.47-7.45 (d, 2H), 7.12-7.10 (d, 2H), 6.31 (s, 1H), 2.75-2.73 (d, 2H), 2.40-2.32 (m, 1H), 2.29 (s, 3H), 1.97 (s, 3H), 1.88-1.83 (m, 2H), 1.62-1.49 (m, 4H), 1.23-1.13 (m, 2H); low resolution mass spectrum (ES+) m/z 315.9 ([M+H]$^+$); calcd for $C_{19}H_{22}ClNO+H$, 316.1].

1-[1-(4-Chloro-phenyl)-2,5-dimethyl-1H-pyrrol-3-yl]-2cyclohexyl-ethanone (A2)

(0.8 g, 0.24 mmol, 5% yield). $^1$H NMR (400 MHz, $CDCl_3$) δ ppm=7.47-7.45 (dd, 2H), 7.12-7.10 (dd, 2H), 6.30 (s, 1H), 2.59-2.57 (d, 2H), 2.29 (s, 3H), 1.97 (s, 3H), 1.95-1.89 (m, 1H), 1.78 (m, 2H), 1.74-1.62 (m, 3H), 1.33-1.23 (m, 2H), 1.19-1.12 (m, 1H), 1.06-0.95 (m, 2H); low resolution mass spectrum (ES+) m/z 330.3 ([M+H]$^+$); calcd for $C_{20}H_{24}ClNO+H$, 330.2].

Example 2

Synthesis of 1-(1-(4-chlorophenyl)-2,5-dimethyl-1H-pyrrol-3-yl)-2,2-difluoroethanone (A3)

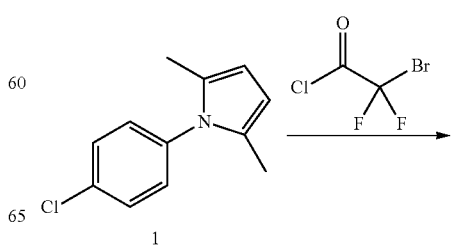

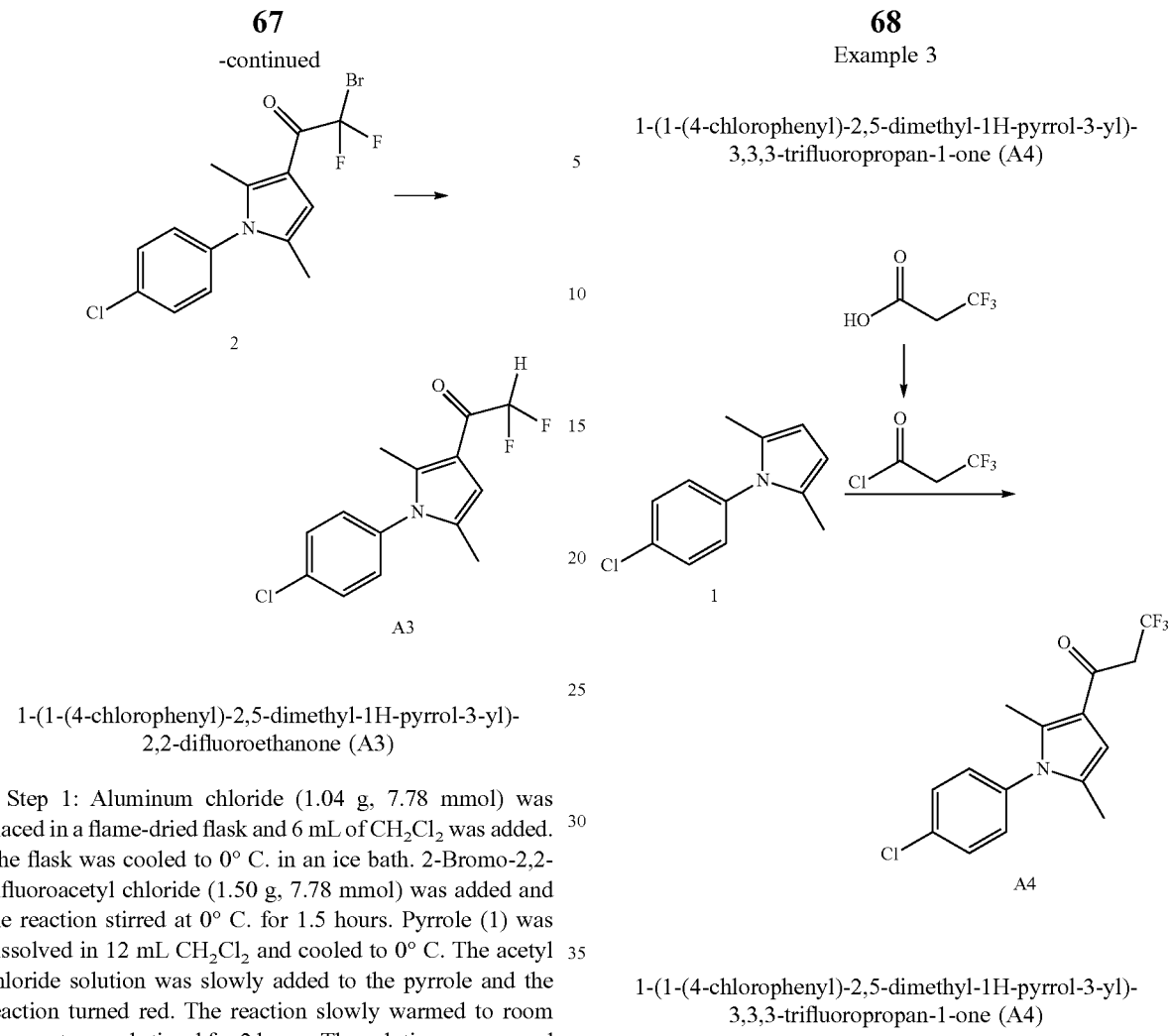

Example 3

1-(1-(4-chlorophenyl)-2,5-dimethyl-1H-pyrrol-3-yl)-3,3,3-trifluoropropan-1-one (A4)

1-(1-(4-chlorophenyl)-2,5-dimethyl-1H-pyrrol-3-yl)-2,2-difluoroethanone (A3)

Step 1: Aluminum chloride (1.04 g, 7.78 mmol) was placed in a flame-dried flask and 6 mL of $CH_2Cl_2$ was added. The flask was cooled to 0° C. in an ice bath. 2-Bromo-2,2-difluoroacetyl chloride (1.50 g, 7.78 mmol) was added and the reaction stirred at 0° C. for 1.5 hours. Pyrrole (1) was dissolved in 12 mL $CH_2Cl_2$ and cooled to 0° C. The acetyl chloride solution was slowly added to the pyrrole and the reaction turned red. The reaction slowly warmed to room temperature and stirred for 2 hours. The solution was poured into ice and diluted with $CH_2Cl_2$. The layers were separated and the aq. phase was extracted once with $CH_2Cl_2$. The combined organics were washed with brine and dried over $MgSO_4$. The solution was adsorbed onto silica and purified using flash chromatography. 2-Bromo-1-(1-(4-chlorophenyl)-2,5-dimethyl-1H-pyrrol-3-yl)-2,2-difluoroethanone (2) was isolated as a light brown solid (1.2 g, 3.31 mmol, 68% yield). $^1$H NMR (300 MHz, $CDCl_3$) δ ppm 7.53 (m, 2H), 7.16 (m, 2H), 6.50 (s, 1H), 2.35 (s, 3H), 2.00 (s, 3H); low resolution mass spectrum (ES+) m/z 363.9 ([M+H$^+$]; calcd for $C_{14}H_{11}Br^{81}Cl^{35}F_2NO+H$, 364]. Step 2: A flask was charged with NaH (0.058 g, 1.45 mmol) followed by THF (2 mL). Pyrrolidine (0.12 mL, 1.46 mmol) was added at room temperature. After 30 min 2 (0.44 g, 1.21 mmol) was added and the reaction stirred at room temperature overnight. The reaction was diluted with EtOAc and water. The layers were separated and the organic phase was washed with brine then dried over $MgSO_4$. The solvent was removed under reduced pressure to give a yellow oil. The oil was purified using flash chromatography. Compound (A3) was isolated as a light brown solid (13 mg, 0.046 mmol, 3.8% yield). $^1$H NMR (300 MHz, $CDCl_3$) δ ppm 7.51 (m, 2H), 7.14 (m, 2H), 6.50 (s, 1H), 6.07 (t, J=54 Hz, 1), 2.34 (s, 3H), 2.00 (s, 3H); low resolution mass spectrum (ES+) m/z 284.0 ([M+H$^+$]; calcd for $C_{14}H_{12}ClF_2NO+H$, 284.0].

1-(1-(4-chlorophenyl)-2,5-dimethyl-1H-pyrrol-3-yl)-3,3,3-trifluoropropan-1-one (A4)

Step 1: 3,3,3-Trifluoropropanoic acid (0.70 mL, 7.81 mmol) was taken up in 12 mL of dry $CH_2Cl_2$ and anhydrous DMF (0.1 mL, 1.3 mmol) was added. Thionyl chloride (2.8 mL, 39 mmol) was added and the reaction stirred overnight. The following day the solvent was removed and the resulting oil was stored under nitrogen until needed. Aluminum chloride (0.97 g, 1.62 mmol) was added to a flame-dried flask and suspended in 4 mL of anhydrous $CH_2Cl_2$. The solution was cooled to 0° C. and the previously prepared acid chloride was added as a solution in 3 mL of dry $CH_2Cl_2$. After stirring for 1.5 hours the acid chloride solution was added to a chilled solution of pyrrole (1) in 5 mL of dry $CH_2Cl_2$. The reaction turned bright yellow then darkened. The reaction warmed slowly to room temperature. After two hours the reaction mixture was poured into ice. After the ice melted the layers were separated and the aqueous phase was extracted three times with dichloromethane. The organic phase was washed with saturated $NaHCO_3$, water then brine and was dried and concentrated to give a red/green oil. The material was purified using flash silica gel chromatography (95:5 hex:EtOAc). One fraction was isolated as a brown oil. The oil was crystallized from hot EtOAc and hexanes to give A4 as a brown solid (26 mg, 0.08 mmol, 1.8% yield). $^1$H NMR (300 MHz, $CDCl_3$) δ ppm 7.50 (m, 2H), 7.13 (m, 2H), 6.26 (s, 1H), 3.54 (q, J=10.5 Hz, 2H), 2.32 (s, 3H), 1.99 (s, 3H); low resolution mass spectrum (ES+) m/z 316.0 ([M+H$^+$]; calcd for $C_{15}H_{13}ClF_3NO+H$, 316.1].

Example 4

Synthesis of 2-(1-(4-chlorophenyl)-2,5-dimethyl-1H-pyrrol-3-yl)-2-oxoacetic acid (A5), 1-(1-(4-chlorophenyl)-2,5-dimethyl-1H-pyrrol-3-yl)-2-(4-hydroxypiperidin-1-yl)ethane-1,2-dione (A6) and 1-(1-(4-chlorophenyl)-2,5-dimethyl-1H-pyrrol-3-yl)-2-(4-fluoropiperidin-1-yl)ethane-1,2-dione (A7)

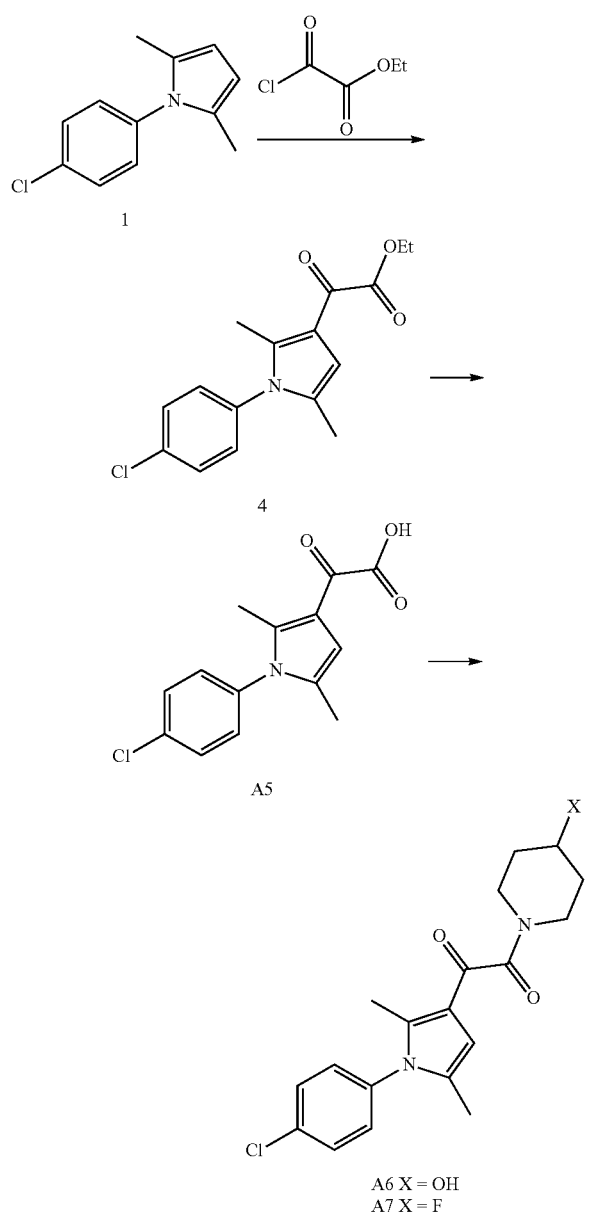

2-(1-(4-chlorophenyl)-2,5-dimethyl-1H-pyrrol-3-yl)-2-oxoacetic acid (A5)

Step 1: Pyrrole 1 was treated with ethyl oxalylchloride (see preparation of A3 for procedure). Ethyl 2-(1-(4-chlorophenyl)-2,5-dimethyl-1H-pyrrol-3-yl)-2-oxoacetate (4) was isolated in 67% yield. $^1$H NMR (300 MHz, CDCl$_3$) δ 7.51 (m, 2H), 7.14 (m, 2H), 6.45 (s, 1H), 4.40 (q, J=7.2 Hz, 2H), 2.34 (s, 3H), 1.98 (s, 3H) 1.42 (t, J=7.2 Hz, 3H). Step 2: Ester (4 (1.0 g, 3.27 mmol) was taken up in 10 mL of MeOH. Solid NaOH (5 eq.) was added followed by 5 mL of water. The reaction stirred over night at room temperature. The reaction mixture was acidified with 1 N HCl and the aq. phase was extracted twice with EtOAc. The combined organic extracts were washed with brine the dried over MgSO$_4$. The solution was concentrated to give A5 as a brown solid (0.4 g, 1.42 mmol, 42% yield). $^1$H NMR (300 MHz, CDCl$_3$) δ ppm 7.52 (m, 2H), 7.15 (m, 3H), 2.36 (s, 3H), 1.98 (s, 3H); $^{13}$C NMR (75 MHz, CDCl$_3$) δ 177.8, 162.0, 135.6, 135.3, 130.9, 130.3 (2H), 129.3 (2H), 115.5, 110.8, 14.0, 12.9; low resolution mass spectrum (ES+) m/z 232.0 ([M−CO$_2$$^+$]; calcd for C$_{13}$H$_{11}$ClNO$^+$ 232.1].

1-(1-(4-chlorophenyl)-2,5-dimethyl-1H-pyrrol-3-yl)-2-(4-hydroxypiperidin-1-yl)ethane-1,2-dione (A6)

PyBOP (0.41 g, 0.73 mmol) and acid (A5) (0.20 g, 0.72 mmol) were placed in a flame-dried flask and taken up in 3 mL of dry DMF. 4-Methylmorpholine (0.09 mL, 0.73 mmol) was added and the reaction stirred for 5 min before the addition of piperidine (0.07 mL, 0.72 mmol). The reaction stirred overnight at room temperature. The reaction mixture was poured into 100 mL water and extracted twice with EtOAc. The combined organic phases were washed once with 1 N HCl, once with water and once with brine. The solution was dried over MgSO$_4$ and concentrated to give a brown oil. The oil was purified using flash chromatography (1:1 hexanes:EtOAc). A yellow oil was collected and crystallized from hexanes and EtOAc to give A6 as a white solid (120 mg, 0.34 mmol, 47% yield). $^1$H NMR (300 MHz, CDCl$_3$) δ ppm 7.49 (m, 2H), 7.13 (m, 2H), 6.25 (s, 1H), 3.66 (m, 2H), 3.40 (m, 2H), 2.32 (s, 3H), 1.95 (s, 3H), 1.68 (m, 6H); low resolution mass spectrum (ES+) m/z 232.0 ([M−C$_6$H$_{10}$ON)$^+$]; calcd for C$_{13}$H$_{11}$ClNO$^+$ 232.1].

1-(1-(4-chlorophenyl)-2,5-dimethyl-1H-pyrrol-3-yl)-2-(4-fluoropiperidin-1-yl)ethane-1,2-dione (A7)

$^1$H NMR (300 MHz, CDCl$_3$) δ ppm 7.49 (m, 2H), 7.13 (m, 2H), 6.26 (s, 1H), 4.93 (m, 1H), 4.03 (ddd, J=4.8, 4.8, 13.5 Hz, 1H), 3.53 (m, 3H), 2.33 (s, 3H), 1.95 (s, 3H), 2.02-1.85 (m, 4H); ([M−C6H9FON)$^+$]; calcd for C$_{13}$H$_{11}$ClNO$^+$ 232.1].

Example 5

Synthesis of 2-chloro-1-(1-(4-chlorophenyl)-2,5-dimethyl-1H-pyrrol-3-yl)ethanone (A8)

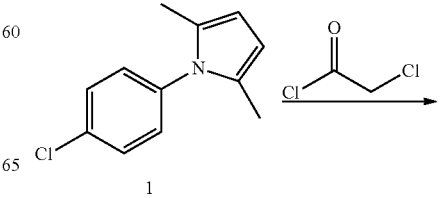

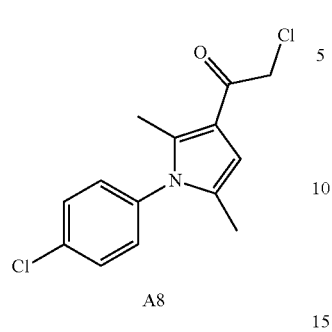

A8

2-chloro-1-(1-(4-chlorophenyl)-2,5-dimethyl-1H-pyrrol-3-yl)ethanone (A8)

Aluminum chloride (7.42 g, 55.6 mmol) was placed in a dry flask and 10 mL of dry $CH_2Cl_2$ was added. The reaction cooled to 0° C. and 2-chloro-acetyl chloride (4.42, 55.6 mmol) was added. Pyrrole (1) (7.18 g, 34.8 mmol) was placed in a flask and taken up in 20 mL dry $CH_2Cl_2$. The solution was cooled to 0° C. After 1.5 hours the acid chloride mixture was added to the pyrrole solution. After stirring at 0° C. for 30 min. the reaction was poured onto ice. After the ice melted the layers were separated and the aq. phase was extracted twice with $CH_2Cl_2$. The combined layers were washed with brine, dried over $MgSO_4$ and adsorbed onto silica gel. The material was purified using silica gel chromatography (95:5 hexanes:EtOAc). Chloride (A8) was isolated as a white $^1$H NMR (300 MHz, $CDCl_3$) δ ppm 7.49 (m, 2H), 7.13 (m, 2H), 6.30 (s, 1H), 4.47 (s, 2H), 2.31 (s, 3H), 1.99 (s, 3H); low resolution mass spectrum (ES+) m/z 281.94 [(M+H$^+$); calcd for $C_{14}H_{13}Cl_2NO+H$, 282.04]. solid (3.11 g, 10.5 mmol, 30% yield).

Example 6

Synthesis of 1-[1-(4-Chloro-phenyl)-2,5-dimethyl-1H-pyrrol-3-yl]-2-pyrrol-1-yl-ethanone (A9) and 1-[1-(4-Chloro-phenyl)-2,5-dimethyl-1H-pyrrol-3-yl]-2-imidazol-1-yl-ethanone (A10)

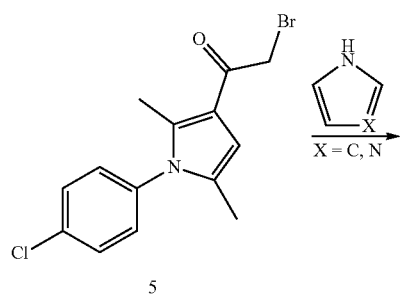

5

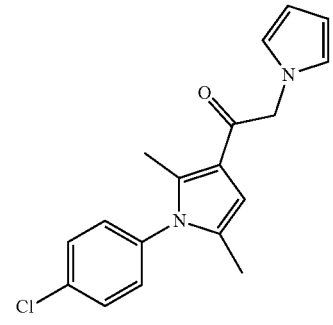

A9

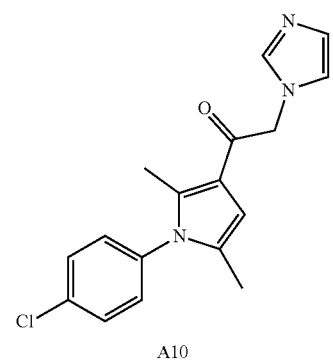

A10

1-[1-(4-Chloro-phenyl)-2,5-dimethyl-1H-pyrrol-3-yl]-2-pyrrol-1-yl-ethanone (A9)

Compound 5 was prepared from pyrrole 1 and bromoacetyl chloride according to the procedure used to prepare A8. Bromide 5 (0.6 g, 0.0018 mol) and pyrrole (0.123 g, 0.0018 mol) were dissolved in 8 mL of anhydrous DMF and to this solution was added $CsCO_3$ (1.19 g, 0.0036 mol). The resulting mixture was stirred for 3 h at ambient temperature and monitored by TLC. After completion of the reaction, the mixture was diluted with 10 mL water and extracted with DCM (3×25 mL). The organic layer was separated, dried over $Na_2SO_4$ and evaporated under vacuum to get crude material which was purified by preparative HPLC to afford the title compound (A9) as an off white solid (53 mg, 0.17 mmol, 9.5% yield). $^1$H NMR ($CDCl_3$): δ=7.49-7.47 (m, 2H), 7.12-7.10 (m, 2H), 6.68-6.67 (m, 2H), 6.26 (br, 1H), 6.22-6.21 (m, 2H), 5.04 (s, 2H), 2.29 (s, 3H), 1.98 (s, 3H); low resolution mass spectrum (ES+) m/z 313.2 ([M+H]$^+$); calcd for $C_{18}H_{17}ClN_2O+H$, 313.1].

1-[1-(4-Chloro-phenyl)-2,5-dimethyl-1H-pyrrol-3-yl]-2-imidazol-1-yl-ethanone (A10)

Following the procedure used for A9, compound A10 was isolated in 39% yield (300 mg, 0.95 mmo). $^1$H NMR ($CDCl_3$): δ=8.61-8.59 (m. 1H), 7.52-7.48 (m, 2H), 7.32 (br, 1H), 7.14-7.10 (m, 3H), 6.34 (s, 1H), 5.34 (s, 2H), 2.28 (s, 3H), 2.0 (s, 3H); low resolution mass spectrum (ES+) m/z 314 ([M+H]$^+$); calcd for $C_{17}H_{16}ClN_3O+H$, 314.1].

Example 7

Synthesis of 2-(piperidin-1-yl)-1-(1,2,5-trimethyl-1H-pyrrol-3-yl)ethanone (A11): and 2-(pyrrolidin-1-yl)-1-(1,2,5-trimethyl-1H-pyrrol-3-yl)ethanone (A12)

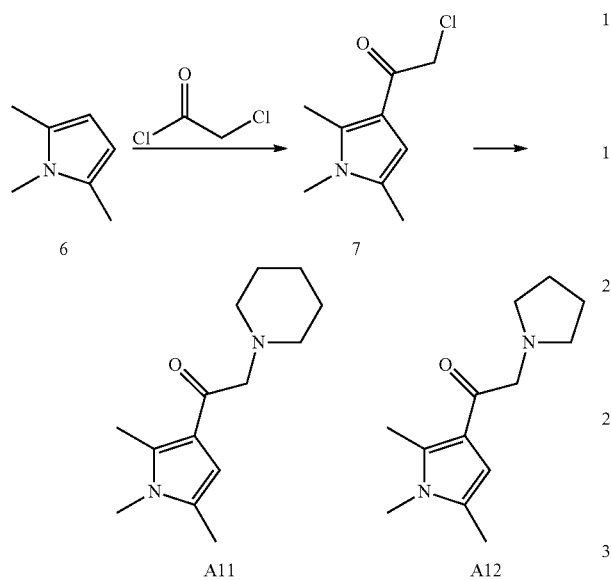

2-(piperidin-1-yl)-1-(1,2,5-trimethyl-1H-pyrrol-3-yl)ethanone (A11): Step 1

Aluminum chloride (3.9 g, 29.3 mmol) was taken up in 12 mL of $CH_2Cl_2$ and cooled to 0° C. in an ice bath. Chloroacetyl chloride (2.33 mL, 29.3 mmol) was added and the reaction stirred at 0° C. for 30 min. 1,2,5-Trimethyl-1H-pyrrole (6) (2.0 g, 18.3 mmol) was dissolved in 6 mL of $CH_2Cl_2$ and cooled to 0° C. The chloride solution was added via syringe and the reaction turned red immediately. The reaction warmed to room temp over 1.5 hours. The reaction was poured into ice. The layers were separated and the aq. phase was extracted with $CH_2Cl_2$. The combined organic phases were then washed sequentially with water, saturated $NaHCO_3$ and brine. The solution was dried over $MgSO_4$ and concentrated. The red oil was adsorbed onto silica and purified by column chromatography. The compound came off as colorless but turned dark red on concentration and gave a dark red solid. 2-Chloro-1-(1,2,5-trimethyl-1H-pyrrol-3-yl)ethanone (7) was isolated in 15% yield (0.053 g, 2.85 mmol). $^1$H NMR (300 MHz, $CDCl_3$) δ 6.18 (s, 1H), 4.43 (s, 2H), 3.41 (s, 3H), 2.55 (s, 3H), 2.21 (s, 3H); low resolution mass spectrum (ES+) m/z 186.11 [M+H$^+$]; calcd for $C_9H_{12}ClNO+H$, 186.1]. Step 2: Chloride (7) (0.25 g, 1.35 mmol) was placed in a 50 mL flask and dissolved in 2 mL of HPLC grade acetonitrile. Piperidine (0.13 mL, 1.35 mmol) and triethylamine (0.37 mL, 2.7 mmol) were added to the flask and the reaction stirred overnight. The solvent was removed under reduced pressure and the resulting solid was taken up in $CH_2Cl_2$. The organic phase was washed with water and brine then dried over $MgSO_4$. The compound was adsorbed onto silica gel and the product was eluted from a 25 g Biotage silica gel cartridge using 95:5 $CH_2Cl_2$:MeOH. A brown solid was isolated. The material was crystallized from EtOAc and hexanes. A beige solid formed and was removed by filtration to give 5 mg of material. The filtrate was concentrated down to give 2-(piperidin-1-yl)-1-(1,2,5-trimethyl-1H-pyrrol-3-yl)ethanone (A11) as a beige solid (73 mg 0.29 mmol, 22% yield). $^1$H NMR (300 MHz, $CDCl_3$) δ ppm 6.26 (s, 1H), 3.54 (s, 2H), 3.39 (s, 3H), 2.54 (m, 7H), 2.19 (s, 3H), 1.66 (m, 4H); low resolution mass spectrum (ES+) m/z 235.16 [M+H)$^+$; calcd for $C_{14}H_{22}ClN_2O+H$, 235.17].

2-(pyrrolidin-1-yl)-1-(1,2,5-trimethyl-1H-pyrrol-3-yl)ethanone (A12)

Following the procedure used to prepare A11 compound A12 was isolated. $^1$H NMR (300 MHz, $CDCl_3$) δ ppm 6.10 (s, 1H), 4.34 (s, 2H), 3.72 (m, 2H), 3.41 (s, 3H) 3.37 (m, 2H), 2.53 (m, 7H), 2.21 (m, 4H) 2.19 (s, 3H); low resolution mass spectrum (ES+) m/z 221.18 [(M+H)$^+$; calcd for $C_{13}H_{20}ClN_2O+H$, 221.16].

Example 8

Synthesis of 1-[3-(4-Chloro-phenyl)-2-methyl-cyclopenta-1,4-dienyl]-2-piperidin-1-yl-ethanone (A13), 1-[1-(4-Chloro-phenyl)-5-methyl-1H-pyrazol-4-yl]-2-pyrrolidin-1-yl-ethanone (A14) and 1-[1-(4-Chloro-phenyl)-5-methyl-1H-pyrazol-4-yl]-2-(cyclopropyl-methyl-amino)-ethanone (A15)

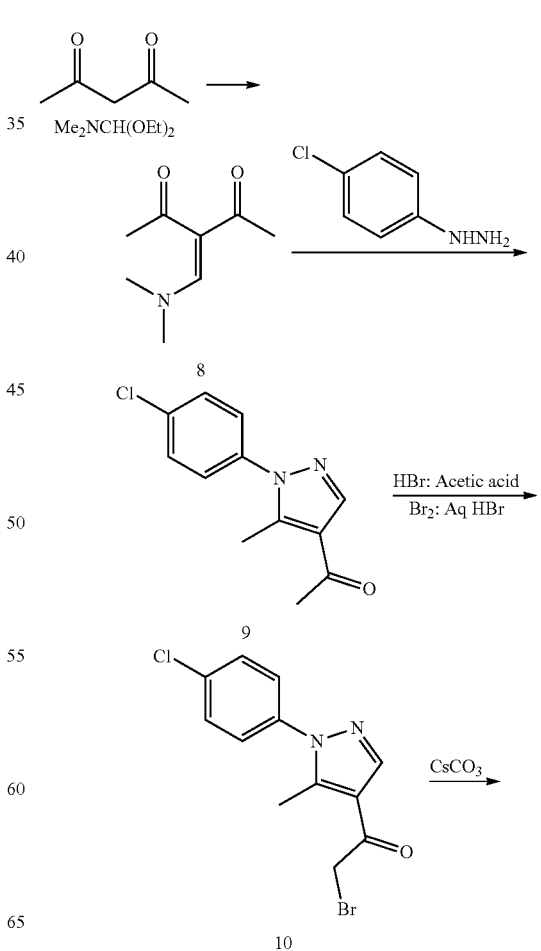

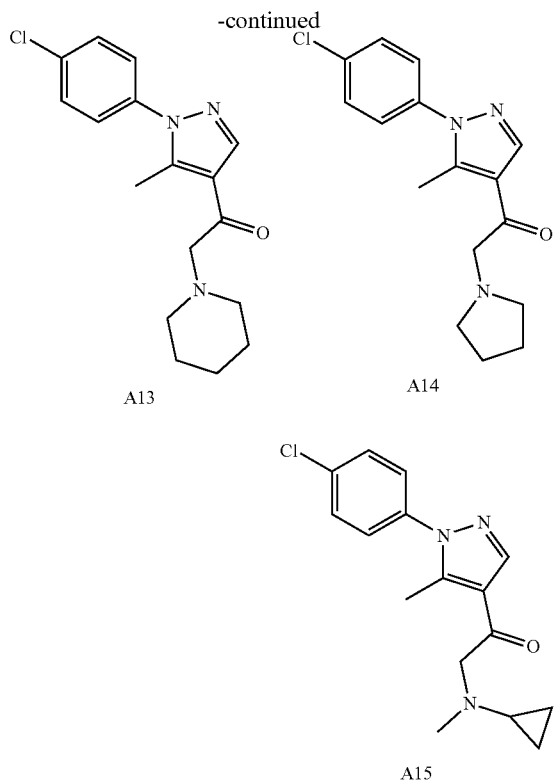

1-[3-(4-Chloro-phenyl)-2-methyl-cyclopenta-1,4-dienyl]-2-piperidin-1-yl-ethanone (A13)

Step 1: A mixture of pentane-2,5-dione (1 g, 0.01 mol) and N,N-dimethyl formamide diethyl acetal (1.47 g, 0.01 mol) were stirred and heated at 100° C. for 2 h and progress was monitored by TLC. After completion of the reaction, the mixture was subjected to (100-200 mesh) silica gel column chromatography using 10% methanol in DCM eluting system. Fractions containing pure compound were concentrated on a rotary evaporator to give 3-dimethylaminomethylene-pentane-2,4-dione 8 as a yellow solid (1 g, 6.4 mmol, 64% yield). $^1$H NMR (400 MHz, CDCl$_3$): δ ppm=7.41 (s, 1H), 2.96 (br, 6H), 2.29 (s, 6H); low resolution mass spectrum (ES+) m/z 155.9 ([M+H]$^+$); calcd for C$_8$H$_{13}$NO$_2$+H, 156.1]. Step 2: A 50 mL single neck RBF was charged with compound 8 (1 g, 0.0064 mol), 1.5 mL of acetic acid and 3 mL t-BuOH. This mixture was stirred for 5 minutes and to it was added a solution of p-chloro phenyl hydrazine (1.007 g, 0.0070 mol) in 7 mL of t-BuOH under nitrogen atmosphere at room temperature. The reaction was then heated to reflux for 1 h and monitored by TLC. After completion of the reaction, the solvent was distilled off under vacuum, and crude material was purified using silica gel (60-120 mesh) column chromatography (15% EtOAc in hexanes). The desired compound, 1-[3-(4-chloro-phenyl)-2-methyl-cyclopenta-1,4-dienyl]-ethanone (9) was isolated in 66% yield (1 g, 4.3 mmol). $^1$H NMR (400 MHz, CDCl$_3$): δ ppm=7.99 (s, 1H), 7.49-7.45 (m, 2H), 7.37-7.33 (m, 2H), 2.56 (s, 3H), 2.48 (s, 3H); low resolution mass spectrum (ES+) m/z 235.0 ([M+H]$^+$); calcd for C$_{12}$H$_{11}$ClN$_2$O+H, 235.1]. Step 3: A mixture of compound 9 (0.2 g, 0.00341 mol) and 33% HBr in acetic acid (2 mL) was heated to 70° C. for 5 min. A solution of liquid bromine (0.082 g, 0.001 mol) in 1 mL of 48% aqueous HBr was added and the reaction was continued further for 3 h. Progress of the reaction was monitored by TLC. After completion of the reaction the mixture was cooled to room temperature. The mixture was then quenched with 5 mL of ice water and basified with saturated NaHCO$_3$ solution. The aqueous layer was extracted with ethyl acetate (3×15 mL). The organic layer was then separated, dried over Na$_2$SO$_4$ and concentrated to get crude material, which then chromatographed on silica gel (100-200 mesh) using 10% ethyl acetate in hexane as eluting system to afford 2-bromo-1-[3-(4-chloro-phenyl)-2-methyl-cyclopenta-1,4-dienyl]-ethanone 10 in reasonably pure form (0.15 g, 0.47 mmol, 37% yield). $^1$H NMR (400 MHz, CDCl$_3$): δ ppm=8.06 (s, 1H), 7.50-7.47 (m, 2H), 7.38-7.36 (m, 2H), 4.24 (s, 2H), 2.59 (s, 3H); low resolution mass spectrum (ES+) m/z 314.9 ([M+H]$^+$); calcd for C$_{12}$H$_{10}$Br$^{81}$Cl$^{35}$N$_2$O+H, 315.0]. Step 4: To a stirred solution of compound 10 (0.8 g, 0.00255 mol) in 8 mL of anhydrous DMF, were added Cs$_2$CO$_3$ (1.6 g, 0.0051 mol) and piperidine (0.217 g, 0.00255 mol) respectively and reaction mixture was stirred for 2 h at ambient temperature under inert atmosphere. Progress of reaction was monitored by TLC. After completion of the reaction, mixture was diluted with 10 mL of water and product was extracted with ethyl acetate (3×10 mL). The organic layer was separated, dried over Na$_2$SO$_4$ and concentrated on rotary evaporator to get crude material, which was further purified by combiflash companion column chromatographic technique to afford the title compound A13 as pale yellow solid (0.3 mg, 0.94 mmol, 37% yield). $^1$H NMR (400 MHz, CDCl$_3$): δ ppm=8.27 (s, 1H), 7.48-7.45 (m, 2H), 7.37-7.35 (m, 2H), 3.51 (s, 2H), 2.56 (s, 3H), 2.51-2.48 (m, 4H), 1.65-1.59 (m, 4H), 1.46-1.41 (m, 2H); low resolution mass spectrum (ES+) m/z 318.0 ([M+H]$^+$); calcd for C$_{17}$H$_{20}$ClN$_3$O+H, 318.1].

1-[1-(4-Chloro-phenyl)-5-methyl-1H-pyrazol-4-yl]-2-pyrrolidin-1-yl-ethanone (A14)

Following the procedure used for A13, compound A14 was isolated as a white solid (0.3 g, 0.99 mmol 33% yield). $^1$H NMR (400 MHz, DMSO): δ ppm=8.31 (s, 1H), 7.64-7.61 (m, 2H), 7.59-7.57 (m, 2H), 3.70 (s, 2H), 2.57-2.54 (m, 4H), 2.51 (s, 3H), 1.71-1.68 (m, 4H), 1.46-1.41 (m, 2H); low resolution mass spectrum (ES+) m/z 304.2 ([M+H]$^+$); calcd for C$_{16}$H$_{18}$ClN$_3$O+H, 304.1].

1-[1-(4-Chloro-phenyl)-5-methyl-1H-pyrazol-4-yl]-2-(cyclopropyl-methyl-amino)-ethanone (A15)

Following the procedure used for A13, compound A15 was isolated as a white solid (0.25 g, 0.88 mmol, 51% yield). $^1$H NMR (400 MHz, DMSO): δ ppm=8.12 (s, 1H), 7.48-7.45 (m, 2H), 7.37-7.33 (m, 2H), 3.75 (s, 2H), 2.56 (s, 3H), 2.46 (s, 3H), 1.96-1.92 (m, 1H), 0.50-0.48 (m, 4H); low resolution mass spectrum (ES+) m/z 304.0 ([M+H]$^+$); calcd for C$_{16}$H$_{18}$ClN$_3$O+H, 304.1].

Example 9

Synthesis of 2-Diisopropylamino-1-[1-(4-fluoro-phenyl)-5-methyl-1H-pyrazol-4-yl]-ethanone (A16) and 1-[1-(4-Fluoro-phenyl)-5-methyl-1H-pyrazol-4-yl]-2-pyrrolidin-1-yl-ethanone (A17)

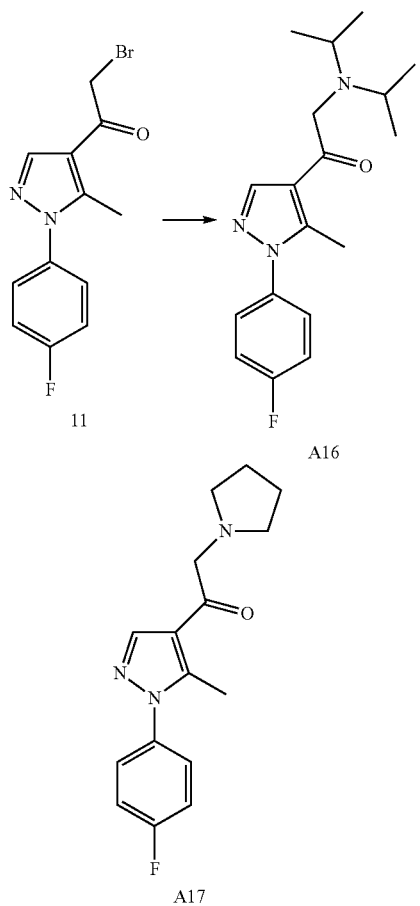

A16

A17

2-Diisopropylamino-1-[1-(4-fluoro-phenyl)-5-methyl-1H-pyrazol-4-yl]-ethanone (A16)

Compound 11 was prepared using the procedure described for compound 10. To a stirring solution of compound 11 (0.150 g, 0.0005 mol) in 1,4-dioxane (5 mL), was added slowly diisopropyl amine (0.07 mol) and the resulting mixture was then heated to reflux under nitrogen atmosphere for 30 min. Progress of the reaction was monitored by TLC. After completion of the reaction the reaction mixture was poured on to ice-water solution (50 mL), stirred for some time and then extracted well with ethyl acetate (2×50 mL). The combined organic layers was washed once with brine (30 mL), dried over anhydrous $Na_2SO_4$ and concentrated on rotary evaporator to yield a crude brown mass which was further purified by silica gel (60-120 mesh) column chromatography and eluted with 15% ethyl acetate in hexanes system to afford A16 as pale brown semi solid. Yield (0.05 g, 31% yield); $^1$H NMR (400 MHz, $CDCl_3$) δ ppm=8.48 (s, 1H), 7.40-7.37 (m, 2H), 7.20-7.16 (m, 2H), 3.62-3.60 (s, 2H), 3.12-3.06 (m, 2H), 2.54 (s, 3H), 1.06-1.04 (d, 12H); low resolution mass spectrum (ES+) m/z 317.9 ([M+H]$^+$]; calcd for $C_{18}H_{24}FN_3O$+H, 318.2].

1-[1-(4-Fluoro-phenyl)-5-methyl-1H-pyrazol-4-yl]-2-pyrrolidin-1-yl-ethanone (A17)

Following the procedure used to prepare A16, compound A17 was isolated as a brown solid. Yield: (0.05 g, 20.83%); $^1$H NMR (400 MHz, $CDCl_3$) δ ppm=8.11 (s, 1H), 7.40-7.35 (m, 2H), 7.22-7.17 (m, 2H), 3.83 (s, 2H), 2.76 (m, 4H), 2.55 (s, 3H), 1.87 (m, 4H); low resolution mass spectrum (ES+) m/z 288.1 ([M+H]$^+$]; calcd for $C_{16}H_{18}FN_3O$+H, 288.1].

Example 10

Synthesis of 1-[1-(4-Chloro-phenyl)-3,5-dimethyl-1H-pyrazol-4-yl]-2-piperidin-1-yl-ethanone (A18), 1-[1-(4-Chloro-phenyl)-3,5-dimethyl-1H-pyrazol-4-yl]-2-Pyrrolidine-1-yl-ethanone (A19) and 1-[1-(4-Chloro-phenyl)-3,5-dimethyl-1H-pyrazol-4-yl]-2-(Cyclopropyl-methyl-amino)-ethanone (A20)

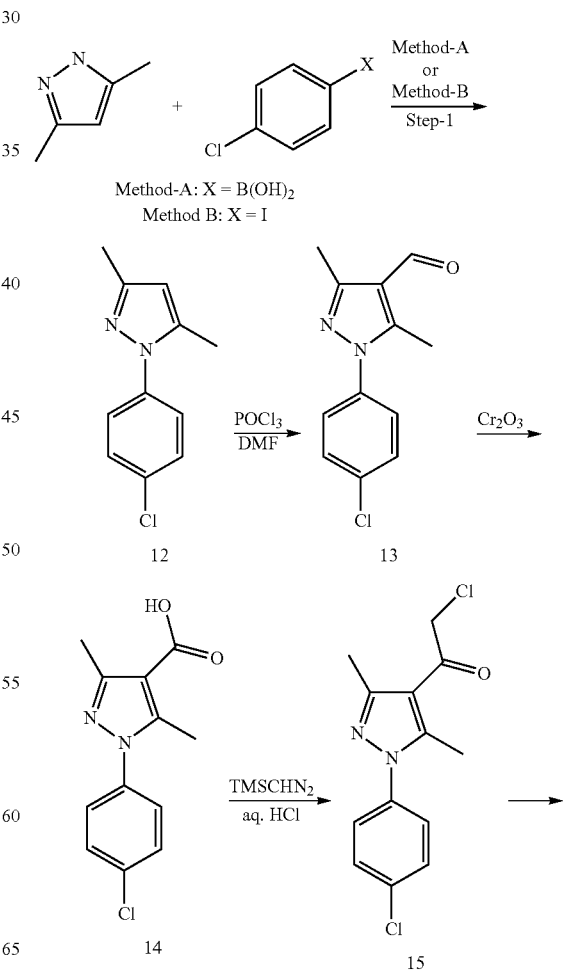

Method-A: X = B(OH)$_2$
Method B: X = I

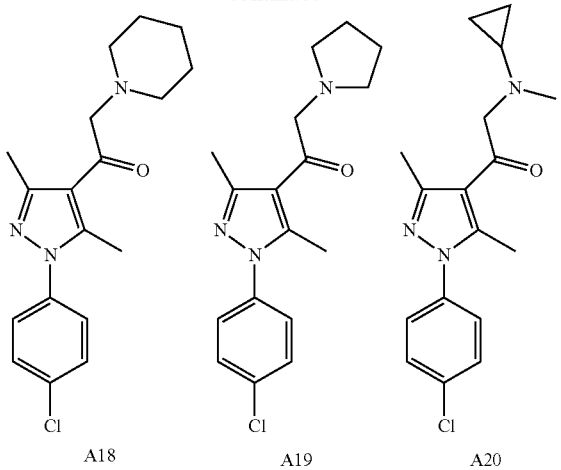

A18  A19  A20

1-[1-(4-Chloro-phenyl)-3,5-dimethyl-1H-pyrazol-4-yl]-2-piperidin-1-yl-ethanone (A18)

Step 1: Method A: Copper (II) acetate (4.7 g, 26.0 mmol) was well dried under vacuum and then suspended in anhydrous DCM (20 mL) in a 250 mL sealed tube. To this stirring solution di-isopropyl amine (3.6 mL, 26.0 mmol) was added slowly followed by 3,5-dimethylpyrazole (1 g, 10.4 mmol) and 4-chloro phenyl boronic acid (3 g, 19.2 mmol) respectively. The reaction was stirred at 55° C. for 18 h. Progress of the reaction was monitored by TLC. Upon completion of the reaction the mixture was filtered through celite bed and residue was washed with DCM (3×20 mL). The organic layer was concentrated and crude material thus obtained was purified by silica gel (100-200 mesh) column chromatography using 5% ethyl acetate in hexanes as eluting system to get compound I-(4-chloro-phenyl)-3,5-dimethyl-1H-pyrazole 12 as yellow oil (0.4 g, 1.9 mmol, 18% yield). Method B: A mixture of CuI (0.4 g, 2.3 mmol) and powdered anhydrous $Cs_2CO_3$ (5.2 g, 16.8 mmol) was dried well in 100 mL rbf under high vacuum for 30 minutes and then suspended in anhydrous DMF (14 mL). To this stirring solution were added 4-chloro iodobenzene (2 g, 11.6 mmol) and 3,5-dimethylpyrazole (0.56 g, 5.8 mmol) successively under inert atmosphere at room temperature. The reaction mixture was then stirred and heated at 120° C. for 40 h. Reaction was judge complete by TLC. Reaction mixture upon cooling to room temperature was filtered through celite bed and residue was washed thoroughly with ethyl acetate (3×200 mL). The organic layer was washed with water (3×250 mL), then with brine (100 mL), dried over sodium sulphate and concentrated to dryness to give crude product which was chromatographed on silica gel (100-200 mesh) and eluted with 5% ethyl acetate in hexanes to afford the 12 as yellow oil (0.3 g, 1.4 mmol, 25% yield) $^1$H NMR (400 MHz, $CDCl_3$) δ ppm=7.41-7.39 (m, 2H), 7.37-7.35 (m, 2H), 5.98 (s, 1H), 2.28 (s, 3H), 2.27 (s, 3H); low resolution mass spectrum (ES+) m/z 206.9 ([M+H]$^+$); calcd for $C_{11}H_{11}ClN_2$+H, 207.1]. Step 2: To a stirred solution of anhydrous DMF (0.9 mL, 12.1 mmol), $POCl_3$ (1.1 mL, 12.1 mmol) was added at 0° C. slowly under inert atmosphere and stirring continued for 15 minutes. A solution of compound 12 (2.1 mmol) in 1 mL of anhydrous DMF was added drop wise at 0° C. After completion of addition, the reaction mixture was stirred at 70° C. for 18 h and progress was monitored by TLC. Upon completion of the reaction, the mixture was poured onto ~20 g crushed ice and pH was made basic using ~5 g sodium bicarbonate. The aqueous layer was then extracted with (3×20 mL) ethyl acetate. The organic layer washed with brine, dried over sodium sulphate, evaporated under vacuum to give 1-(4-chloro-phenyl)-3,5-dimethyl-1H-pyrazole-4-carbaldehyde (13): $^1$H NMR (400 MHz, $CDCl_3$) δ ppm=10.00 (s, 1H), 7.48-7.45 (m, 2H), 7.37-7.33 (m, 2H), 2.54 (s, 3H), 2.50 (s, 3H). Step 3: Compound 13 (0.3 g, 1.28 mmol) was dissolved in 10 mL of acetone and cooled to 0° C. To this solution 5 mL of Jones reagent (prepared by dissolving chromium trioxide 7 g in $H_2SO_4$:$H_2O$ (5.5 mL:25 mL)) was added at 0° C. After complete addition the mixture was warmed to ambient temperature and stirred for 4 h. Progress of the reaction was monitored by TLC. Upon completion of the reaction, the mixture was quenched with isopropanol (10 mL) and extracted with (3×20 mL) DCM. The organic phase was then dried over sodium sulphate, and concentrated on rotary evaporator to give crude acid derivative 1-(4-chloro-phenyl)-3,5-dimethyl-1H-pyrazole-4-carboxylic 14 as yellow solid (0.3 g, 1.2 mmol, 93% yield) which was used as such for the next reaction. $^1$H NMR (400 MHz, $CDCl_3$) δ ppm=12.43 (br, 1H), 7.61-7.58 (m, 2H), 7.56-7.53 (m, 2H), 2.46 (s, 3H), 2.35 (s, 3H). Step 4: To acid 14 (0.3 g, 1.2 mmol), 5 mL thionyl chloride was added slowly at room temperature and then resulting mixture was heated to reflux for 8 h. (Progress of the reaction was monitored by TLC by forming the corresponding methyl ester). Upon completion of reaction, mixture was stripped off under vacuum, traces of $SOCl_2$ were removed by co-evaporating the residue with 5 mL of anhydrous toluene. The residue obtained was dried well and then dissolved in 10 mL of anhydrous acetonitrile. Reaction mixture was cooled to 0° C. and to this stirring solution was added 2M solution of (0.4 mL, 2.4 mmol) $TMSCHN_2$ drop wise, resulting solution was warmed to ambient temperature and stirred for about 18 h under nitrogen atmosphere. Then reaction mixture was cooled again to 0° C. and to it was added 2 mL of conc. HCl. After continuing the reaction for 2 h at ambient temperature, it was cooled again to 0° C. and basified with 1M NaOH, The aqueous phase was then extracted with (3×20 mL) ethyl acetate. The organic layer was then evaporated and crude material thus obtained was purified by column chromatography (100-200 mesh silica gel) and pure fractions were eluted with 5% ethyl acetate:hexane system. Concentration on a rotary evaporator afforded chloro-1-[1-(4-chloro-phenyl)-3,5-dimethyl-1H-pyrazol-4-yl]-ethanone 15 as white solid (0.12 g, 0.42 mmol, 35% yield). $^1$H NMR (400 MHz, $CDCl_3$) δ ppm=7.48-7.45 (m, 2H), 7.34-7.25 (m, 2H), 4.48 (s, 2H), 2.54 (d, 6H); low resolution mass spectrum (ES+) m/z 282.9 ([M+H]$^+$); calcd for $C_{13}H_{12}Cl_2N_2O$+H, 283.0]. Step 5: A mixture of compound 15 (0.5 g, 1.45 mmol) and piperidine 2 mL was stirred at ambient temperature for 1 h and monitored by TLC. Upon completion of reaction, it was diluted with 100 mL ethyl acetate. The organic layer was washed with water (7×100 mL), then dried and removed at 10° C. under vacuum. The crude material was then purified by silica gel (100-200 mesh) using 4% methanol in dichloromethane as eluting system. Fractions containing pure compound were pooled out and evaporated at 10° C. in vacuo to afford the title compound A18 as an off white solid (0.1 g, 0.30 mmol, 20% yield). $^1$H NMR (400 MHz, acetone) δ ppm=7.60-7.53 (m, 4H), 3.40 (s, 2H), 2.56 (s, 3H), 2.56 (s, 3H), 2.47 (s, 3H), 2.43 (m, 4H), 1.55-1.50 (m, 4H), 1.44-

1.41 (m, 2H); low resolution mass spectrum (ES+) m/z 331.9 ([M+H]⁺); calcd for $C_{18}H_{22}ClN_3O+H$, 332.1].

1-[1-(4-Chloro-phenyl)-3,5-dimethyl-1H-pyrazol-4-yl]-2-Pyrrolidine-1-yl-ethanone (A19)

Following the procedure used for the preparation of A18 compound A19 was isolated in 15% yield (0.1 g). ¹H NMR (400 MHz, acetone) δ ppm=7.61-7.57 (m, 4H), 7.56-7.52 (m, 2H), 3.61 (s, 2H), 2.60-2.54 (m, 7H), 2.47 (s, 3H), 1.77-1.70 (m, 4H); low resolution mass spectrum (ES+) m/z 318.0 ([M+H]⁺); calcd for $C_{17}H_{20}ClN_3O+H$, 318.1].

1-[1-(4-Chloro-phenyl)-3,5-dimethyl-1H-pyrazol-4-yl]-2-(Cyclopropyl-methyl-amino)-ethanone (A20)

Following the procedure used for the preparation of A18 compound A20 was isolated in 95 yield (0.05 g, 0.15 mmol). ¹H NMR (400 MHz, CDCl₃) δ ppm=7.47-7.43 (m, 2H), 7.34-7.30 (m, 2H), 3.76 (s, 2H), 2.52 (m, 6H), 2.50 (s, 3H), 2.06-2.01 (m, 1H), 0.49-0.41 (m, 4H); low resolution mass spectrum (ES+) m/z 318.0 ([M+H]⁺); calcd for $C_{17}H_{20}ClN_3O+H$, 318.1].

Example 11

Synthesis 1-(1-(4-chlorophenyl)-3,5-dimethyl-1H-pyrazol-4-yl)-2-cyclohexylethanone (A21)

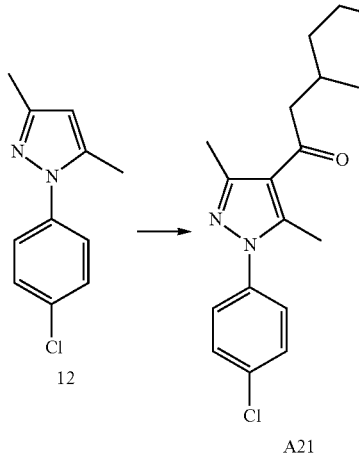

1-(1-(4-chlorophenyl)-3,5-dimethyl-1H-pyrazol-4-yl)-2-cyclohexylethanone (A21)

Compound A21 was prepared from pyrazole 12 according to the procedure used to prepare A2: ¹H NMR (400 MHz, CDCl₃) δ ppm 7.56 (m, 2H), 7.45 (m, 2H), 2.70 (d, J=6.8 Hz, 2H), 2.47 (s, 6H), 1.92 (m, 1H), 1.78-1.66 (m, 5H), 1.37-1.18 (m, 3H), 1.09-0.99 (m, 2H); low resolution mass spectrum (ES+) m/z 331.1 ([M+H]⁺); calcd for $C_{19}H_{23}ClN_2O+H$, 330.2].

Example 12

Synthesis of 1-[1-(4-Chloro-phenyl)-1H-pyrazol-4-yl]-2-piperidin-1-yl-ethanone (A22), 1-[1-(4-Chloro-phenyl)-1H-pyrazol-4-yl]-2-pyrrolidin-1-yl-ethanone (A23), and 1-[1-(4-Chloro-phenyl)-1H-pyrazol-4-yl]-2-(cyclopropyl-methyl-amino)-Ethanone (A24)

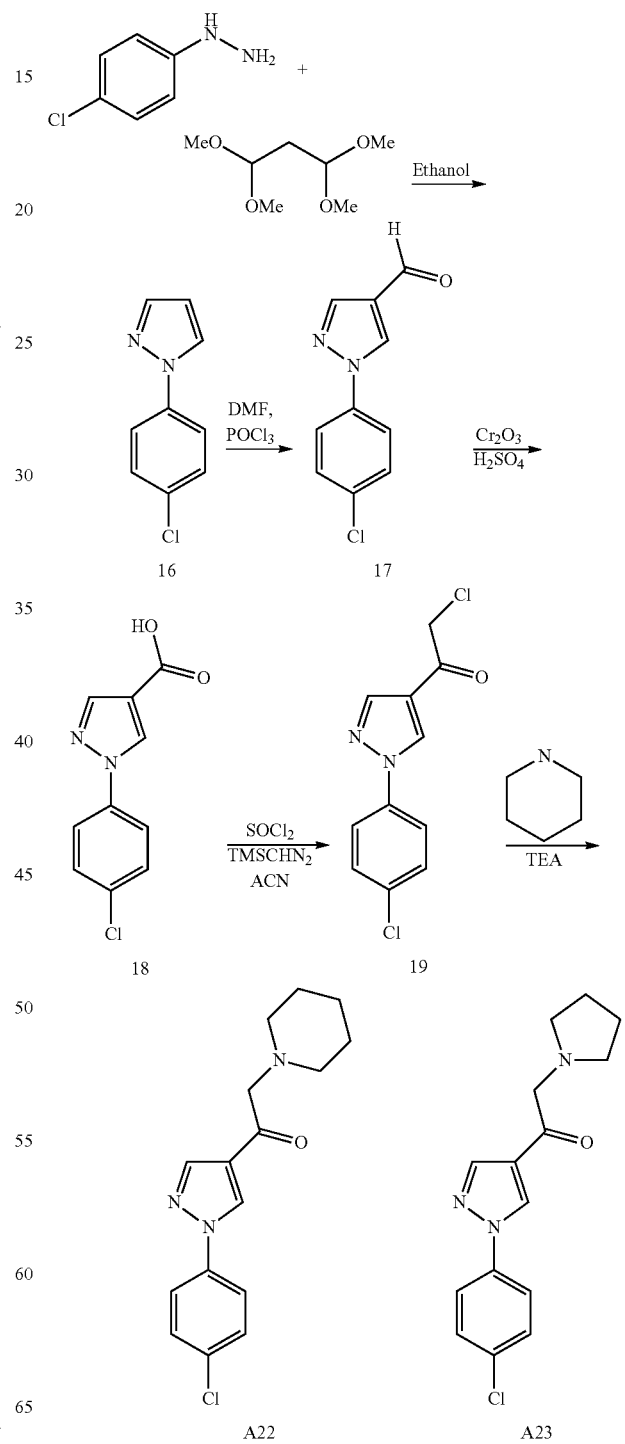

-continued

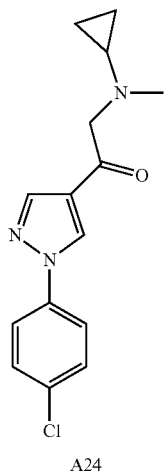

A24

1-[1-(4-Chloro-phenyl)-1H-pyrazol-4-yl]-2-piperidin-1-yl-ethanone (A22)

Step 1: 1,1,3,3-Tetramethoxy propane (9.15 g, 55.8 mmol) was added to a suspension of 4-Chlorophenyl hydrazine hydrochloride (10 g, 55.8 mmol) in absolute ethanol (120 mL) and the resulting mixture was heated to reflux for 1 h. Progress of the reaction was monitored by TLC. After completion of the reaction, the reaction mixture was cooled and neutralized with 10% sodium bicarbonate solution and extracted with DCM (3×300 mL). The organic layer washed with brine solution (300 mL), dried over sodium sulphate and concentrated under vacuum to get crude 1-(4-chlorophenyl)-1H-pyrazole 16 as yellow colored solid (9.7 g, 97%); $^1$H NMR (400 MHz, CDCl$_3$): δ ppm=7.88-7.87 (d, 1H), 7.71 (m, 1H), 7.64-7.61 (m, 2H), 7.42-7.39 (m, 2H), 6.47-6.46 (m, 1H); low resolution mass spectrum (ES+) m/z 178.9 ([M+H]$^+$); calcd for C$_9$H$_7$ClN$_2$+H, 179.0]. Step 2: Phosphorus oxychloride (41.17 g, 0.272 mol) was added slowly to anhydrous DMF (19.91 g, 0.272 mol) at −10° C. under inert atmosphere. After stirring the mixture for 15 minutes, a solution of compound 16 (9.7 g, 0.054 mol) in 20 mL of anhydrous DMF was added to reaction mixture slowly and then reaction was first warmed to room temperature and then heated at 70° C. for 12 h. The reaction monitored by TLC. After completion of the reaction, the reaction mixture was cooled to room temperature and neutralized with 10% sodium bicarbonate solution and extracted with ethyl acetate (3×300 mL). The organic layer was washed with water (2×300 mL) and then with brine (100 mL). The organic layer was then dried over sodium sulphate and concentrated on rotary evaporator to give 1-(4-chlorophenyl)-1H-pyrazole-4-carbaldehyde 17 as brown colored solid. (8.0 g, 71%); low resolution mass spectrum (ES+) m/z 206.9 ([M+H]$^+$); calcd for C$_{10}$H$_7$ClN$_2$O+H, 207.0]. Step 3: A stirring solution of compound 17 (8.0 g, 38.8 mmol) in acetone (100 mL) was cooled to 0° C. Jones reagent (50 mL) was added drop wise to this reaction mixture and mixture was stirred for 1 h at room temperature. After completion of the reaction (monitored by TLC), excess Jones reagent was quenched with the addition of isopropanol. Solid formed in the reaction was filtered off and filtrate was extracted with diethyl ether (2×400 mL). The organic layer was then separated, dried over sodium sulphate and concentrated in vacuo to give crude mass which was purified by giving washings of 10% ethyl acetate in hexanes (100 mL) to afford 1-(4-chloro-phenyl)-1H-pyrazole-4-carboxylic acid 18 as an off white solid (6.0 g, 27 mmol, 70% yield). $^1$H NMR (400 MHz, DMSO): δ=12.69 (br, 1H), 9.06 (s, 1H), 8.10 (s, 1H), 7.97-7.94 (d, 2H), 7.60-7.57 (d, 2H); low resolution mass spectrum (ES+) m/z 222.9 ([M+H]$^+$); calcd for C$_{10}$H$_7$ClN$_2$O$_2$+H, 223.0]. Step 4: Thionyl chloride (40 mL) was added to the compound 18 (4.0 g, 18.0 mmol) at room temperature under inert atmosphere. The mixture was stirred for 15 minutes at the same temperature and then heated to reflux for 4 h. The reaction was monitored by TLC. Excess thionyl chloride was removed under vacuum and traces were removed by co-evaporation of the residue with toluene under vacuum under nitrogen atmosphere. Crude acid chloride was then dissolved in anhydrous acetonitrile and cooled to 0° C. under inert atmosphere. To this stirring solution was added slowly ice cold (2M) solution of TMS diazomethane (13.48 mL, 27.0 mmol) in ether. The reaction mixture was allowed to come to room temperature and stirred for 18 h. The reaction mixture was then cooled again to 0° C. and HCl (6.0 M, 10 mL) was added to the reaction mixture and stirring was continued for additional 2 h. The reaction mixture was then neutralized with 1.0M NaOH solution and extracted with ethyl acetate (3×100 mL). The organic layer washed once with brine solution (70 mL), dried over sodium sulphate and concentrated under vacuum to get crude material which was purified by chromatography on (100-200 mesh) silica gel and eluted with 10% ethyl acetate in hexanes solvent system to afford 2-chloro-1-[1-(4-chlorophenyl)-1H-pyrazol-4-yl]-ethanone 19 as yellow colored solid (2.0 g, 7.9 mmol, 43% yield). $^1$H NMR (400 MHz, CDCl$_3$): δ ppm=8.47 (s, 1H), 8.15 (s, 1H), 7.68-7.64 (m, 2H), 7.48-7.45 (m, 2H), 4.45 (s, 2H); low resolution mass spectrum (ES+) m/z 253.0 ([M−H]$^-$); calcd for C$_{11}$H$_8$Cl$_2$N$_2$O—H, 253]. Step 5: To a stirred solution of compound 19 (0.1 g, 0.3 mmol) in acetonitrile (10 mL) was added triethylamine (0.08 g, 0.78 mmol) at room temperature followed by piperidine (0.05 g, 0.6 mmol) under inert atmosphere. The reaction mixture was then heated to reflux for 1 h and monitored by TLC. After completion of the reaction, reaction mixture was concentrated under the vacuum and residual material was dissolved in DCM (30 mL). The organic layer was then washed with water (2×30 mL)) followed by brine (15 mL). The organic layer was concentrated to dryness and crude mass was chromatographed on silica gel (100-200 mesh) (2% methanol in DCM). The desired title compound A22 was isolated as an off white solid (80 mg, 0.26 mmol, 67% yield). $^1$H NMR (400 MHz, CDCl$_3$): δ ppm=8.69 (s, 1H), 8.2 (s, 1H), 7.66-7.64 (d, 2H), 7.46-7.44 (d, 2H), 3.48 (s, 2H), 2.49 (m, 4H), 1.65-1.60 (m, 4H), 1.47-1.46 (m, 2H); low resolution mass spectrum (ES+) m/z 304.0 ([M+H]$^+$); calcd for C$_{16}$H$_{18}$ClN$_3$O+H, 304.1].

1-[1-(4-Chloro-phenyl)-1H-pyrazol-4-yl]-2-pyrrolidin-1-yl-ethanone (A23)

Following the procedure used for A22 compound A23 was isolated as an off white solid (0.22 g, 0.76 mmol, 39% yield). $^1$H NMR (400 MHz, CDCl$_3$): δ ppm=8.55 (s, 1H), 8.20 (s, 1H), 7.66-7.62 (m, 2H), 7.46-7.43 (m, 2H), 3.71 (s, 2H), 2.66-2.63 (m, 4H), 1.86-1.81 (m, 4H); low resolution mass spectrum (ES+) m/z 290.0 ([M+H]$^+$); calcd for C$_{15}$H$_{16}$ClN$_3$O+H, 290.1].

1-[1-(4-Chloro-phenyl)-1H-pyrazol-4-yl]-2-(cyclopropyl-methyl-amino)-ethanone (A24)

Following the procedure used for A22 compound A24 was isolated as an off white solid Yield: (60 mg, 35%); $^1$H NMR (400 MHz, CDCl$_3$): δ ppm=8.48 (s, 1H), 8.18 (s, 1H), 7.65-7.61 (m, 2H), 7.46-7.43 (m, 2H), 3.72 (s, 2H), 2.43 (s, 3H), 1.95-1.90 (m, 1H), 0.52-0.50 (m, 4H); low resolution mass spectrum (ES+) m/z 290.0 ([M+H]$^+$; calcd for C$_{15}$H$_{16}$ClN$_3$O+H, 290.1].

Example 13

Synthesis of 1-[2-(4-Chloro-phenyl)-5-methyl-oxazol-4-yl]-2-piperidin-1-yl-ethanone (A25)

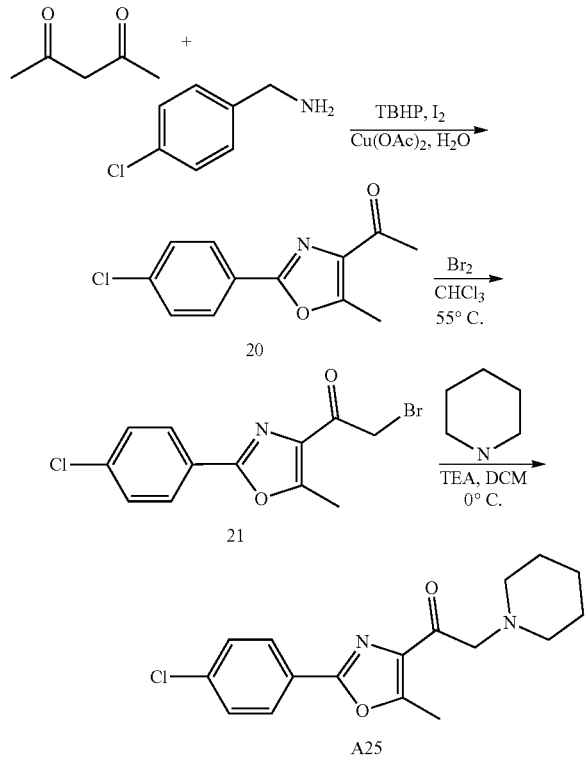

1-[2-(4-Chloro-phenyl)-5-methyl-oxazol-4-yl]-2-piperidin-1-yl-ethanone (A25)

Step 1: To a stirred solution of 4-chlorobenzylamine (12.73 g, 89.8 mmol) in DMF (50 mL) was successively added iodine (15.20 g, 59.9 mmol), followed by acetyl acetone (6.0 g, 59.9 mmol), Cu(OAc)$_2$.H$_2$O (1.19 g, 5.9 mmol), and tert-butyl hydrogen peroxide 70% in water (10.8 g, 119.8 mmol). After addition, the reaction mixture was stirred for 4 h at room temperature. Reaction progress was monitored by TLC. After completion; the reaction mixture was quenched with ice water (200 mL) and extracted with EtOAc (200 mL×3). The organic layer washed with water (200 mL) and followed by brine solution (200 mL), dried over sodium sulphate and concentrated under vacuum to get crude material which was purified on (100-200 mesh) silica gel. Pure compound was eluted in 2% ethyl acetate in hexanes solvent system yielded 1-[2-(4-chloro-phenyl)-5-methyl-oxazol-4-yl]-ethanone 20 as pale yellow solid. Yield=(2.5 g, 17.71%); $^1$H NMR (400 MHz, CDCl$_3$): δ ppm=7.96-7.94 (m, 2H), 7.44-7.42 (m, 2H), 2.68 (s, 3H), 2.57 (s, 3H); low resolution mass spectrum (ES+) m/z 236.1 ([M+H]$^+$); calcd for C$_{12}$H$_{10}$ClNO$_2$+H, 235.0]. Step 2: A solution of bromine (1.94 g, 12.1 mmol) in chloroform (10 mL) was added drop wise to a mixture of compound 20 (2.6 g, 11.0 mmol) in chloroform (30 mL) at 50° C. After complete addition, the reaction mixture was stirred for 30 min at 55° C. After completion; the reaction mixture was poured into saturated sodium bicarbonate solution (150 mL) and extracted with chloroform (200 mL×2). The organic layer washed with water (100 mL), and followed by brine solution (100 mL), dried over sodium sulphate and concentrated under vacuum to get crude material which was purified on (100-200 mesh) silica gel. Pure compound was eluted in 1-2% ethyl acetate in hexanes solvent system to afford 2-bromo-1-[2-(4-chloro-phenyl)-5-methyl-oxazol-4-yl]-ethanone 21 as pale yellow colored solid. Yield=(1.5 g, 44.9%); $^1$H NMR (400 MHz, CDCl$_3$): δ ppm=7.97-7.93 (m, 2H), 7.46-7.42 (m, 2H) 4.56 (s, 2H), 2.71 (s, 3H); low resolution mass spectrum (ES+) m/z 315.9 ([M+H]$^+$); calcd for C$_{12}$H$_9$Br$^{81}$Cl$^{35}$NO$_2$+H, 316]. Step 3: A stirred solution of compound 21 (0.3 g, 0.95 mmol) in DCM (10 mL) was cooled to 0° C. and triethylamine (0.193 g, 1.9 mmol) was drop-wise added to reaction mixture followed by piperidine (0.162 g, 1.9 mmol). After complete addition, the reaction mixture was stirred under inert atmosphere for 15 min at 0° C. The reaction monitored by TLC. After completion; the reaction mixture was diluted with DCM and washed with water (25 mL×4) and followed by brine (30 mL) and dried over sodium sulphate. The organic layer was concentrated to dryness and the crude material was purified on silica gel (100-200 mesh) column chromatography (2% MeOH in CH$_2$Cl$_2$) The desired title compound A25 was isolated as a pale yellow solid. Yield=(0.1 g, 33.0%); $^1$H NMR (400 MHz, DMSO): δ=7.96-7.93 (m, 2H), 7.44-7.42 (m, 2H), 3.86 (s, 2H), 2.68 (s, 3H), 2.57-2.54 (m, 4H), 1.68-1.63 (m, 4H), 1.48-1.45 (m, 2H) low resolution mass spectrum (ES+) m/z 319.0 ([M+H]$^+$); calcd for C$_{17}$H$_{19}$BrClN$_2$O$_2$+H, 319.1].

Example 14

Synthesis of 2-Chloro-1-[3-(4-chloro-phenyl)-isothiazol-5-yl]-ethanone (A26)

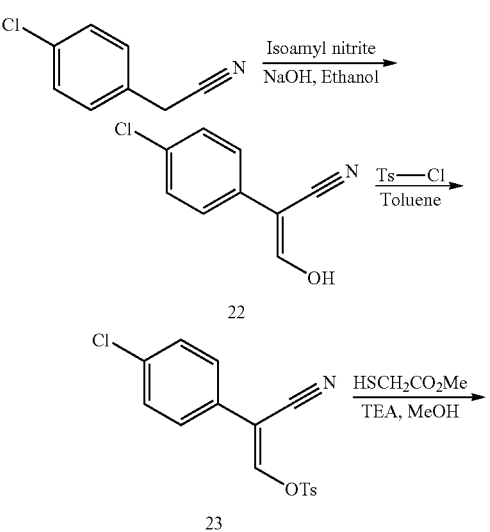

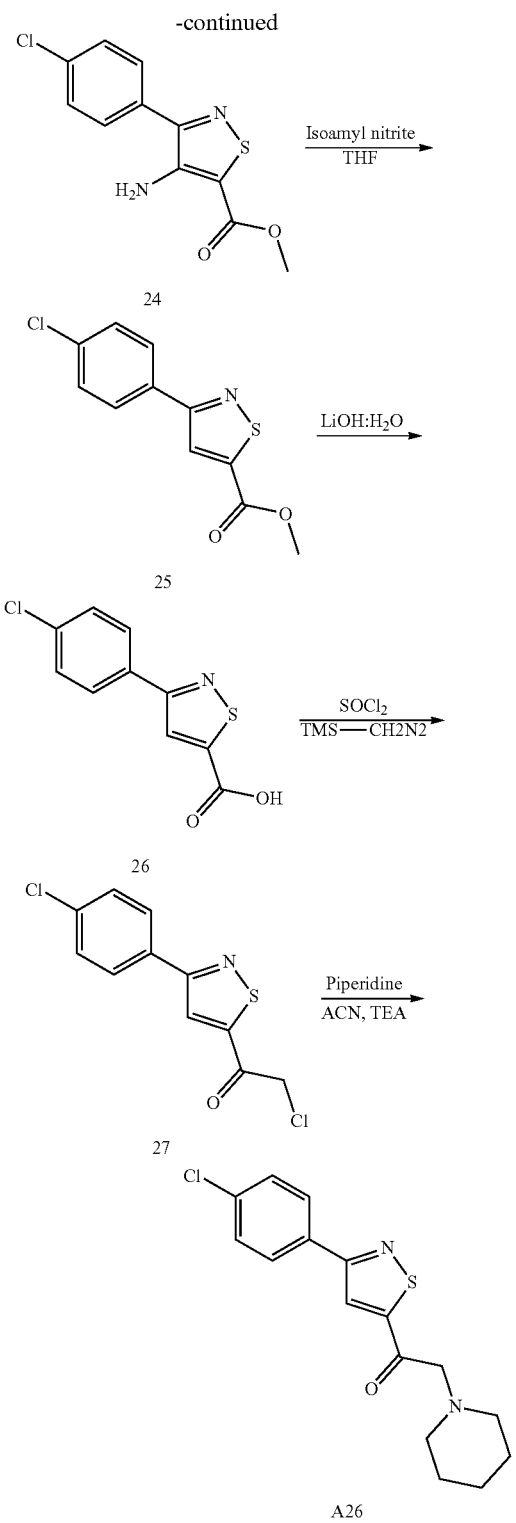

2-Chloro-1-[3-(4-chloro-phenyl)-isothiazol-5-yl]-ethanone (A26)

Step 1: Isoamyl nitrile (9.2 g, 0.07915 mol) was dissolved in 30 mL ethanol and was then added to stirring solution of p-Chloro phenyl acetonitrile (10 g, 0.06596 mol) and NaOH (2.6 g, 0.06596 mol) in 50 mL ethanol under nitrogen atmosphere at 0° C. The temperature was maintained at 10-20° C. throughout the addition. After complete addition, the reaction was warmed to RT and stirred for 3 h. After completion; the reaction was diluted with ether (300 mL). A solid formed and the solid was removed via filtration. The filtrate was concentrated and the solid was washed with Et$_2$O. The solid was dried well to yield 2-(4-chloro-phenyl)-3-hydroxy-acrylonitrile 22 as an off-white solid. Yield—(10 g, 84.24%); $^1$H-NMR: (400 MHz, DMSO D6); δ=8.25-8.22 (m, 1H), 7.57-7.53 (m, 2H), 7.30-7.26 (m, 3H). Step 2: Compound 22 (10 g, 0.055 mol) and pTs-Cl (10.55 g, 0.055 mol) were refluxed in 125 mL of toluene for 1 h. After completion; the reaction was cooled to RT and quenched with 100 g of ice and extracted with ethyl acetate (200 mL×3) The organic layer was dried and evaporated under reduced pressure to afford toluene-4-sulfonic acid-2-(4-chloro-phenyl)-2-cyano-vinyl 23 as yellow solid. Yield— (12 g, 65.32%); $^1$H-NMR: (400 MHz, CDCl$_3$); δ=7.94-7.91 (m, 2H), 7.74-7.71 (m, 2H), 7.45-7.42 (m, 2H), 7.40-7.38 (m, 2H), 2.45 (s, 3H). Step 3: To a stirring mixture of compound 23 (11 g, 0.056 mol) and methyl thioglocolate (6.12 g, 0.0680 mol); TEA (16.96 mL, 0.1134 mol) was added drop wise at 10° C. so that temperature not rise more than 45° C. The reaction was stirred for 3 h. Reaction progress was monitored by TLC. After completion; the reaction was quenched by 100 g ice. A solid formed and the solid was filtered and washed with water. The solid was dissolved in DCM, dried over Na$_2$SO$_4$ and evaporated under reduced pressure to yield 4-amino-3-(4-chloro-phenyl)-iso-thiazole-5-carboxylic acid methyl ester 24 as an off-white solid, which was use as such for next step without any purification. Yield—(4.8 g, 32%); $^1$H-NMR: (400 MHz, CDCl$_3$); δ=7.68-7.65 (m, 2H), 7.48-7.45 (m, 2H), 5.36 (br s, 2H), 3.90 (s, 3H); low resolution mass spectrum (ES+) m/z 268.9 ([M+H]$^+$); calcd for C$_{11}$H$_9$ClN$_2$O$_2$S+H, 269.0]. Step 4: To a stirring mixture of compound 24 (8 g, 0.0298 mol) in 80 mL of THF, isoamyl nitrite (8.73 g, 0.07462 mol) was added and reaction was refluxed for 1.5 h. Reaction progress was monitored by TLC. After completion; the solvent was removed under reduced pressure. The resulting solid was washed twice with 200 mL hexane to yield 3-(4-chloro-phenyl)-isothiazole-5-carboxylic acid methyl ester 25 as pale yellow solid was used for next step without any purification. Yield (4 g, 53%); $^1$H-NMR: (400 MHz, CDCl$_3$); δ=8.08 (s, 1H), 7.90-7.87 (m, 2H), 7.44-7.42 (m, 2H), 3.95 (s, 3H); low resolution mass spectrum (ES+) m/z 254.3 ([M+H]$^+$); calcd for C$_{11}$H$_8$ClNO$_2$S+H, 254.0]. Step 5: To a cooled (0° C.) solution of compound 25 (4 g, 0.0158 mol) in 40 mL of THF, 2M LiOH solution was added drop wise. The reaction was further stirred for 18 h. Progress was monitored by TLC. After completion; the reaction was acidified with 10% HCl until pH 9. The reaction mixture was extracted with ethyl acetate (200 mL×3). The organic layer was dried over Na$_2$SO$_4$ and evaporated under reduced pressure. The resulting solid was filtered through 100-200 silica gel and washed with ethyl acetate. The filtrate was evaporated to yield compound 26 as pale yellow solid. Yield (3.7 g, quant); $^1$H-NMR: (400 MHz, CDCl$_3$); δ=7.92 (s, 1H), 7.78-7.76 (d, 2H), 7.31-7.29 (d, 2H); low resolution mass spectrum (ES+) m/z 237.7 ([M−H]$^−$); calcd for C$_{10}$H$_6$ClNO$_2$S—H, 238.0]. Step 6: To compound 26 (3.7 g, 0.01548 mol) thionyl chloride (30 mL) was added and reaction was refluxed for 1.4 h. Reaction progress was monitored by TLC. After completion; excess thionyl chloride removed under reduced pressure under inert atmosphere. The acid chloride was dissolved in 30 mL of dry ACN and cooled to 0° C. TMS diazomethane (2M in diethyl ether, 10 mL) was added drop-wise. The reaction was stirred for 2 h. Reaction progress was monitored by TLC. After completion; the reaction was quenched by concentrated HCl (5 mL). The reaction was stirred further for 1 h. TLC showed complete deprotection of TMS group. The reaction was diluted with 50 mL water and extracted with ethyl acetate (100 mL×3). The combined organic layers were dried over $Na_2SO_4$ and evaporated. The compound was purified on 100-200 silica gel pure compound was eluted in 5% ethyl acetate in hexane yielded 2-chloro-1-[3-(4-chloro-phenyl)-isothiazol-5-yl]-ethanone 27 as pale yellow solid. Yield (2.5 g, 60.97%); $^1$H-NMR: (400 MHz, $CDCl_3$); δ=8.04 (s, 1H), 7.90-7.88 (d, 2H), 7.46-7.44 (d, 2H), 4.59 (s, 1H). Step 7: To a stirring mixture of Compound 27 (0.5 g, 0.001814 mol) in 10 mL of AcN were added piperidine (0.21 mL, 0.002214 mol) and TEA (0.512 mL, 0.00368 mol). The reaction was stirred for 2 h. Reaction progress was monitored by TLC. After completion; AcCN was removed under reduced pressure and the crude material was purified twice on 100-200 silica gel using DCM and hexane as eluting system. Pure compound was eluted in 5% DCM-hexane, yielded A26 as pale yellow solid. Yield—0.045 gm, (7.75%); $^1$H-NMR: (400 MHz, $CDCl_3$); δ=8.17 (s, 1H), 7.92-7.88 (d, 2H), 7.44-7.40 (d, 2H), 3.37 (s, 2H), 2.58-2.56 (m, 4H), 1.77-1.71 (m, 4H), 1.51-1.48 (m, 2H); low resolution mass spectrum (ES+) m/z 321.1 ([M+H]$^+$]; calcd for $C_{16}H_{17}ClN_2OS+H$, 321.1].

Example 15

Synthesis of 1-(5-(4-chlorophenyl)-2-methylthiophen-3-yl)-2-(piperidin-1-yl)ethanone (A27), 1-(5-(4-chlorophenyl)-2-methylthiophen-3-yl)-2-(4-fluoropiperidin-1-yl)ethanone (A28) and 1-(5-(4-chlorophenyl)-2-methylthiophen-3-yl)-2-(4-hydroxypiperidin-1-yl)ethanone (A29)

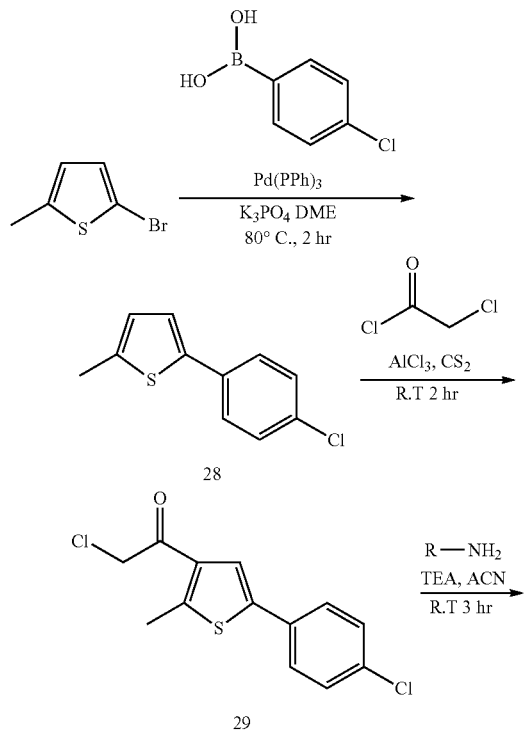

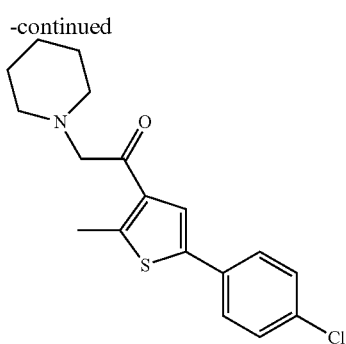

A27

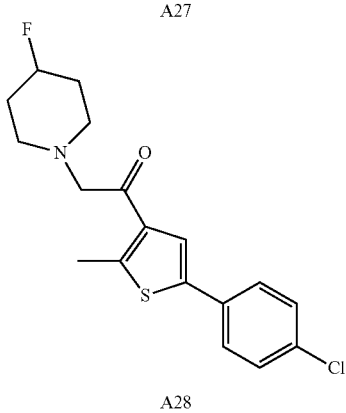

A28

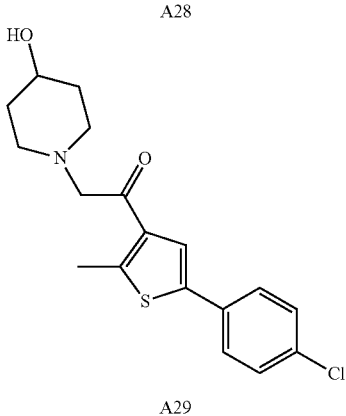

A29

1-(5-(4-chlorophenyl)-2-methylthiophen-3-yl)-2-(piperidin-1-yl)ethanone (A27)

Step 1: A mixture of 2-bromo-5-methylthiophene (4 g, 22.5 mmol) and Pd(PPh$_3$)$_4$ (1.30 g, 1.12 mmol) was taken in DME (30 mL) and degassed with N$_2$ for 15-20 min. K$_3$PO$_4$ (11.98 g, 56.4 mmol, 1.5 M solution in H$_2$O) was added and the mixture was degassed for additional 10-15 min. followed by addition of 4-chlorophenylboronic acid (3.88 g, 24.8 mmol). The reaction mixture was then heated to 80° C. for 2 hr and the progress was monitored by TLC. After completion of reaction, the solution was filtered through a bed of celite. The filtrate was diluted with water (100 mL) and extracted with ethyl acetate (100 mL×3). The organic layer was concentrated to get crude compound. The material was purified by column chromatography (100-200) mesh silica with 100% hexane as eluent, to obtain 2-(4-chloro-phenyl-5-methyl-thiophene (28) as a white solid. Yield—2.7 gm (58%); $^1$H NMR (400 MHz, CDCl$_3$) δ ppm=7.47-7.45 (d, 2H), 7.31-7.25 (d, 2H), 7.07-7.06 (d, 1H), 6.72-6.71 (d, 1H), 2.4 (S, 3H). Step 2: To AlCl$_3$ (4.8 g, 36 mmol) in a dry 50 mL RB flask CS$_2$ (20 ml) was added, followed by addition of chloroacetylchloride (3.36 g, 30 mmol). The reaction stirred at RT for 15 min before addition of 28 (2.5 g, 12 mmol). The reaction was allowed to stir at RT for 2 hr and the reaction progress was monitored by TLC. (Note: reaction doesn't show completion). After 3 hr the reaction was diluted with water (100 mL), extracted with ethyl acetate (50 mL×3). The organic layer was combined and was washed with brine, dried over sodium sulphate and concentrated to get the crude compound. This material was purified by column chromatography (230-400) mesh silica and 1% ethyl acetate:hexane as eluent to obtain pure 2-chloro-1-(5-(4-chlorophenyl)-2-methylthiophen-3-yl)ethanone 29 as a white solid. Yield—0.53 gm (15%); $^1$H NMR (400 MHz, CDCl$_3$) δ ppm=7.46-7.45 (d, 2H), 2.4 (S, 3H), 4.54 (s, 2H), 2.7 (S, 3H). Step 3: Acetonitrile (5 mL), piperidine (1.37 mmol) and triethylamine (0.213 g, 2.11 mmol) were placed in a flask and allowed to stir at RT for 10 min. This was followed by addition of compound 29 (0.3 g, 1 mmol). The reaction was allowed to stir at RT for 3 hr and reaction progress was monitored by TLC. After completion of the reaction it was diluted with water (50 mL) and extracted with ethyl acetate (30 mL×3). The organic layer was combined, washed with brine and dried over sodium sulphate. Concentration gave a crude compound that was purified by column chromatography (230-400) mesh silica and 1% MeOH: DCM as eluent. The title compound A27 was isolated as an off white solid. $^1$H-NMR: (400 MHz, CDCl$_3$); δ 7.63 (s, 1H), 7.46 (m, 2H), 7.34 (m, 2H), 3.61 (s, 2H), 2.74 (s, 3H), 2.52 (m, 4H), 1.63 (m, 2H), 1.46 (m, 2H); low resolution mass spectrum (ES+) m/z 333.9 ([M+H]$^+$); calcd for C$_{18}$H$_{20}$ClNOS+H, 334.1].

1-(5-(4-chlorophenyl)-2-methylthiophen-3-yl)-2-(4-fluoropiperidin-1-yl)ethanone (A28)

Following the procedure used for A27 compound A28 was isolated as an off white solid. $^1$H-NMR: (400 MHz, CDCl$_3$); 7.56 (s, 1H), 7.46 (m, 2H), 7.35 (m, 2H), 4.72 (m, 1H), 2.75 (s, 2H), 2.70 (m, 2H), 2.59 (m, 2H), 1.96 (m, 4H); low resolution mass spectrum (ES+) m/z 351.9 ([M+H]$^+$); calcd for C$_{18}$H$_{19}$ClFNOS+H, 352.1].

1-(5-(4-chlorophenyl)-2-methylthiophen-3-yl)-2-(4-hydroxypiperidin-1-yl)ethanone (A29)

Following the procedure used for A27 compound A29 was isolated as an off white solid. $^1$H-NMR: (400 MHz, CDCl$_3$); 7.59 (s, 1H), 7.46 (m, 2H), 7.35 (m, 2H), 3.75 (m, 1H), 3.66 (s, 2H), 2.87 (m, 2H), 2.75 (s, 3H), 2.35 (m, 2H), 1.94 (m, 2H), 1.64 (m, 4H); low resolution mass spectrum (ES+) m/z 349.9 ([M+H]$^+$); calcd for C$_{18}$H$_{20}$ClNO$_2$S+H, 350.1].

Example 16

Synthesis of 1-(1-(4-fluorophenyl)-5-methyl-1H-1,2,3-triazol-4-yl)-2-(pyrrolidin-1-yl)ethanone (A30)

1-(1-(4-fluorophenyl)-5-methyl-1H-1,2,3-triazol-4-yl)-2-(pyrrolidin-1-yl)ethanone (A30)

Step 1: 4-Fluoroaniline (9.66 g, 0.087 mol) was suspended in 50 mL of water and cooled to 0° C. Concentrated HCl (18 mL) and a solution of sodium nitrite (6 g, 0.087 mol) in 20 mL water were slowly added to the stirring solution. After stirring for further for 30 min at 0° C. a solution of sodium azide (5.8 g, 0.087 mol) in 20 mL of water was added slowly and after complete addition, the reaction mixture was warmed to room temperature and stirred for 1 h. Progress of the reaction was monitored by TLC. After completion of the reaction, mixture was diluted with water (200 mL) and extracted with ethyl acetate (2×250 mL). The organic layer was then separated, washed with brine, dried over anhydrous $Na_2SO_4$ and concentrated in vacuo to yield 1-azido-4-fluoro-benzene 30 as brown oil. Yield: (9 g, 75.00%); $^1$H NMR (400 MHz, $CDCl_3$) δ ppm=7.06-7.01 (m, 2H), 6.99-6.95 (m, 2H). IR=2123 $cm^{-1}$. Step 2: To a stirred solution of compound 30 (1.0 g, 0.0072 mol) in 10 mL of DMSO, ethyl acetoacetate (1.9 ml, 0.0143 mol) was added slowly followed by diethylamine (3.8 mL, 0.036 mol). The reaction was heated at 70° C. under a nitrogen atmosphere for 18 h. After completion of the reaction, the mixture was dumped in ice-water (250 mL) and then extracted well with dichloromethane (2×250 mL). The organic phase was washed with brine, dried and evaporated on a rotary evaporator. The crude product was chromatographed on silica gel (100-200 mesh) and eluted with 15% ethylacetate:hexanes system to afford 1-(4-fluoro-phenyl)-5-methyl-1H-[1,2,3]triazole-4-carboxylic acid ethyl ester 31 as off white solid. Yield: (2 g, 100%); $^1$H NMR (400 MHz, $CDCl_3$) δ ppm=7.45-7.42 (m, 2H), 7.28-7.26 (m, 2H), 4.48-4.43 (q, 2H), 2.56 (s, 3H), 1.45-1.42 (t, 3H); low resolution mass spectrum (ES+) m/z 249.9 ([M+H]$^+$); calcd for $C_{12}H_{12}FN_3O_2$+H, 250.1]. Step 3: To a stirred solution of compound 31 (2.0 g, 0.00803 mol) in 90 mL of THF was added a solution of lithium hydroxide (0.580 g) in 10 mL of water. The solution was then stirred at room temperature for 18 h. After completion the reaction mixture was dumped in ice-water (100 mL) and acidified to pH 3-4 by addition of a saturated citric acid solution at 0-5° C. The solid precipitated out was filtered and washed with water to afford 1-(4-fluoro-phenyl)-5-methyl-1H-[1,2,3]triazole-4-carboxylic acid 32 as white solid. Yield: (1.4 g, 93.45%); $^1$H NMR (400 MHz, $CDCl_3$) δ ppm=7.48-7.44 (m, 2H), 7.30-7.26 (m, 2H), 2.61 (s, 3H); low resolution mass spectrum (ES+) m/z 222.1 ([M+H]$^+$); calcd for $C_{10}H_8FN_3O_2$+H, 222.1]. Step 4: To compound 32 (1 g, 0.0045 mol), thionyl chloride (25 mL) was added slowly and carefully at 0° C. and resulting mixture was heated to reflux for 2 h. After completion of the reaction, the excess of thionyl chloride was stripped off under vacuum and then co-evaporated under vacuum with toluene two-three times to remove the traces of thionyl chloride to get brown colored acid chloride as solid. This solid was dissolved in acetonitrile (25 mL) and cooled to 0° C. To this stirring solution was added TMS diazomethane (1.5 mL) and mixture was allowed to come to room temperature over 10 minutes period and stirring was continued for 2 h. After completion of reaction, conc. HCl (5 mL) was added drop wise and stirring was continued for 18 h. The reaction mixture was then quenched with ice (~50 g) and the aqueous layer was extracted with ethyl acetate (2×200 mL). The combined organic layers was washed with brine, dried and concentrated in vacuo to get the crude compound which was purified by column chromatography using 100:200 silica gel. Pure compound was eluted out with 10% ethyl acetate in hexanes which upon concentration afforded 2-chloro-1-[1-(4-fluoro-phenyl)-5-methyl-1H-[1,2,3]triazol-4-yl]-ethanone 33 as off white solid. Yield: (1 g, 87.71%). $^1$H NMR (400 MHz, $CDCl_3$) δ ppm=7.47-7.42 (m, 2H), 7.30-7.25 (m, 2H), 4.99 (s, 2H), 2.60 (s, 3H); low resolution mass spectrum (ES+) m/z 253.8 ([M+H]$^+$); calcd for $C_{11}H_9ClFN_3O$+H, 254.0]. Step 5: To a stirred solution of compound 33 (0.5 g, 0.00197 mol) in 10 mL of dry acetonitrile, TEA (0.8 mL, 0.00395 mol) and pyrrolidine (0.33 mL, 0.00591 mol) were added successively at 0° C. under $N_2$ atmosphere. After complete addition, the reaction mixture was warmed to room temperature and stirred for 30 minutes and monitored by TLC. After completion of the reaction, the mixture was quenched with ice (~50 g) and the aqueous layer was extracted well with ethyl acetate (2×100 mL). The organic layer was washed once with brine solution and dried over anhydrous $Na_2SO_4$. The organic layer was distilled out under vacuum to obtain crude product which was further purified by preparative HPLC to get pure title compound A30 as off white solid. Yield: (0.15 g, 26.78%); $^1$H NMR (400 MHz, $CDCl_3$) δ ppm=7.72-7.69 (m, 2H), 7.53-7.48 (m, 2H), 4.10 (s, 2H), 2.62 (s, 4H), 1.72 (s, 4H); low resolution mass spectrum (ES+) m/z 289.2 ([M+H]$^+$); calcd for $C_{15}H_{27}FN_4O$+H, 289.1].

Example 17

Synthesis of 1-(4-(4-chlorophenyl)piperazin-1-yl)-2-(pyrrolidin-1-yl)ethanone (A31) and 1-(4-(4-fluorophenyl)piperazin-1-yl)-2-(piperidin-1-yl)ethanone (A32)

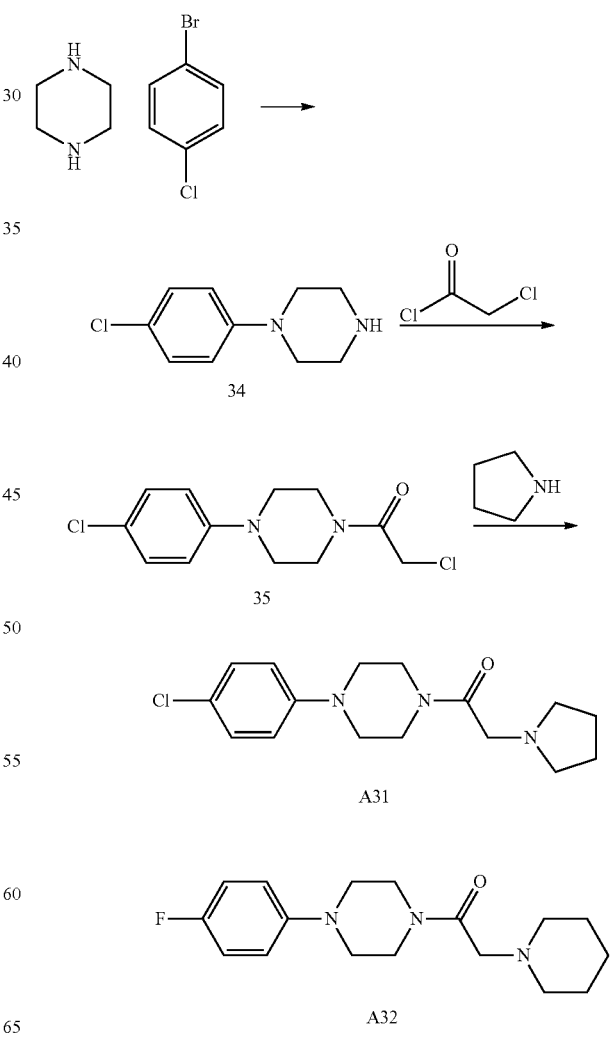

1-(4-(4-chlorophenyl)piperazin-1-yl)-2-(pyrrolidin-1-yl)ethanone (A31)

Step 1: piperazine (1.0 g, 11.6 mmol), 1-bromo-4-chlorobenzene (2.12 g, 11.06 mmol), rac-BINAP (0.275 g, 0.442 mmol), tris(dibenzylideneacetone)dipalladium (0) (0.223 g, 0.243 mmol) and sodium tert-butoxide (2.12 g, 22.11 mmol) were placed in a flame-dried flask. The flask was evacuated and backfilled with nitrogen three times. Toluene (20 mL) was added to the flask and the flask was evacuated and backfilled with nitrogen an additional three times. The reaction was heated to 90° C. overnight. The reaction was cooled to room temperature and the mixture was partitioned between water and ethyl acetate. The aqueous phase was extracted twice with ethyl acetate. The combined organic layers were washed with brine and dried over $MgSO_4$. The solvent was removed under vacuum and the resulting residue was adsorbed onto silica. The desired substituted piperazine 34 was isolated using silica gel chromatography (9:1 $CH_2Cl_2$:MeOH). The material was isolated as a yellow solid (0.8 g, 36% yield). $^1$H NMR (300 MHz, $CDCl_3$) δ ppm 7.21 (m, 2H), 6.85 (m, 2H), 3.12 (m, 4H), 3.05 (m, 4H), 2.47 (bs, 1H); low resolution mass spectrum (ES+) m/z 197.1 ([M+H]$^+$; calcd for $C_{10}H_{13}ClN_2$+H, 197.1]. Step 2: piperazine 34 (0.8 g, 4 mmol) was dissolved in $CH_2Cl_2$ (12 mL) and cooled to 0° C. in an ice bath. Triethylamine (1.1 mL, 8 mmol) and chloroacetyl chloride (0.48 mL, 6.1 mmol) were added sequentially. The reaction stirred overnight and was then diluted with $CH_2Cl_2$ and water. The layers were separated and the aqueous phase was extracted once with $CH_2Cl_2$. The combined organic layers were washed with brine, dried over $MgSO_4$ and concentrated. The material was purified using silica gel chromatography to give 35 as a white solid (0.8 g, 2.9 mmol, 72% yield). $^1$H NMR (300 MHz, $CDCl_3$) δ ppm 7.24 (m, 2H), 6.86 (m, 2H), 4.11 (s, 2H), 3.78 (m, 2H), 3.68 (m, 2H), 3.78 (m, 4H); low resolution mass spectrum (ES+) m/z 273.0 ([M+H]$^+$); calcd for $C_{12}H_{14}Cl_2N_2O$+H, 273.1]. Step 3: Chloride 35 (0.3 g, 1.1 mmol) was taken up in acetonitrile (3 mL). Triethylamine (0.3 mL, 2.2 mmol) was added followed by pyrrolidine (0.08 g, 1.1 mmol). The reaction stirred at room temperature overnight. The next morning the solvent was removed under reduced pressure. The resulting residue was taken up in $CH_2Cl_2$. The organic layer was washed with water and brine then dried over $MgSO_4$. The resulting residue was purified using silica gel chromatography to afford title compound A31 in 30% yield (0.1 g, 0.33 mmol). $^1$H NMR (300 MHz, $CDCl_3$) δ ppm 7.22 (m, 2H), 6.84 (m, 2H), 3.76 (m, 4H)m 3.95 (s, 2H), 3.11 (m, 4H), 2.63 (m, 4H), 1.87 (m, 4H); low resolution mass spectrum (ES+) m/z 308.1 ([M+H]$^+$); calcd for $C_{16}H_{22}ClN_3O$+H, 308.2].

1-(4-(4-fluorophenyl)piperazin-1-yl)-2-(piperidin-1-yl)ethanone (A32)

Compound A32 was prepared from 1-bromo-4-fluorobenzene using the procedure described for the preparation of A31. $^1$H NMR (300 MHz, $CDCl_3$) δ ppm 6.97 (m, 2H), 6.89 (m, 2H), 3.78 (m, 4H), 3.18 (s, 2H), 3.07 (m, 4H), 2.44 (m, 4H), 1.57 (m, 4H), 1.43 (m, 2H); low resolution mass spectrum (ES+) m/z 306.2 ([M+H]$^+$); calcd for $C_{17}H_{24}FN_3O$+H, 305.2].

Example 18

Synthesis of 1-(1-(4-chlorophenyl)-1H-indol-3-yl)-2-(4-hydroxypiperidin-1-yl)ethanone (A33), 1-(1-(4-chlorophenyl)-2-methyl-1H-indol-3-yl)-2-(4-hydroxypiperidin-1-yl)ethanone (A34), 1-(1-(4-chlorophenyl)-1H-indol-3-yl)-2-(piperidin-1-yl)ethanone (A35), 1-(1-(4-chlorophenyl)-2-methyl-1H-indol-3-yl)-2-(piperidin-1-yl)ethanone (A36) 1-(1-(4-chlorophenyl)-1H-indol-3-yl)-2-(pyrrolidin-1-yl)ethanone (A37) and 1-(1-(4-chlorophenyl)-2-methyl-1H-indol-3-yl)-2-(pyrrolidin-1-yl)ethanone (A38)

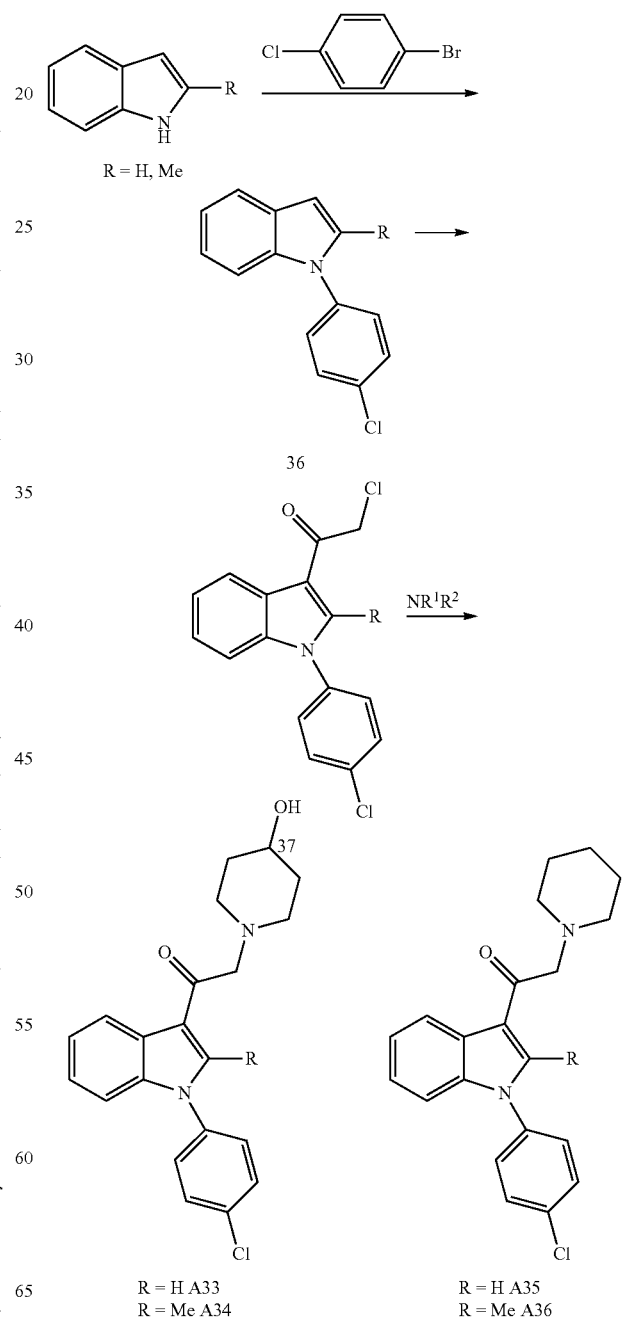

-continued

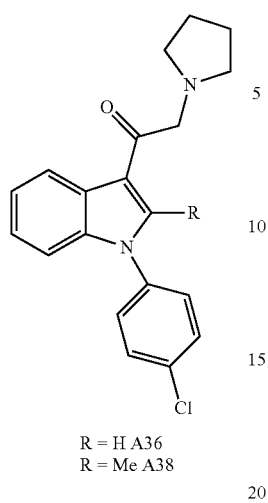

R = H A36
R = Me A38

A palladium catalyzed cross-coupling reaction between commercially available indole and 4-chlorobromobenzene affords indole 36. Fridel-Crafts acylation with chloro acetylchloride (see preparation of A8) then gives intermediate 37. Compound 37 can be treated with a variety of amines to afford compounds such as A33-A38 (see preparation of A11).

Example 19

Preparation of tert-butyl 2-(2-(1-(4-chlorophenyl)-2,5-dimethyl-1H-pyrrol-3-yl)-2-oxoethyl)piperidine-1-carboxylate (A39), 1-(1-(4-chlorophenyl)-2,5-dimethyl-1H-pyrrol-3-yl)-2-(piperidin-2-yl)ethanone (A40) and 1-(1-(4-chlorophenyl)-2,5-dimethyl-1H-pyrrol-3-yl)-2-(1-methylpiperidin-2-yl)ethanone (A41)

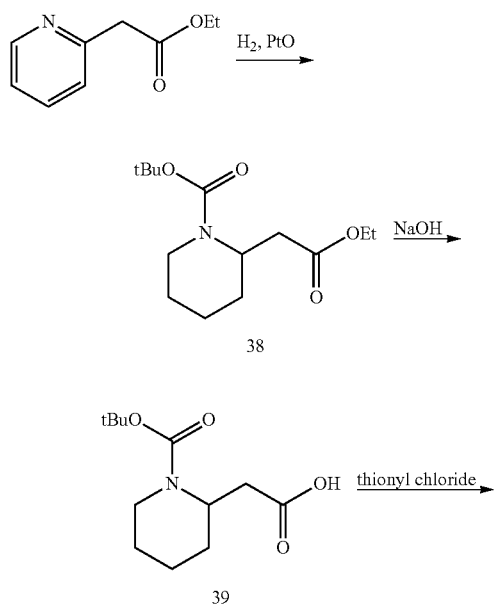

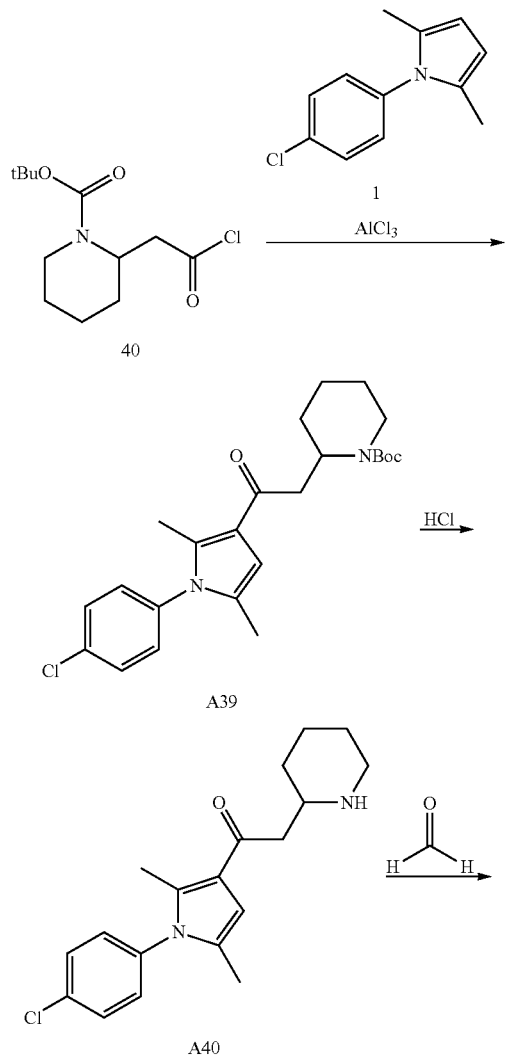

Hydrogenation of commercially available ethyl 2-pyridylacetate with an in-situ Boc protection will afford ester 38 (Birman, V., D. et. al, *Org. Lett,* 2007, 9, 3237.) Hydrolysis of the ester is followed by formation of the acid chloride using thionyl chloride to give acid chloride 40 (PCT Int. Appl. 2005103000, Nov. 3, 2005). Acylation of pyrrole 1 with acid chloride 40 can be accomplished using a Fridel-Crafts acyaltion to give compound A39. Removal of the Boc protecting group with HCl can afford A40. Amine A40 can be methylated using a reductive amination to give compound A41.

Example 20

Preparation of 1-(5-(4-chlorophenyl)-1,4-dimethyl-1H-pyrrol-3-yl)-2-(piperidin-1-yl)ethanone (A42) and 1-(5-(4-chlorophenyl)-1,4-dimethyl-1H-pyrrol-2-yl)-2-(piperidin-1-yl)ethanone (A43)

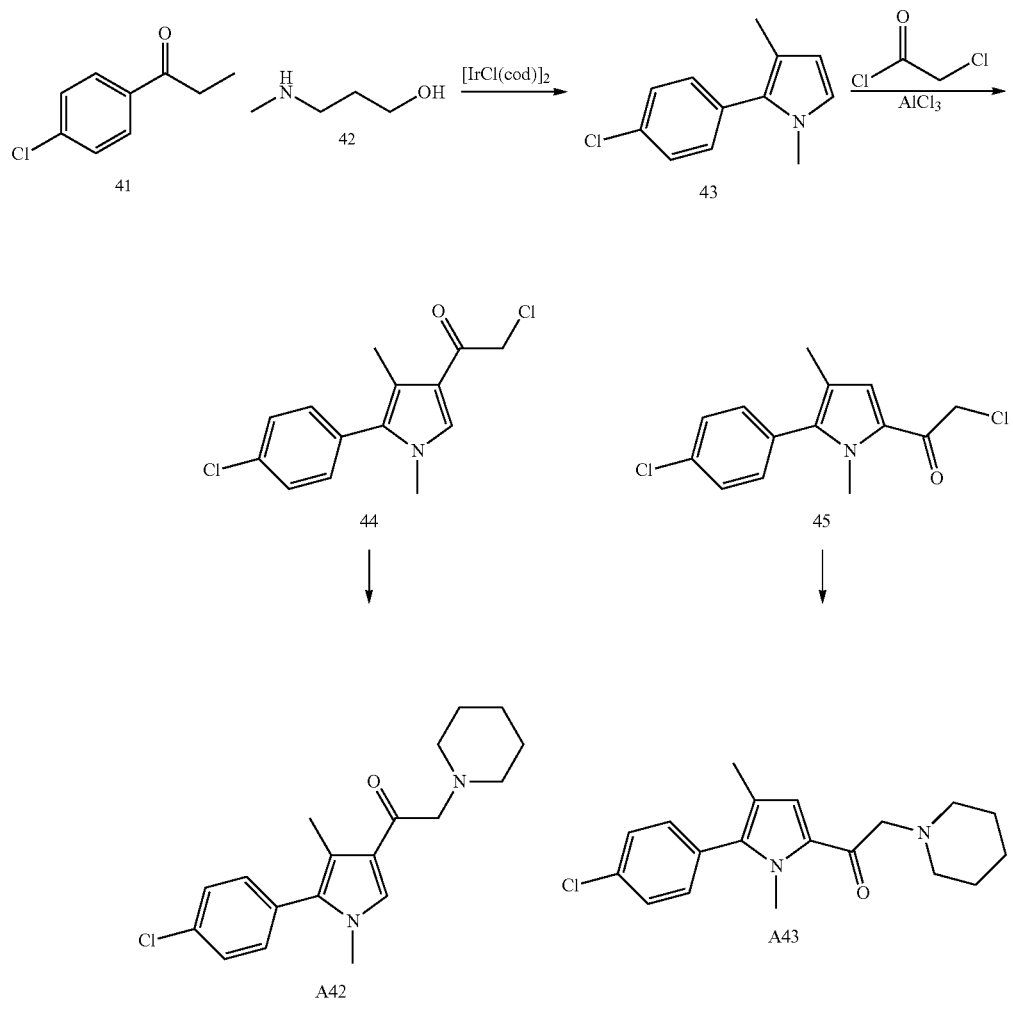

An iridium aided cyclization between ketone 41 and amine 42 will give pyrrole 43 (*Tetrahedron Lett.* 2005, 46, 4539). A Friedel-Crafts acylation using the procedure described for the preparation of A8 described will afford a mixture of 44 and 45. Separation of the mixture and independent reaction with a secondary amine (shown here as piperidine) will provide A42 and A43. The procedure for amine alkylation has been described previously for the preparation of A11 and A12.

Example 21

Biological Activity

Using previously described methodology (B. H. Lee et. al. *Nature* 2010, 467 (9), 179; the contents of which are expressly incorporated by reference herein), select compounds described herein were found to inhibit USP14 as delineated in the table below. Known USP14 inhibitor IU1 (1-(1-(4-fluorophenyl)-2,5-dimethyl_1H-pyrrol-3-yl)-2-(pyrrolidin-1-yl)ethanone; B. H. Lee et. al. *Nature* 2010, 467 (9), 179) was used as a comparative reference agent. The $IC_{50}$ values in the Table below represent the average value from three experimental determinations. In the table below, "A" represents an $IC_{50}$ of 0 to 5 uM, "B" represents an $IC_{50}$ of 5 to 10 uM, and "C" represents and $IC_{50}$ of greater than 10 uM.

Compounds A44, A45 and A46 (shown below) were purchased from Enamine Ltd., Ukraine. Compound A47 (also shown below) was purchased from ChemDiv, San Diego, Calif.

TABLE 6

| Compound | Structure | Activity |
| --- | --- | --- |
| A1 | 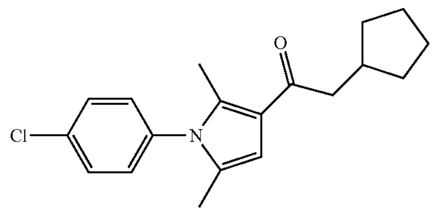 [SMILES: Cc1cc(C(=O)CC2CCCC2)c(C)n1-c1ccc(Cl)cc1] | C |
| A2 | 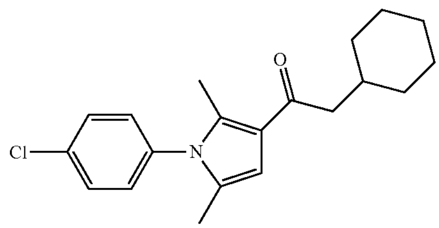 [SMILES: Cc1cc(C(=O)CC2CCCCC2)c(C)n1-c1ccc(Cl)cc1] | C |
| A3 | 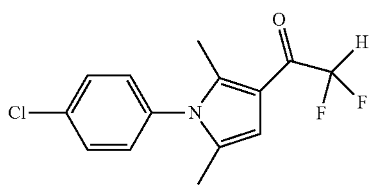 [SMILES: Cc1cc(C(=O)C(F)F)c(C)n1-c1ccc(Cl)cc1] | C |
| A4 | 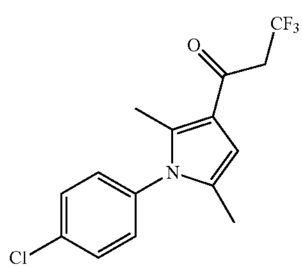 [SMILES: Cc1cc(C(=O)CC(F)(F)F)c(C)n1-c1ccc(Cl)cc1] | C |
| A5 | 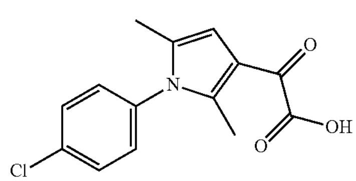 [SMILES: Cc1cc(C(=O)C(=O)O)c(C)n1-c1ccc(Cl)cc1] | C |
| A6 | 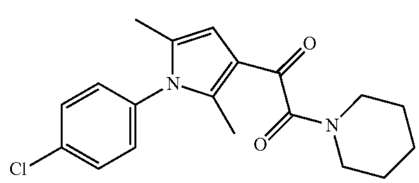 [SMILES: Cc1cc(C(=O)C(=O)N2CCCCC2)c(C)n1-c1ccc(Cl)cc1] | C |
| A7 | 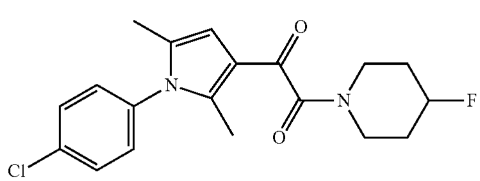 [SMILES: Cc1cc(C(=O)C(=O)N2CCC(F)CC2)c(C)n1-c1ccc(Cl)cc1] | C |

TABLE 6-continued

| Compound | Structure | Activity |
|---|---|---|
| A8 | 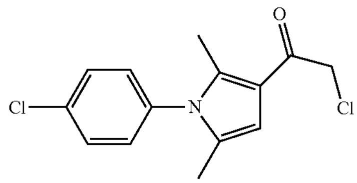 [SMILES: Cc1cc(C(=O)CCl)c(C)n1-c1ccc(Cl)cc1] | C |
| A9 | 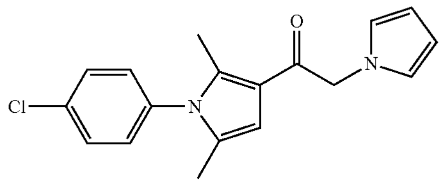 [SMILES: Cc1cc(C(=O)Cn2cccc2)c(C)n1-c1ccc(Cl)cc1] | C |
| A10 | 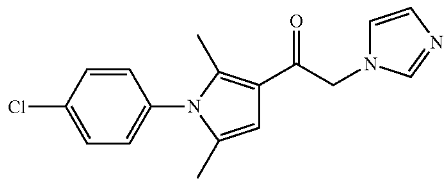 [SMILES: Cc1cc(C(=O)Cn2ccnc2)c(C)n1-c1ccc(Cl)cc1] | C |
| A11 | 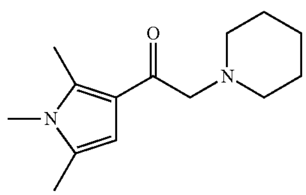 [SMILES: Cc1cc(C(=O)CN2CCCCC2)c(C)n1C] | C |
| A12 | 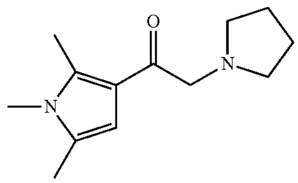 [SMILES: Cc1cc(C(=O)CN2CCCC2)c(C)n1C] | C |
| A13 | 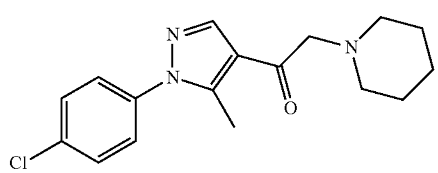 [SMILES: Cc1c(C(=O)CN2CCCCC2)cnn1-c1ccc(Cl)cc1] | A |
| A14 | 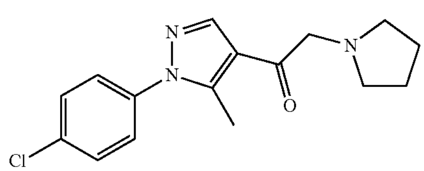 [SMILES: Cc1c(C(=O)CN2CCCC2)cnn1-c1ccc(Cl)cc1] | A |
| A15 | 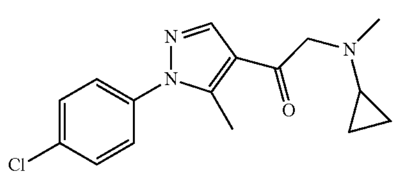 [SMILES: Cc1c(C(=O)CN(C)C2CC2)cnn1-c1ccc(Cl)cc1] | C |

TABLE 6-continued
| Compound | Structure | Activity |
|---|---|---|
| A16 | 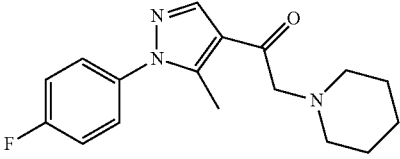 [SMILES: Cc1c(C(=O)CN2CCCCC2)cnn1-c1ccc(F)cc1] | C |
| A18 | 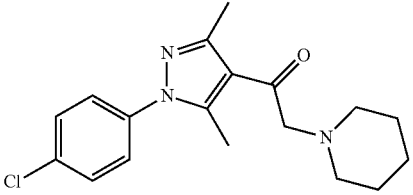 [SMILES: Cc1nn(-c2ccc(Cl)cc2)c(C)c1C(=O)CN1CCCCC1] | B |
| A19 | 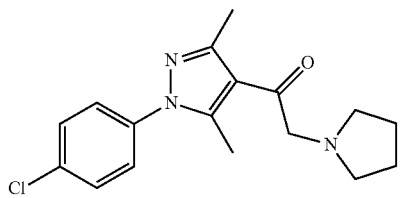 [SMILES: Cc1nn(-c2ccc(Cl)cc2)c(C)c1C(=O)CN1CCCC1] | A |
| A20 | 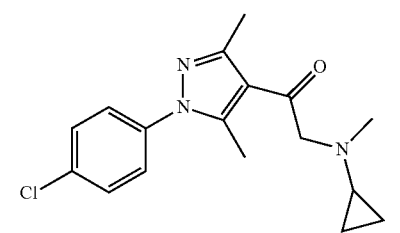 [SMILES: Cc1nn(-c2ccc(Cl)cc2)c(C)c1C(=O)CN(C)C1CC1] | C |
| A21 | 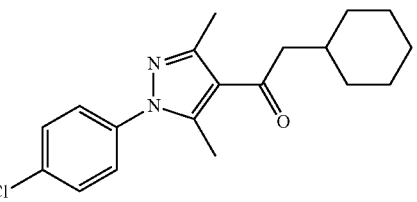 | C |
| A22 | 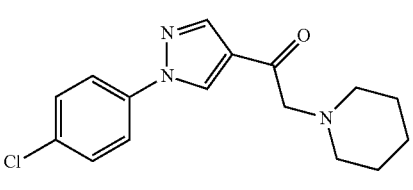 [SMILES: O=C(CN1CCCCC1)c1cnn(-c2ccc(Cl)cc2)c1] | C |
| A23 | 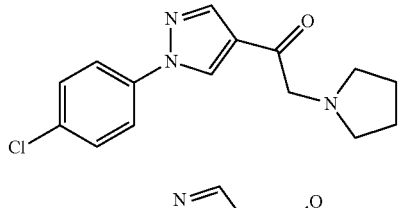 | C |
| A24 | 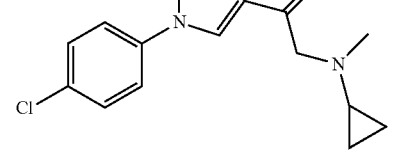 | C |

TABLE 6-continued

| Compound | Structure | Activity |
|---|---|---|
| A25 | 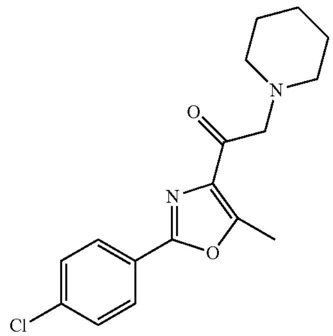 [SMILES: Cc1oc(-c2ccc(Cl)cc2)nc1C(=O)CN1CCCCC1] | C |
| A26 | 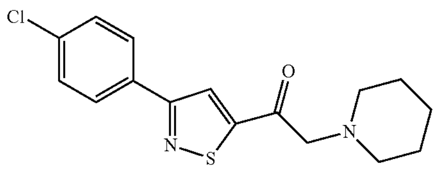 [SMILES: O=C(CN1CCCCC1)c1cc(-c2ccc(Cl)cc2)ns1] | C |
| A27 | 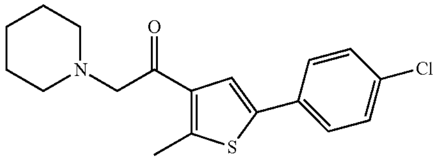 [SMILES: Cc1sc(-c2ccc(Cl)cc2)cc1C(=O)CN1CCCCC1] | C |
| A28 | 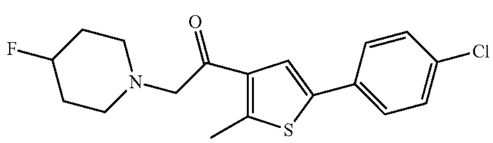 [SMILES: Cc1sc(-c2ccc(Cl)cc2)cc1C(=O)CN1CCC(F)CC1] | C |
| A29 | 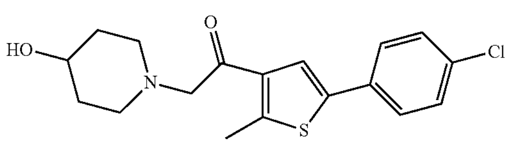 [SMILES: Cc1sc(-c2ccc(Cl)cc2)cc1C(=O)CN1CCC(O)CC1] | C |
| A30 | 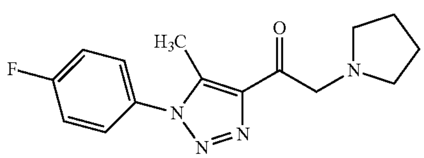 [SMILES: Cc1c(C(=O)CN2CCCC2)nnn1-c1ccc(F)cc1] | C |
| A31 | 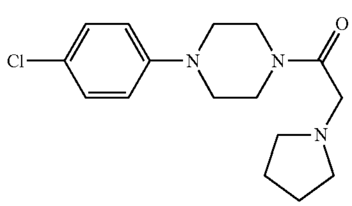 [SMILES: O=C(CN1CCCC1)N1CCN(c2ccc(Cl)cc2)CC1] | C |
| A32 | 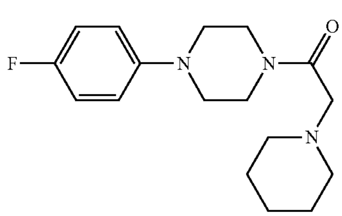 [SMILES: O=C(CN1CCCCC1)N1CCN(c2ccc(F)cc2)CC1] | C |

TABLE 6-continued

| Compound | Structure | Activity |
|---|---|---|
| A44 | 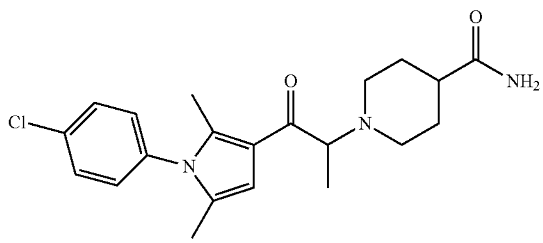 [SMILES: Cc1cc(C(=O)C(C)N2CCC(C(N)=O)CC2)c(C)n1-c1ccc(Cl)cc1] | C |
| A45 | 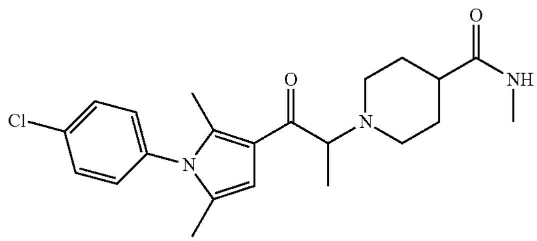 [SMILES: CNC(=O)C1CCN(C(C)C(=O)c2cc(C)n(-c3ccc(Cl)cc3)c2C)CC1] | C |
| A46 | 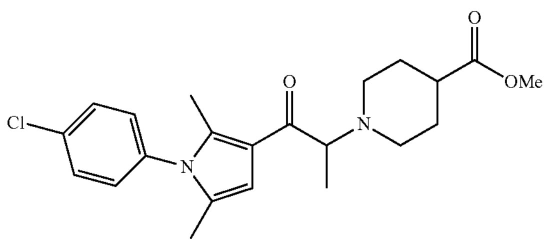 [SMILES: COC(=O)C1CCN(C(C)C(=O)c2cc(C)n(-c3ccc(Cl)cc3)c2C)CC1] | C |
| A47 | 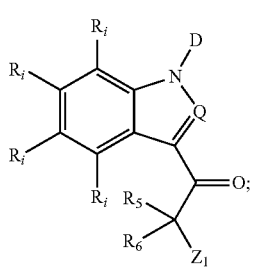 | C. |

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound having the Formula (II):

(II)

or a pharmaceutically acceptable salt, or solvate thereof, wherein:

D is optionally substituted phenyl;

Q is $C(R_d)$;

each $R_i$ is independently selected from the group consisting of hydrogen and optionally substituted $C_1$-$C_{10}$ alkyl;

$R^5$ and $R^6$ are each independently selected from the group consisting of hydrogen and optionally substituted $C_1$-$C_{10}$ alkyl;

$Z_1$ is $NR_cR_c$;

each $R_c$ is independently selected from the group consisting of hydrogen and optionally substituted $C_1$-$C_{10}$ alkyl; or alternatively, the two $R_c$ groups are taken together with the nitrogen atom to which they are attached to form an optionally substituted 3- to 8-membered heterocyclic; and $R_d$ is optionally substituted $C_1$-$C_{10}$ alkyl.

2. A pharmaceutical composition comprising a pharmaceutically acceptable carrier and a compound of claim 1, or a pharmaceutically acceptable salt, or solvate thereof.

3. A compound selected from those shown in the Table below, or a pharmaceutically acceptable salt or solvate thereof:

| Compound | |
|---|---|
| A34 | 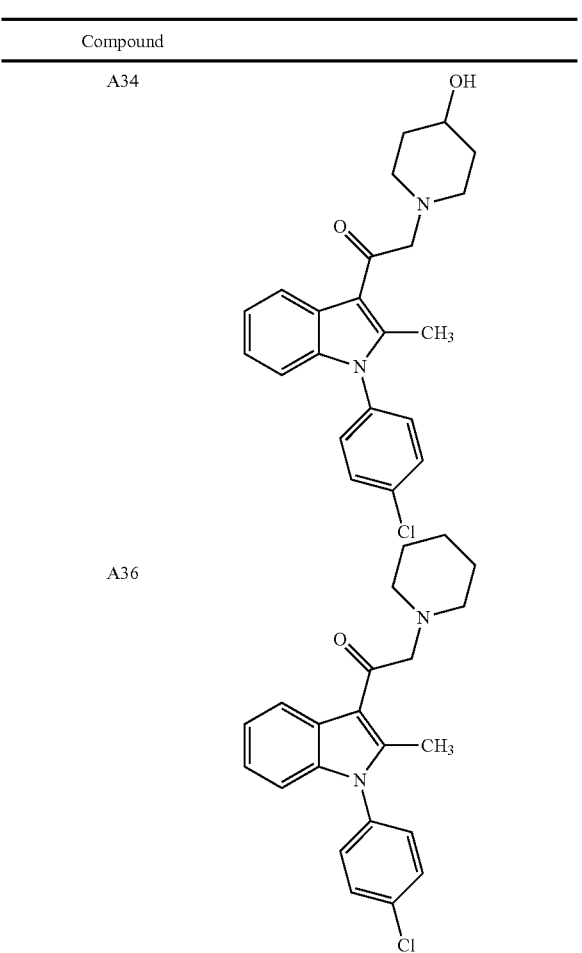 |
| A36 | |

| Compound |
|---|
| A38 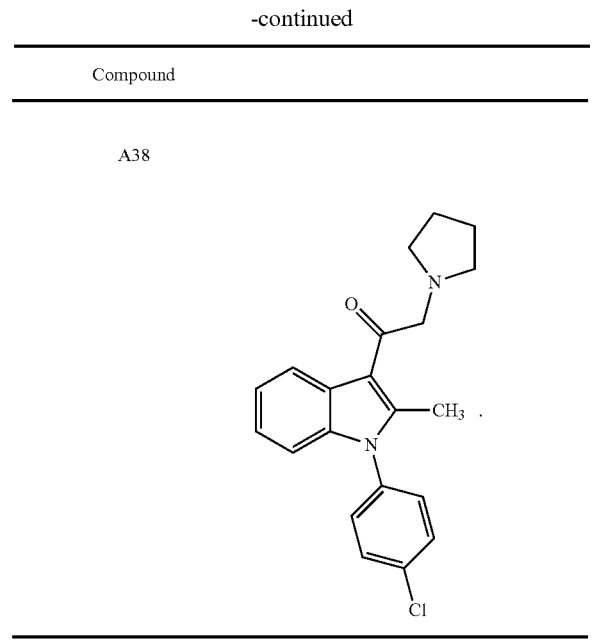 |

4. The compound of claim 1, wherein the two $R_c$ groups are taken together with the nitrogen atom to which they are attached to form an optionally substituted 3- to 8-membered heterocyclic, or a pharmaceutically acceptable salt or solvate thereof.

5. The compound of claim 1, wherein $R_d$ is methyl, or a pharmaceutically acceptable salt or solvate thereof.

\* \* \* \* \*